(12) United States Patent
Kamionka et al.

(10) Patent No.: US 10,538,789 B2
(45) Date of Patent: Jan. 21, 2020

(54) METHODS FOR BIOSYNTHESIS OF ISOPRENE

(71) Applicant: INVISTA NORTH AMERICA S.A.R.L., Wilmington, DE (US)

(72) Inventors: Mariusz Kamionka, Cleveland (GB); Jan Modregger, Vienna (AT); Axel Niebisch, Vienna (AT); Alex Van Eck Conradie, Cleveland (GB); Adriana Leonora Botes, East Cleveland (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 119 days.

(21) Appl. No.: 15/808,409

(22) Filed: Nov. 9, 2017

(65) Prior Publication Data

US 2018/0127788 A1  May 10, 2018

Related U.S. Application Data

(63) Continuation of application No. 14/452,201, filed on Aug. 5, 2014, now Pat. No. 9,862,973.

(60) Provisional application No. 61/862,401, filed on Aug. 5, 2013.

(51) Int. Cl.
| | | |
|---|---|---|
| C12P 5/00 | (2006.01) | |
| C12N 15/70 | (2006.01) | |
| C12P 5/02 | (2006.01) | |
| C12N 9/10 | (2006.01) | |
| C12N 9/12 | (2006.01) | |
| C12N 9/88 | (2006.01) | |
| C12N 15/52 | (2006.01) | |

(52) U.S. Cl.
CPC ............ *C12P 5/007* (2013.01); *C12N 9/1029* (2013.01); *C12N 9/1205* (2013.01); *C12N 9/88* (2013.01); *C12N 15/52* (2013.01); *C12N 15/70* (2013.01); *C12P 5/026* (2013.01); *C12Y 203/01041* (2013.01); *Y02E 50/343* (2013.01)

(58) Field of Classification Search
None
See application file for complete search history.

(56) References Cited

U.S. PATENT DOCUMENTS

| | | |
|---|---|---|
| 8,703,455 B2 | 4/2014 | Marliere |
| 8,741,612 B2 | 6/2014 | Campbell et al. |
| 9,422,578 B2 | 8/2016 | Pearlman ............... C12P 5/02 |
| 9,422,580 B2 | 8/2016 | Pearlman ............... C12P 5/026 |
| 2011/0165644 A1 | 7/2011 | Marliere |
| 2011/0300597 A1 | 12/2011 | Burk et al. |
| 2012/0021478 A1 | 1/2012 | Osterhout et al. |
| 2012/0122563 A1 | 5/2012 | Walker et al. |
| 2012/0225466 A1 | 9/2012 | Burk et al. |
| 2013/0189753 A1 | 7/2013 | Pearlman et al. |
| 2013/0210104 A1 | 8/2013 | Pearlman et al. |
| 2013/0309742 A1 | 11/2013 | Campbell et al. |
| 2014/0065686 A1 | 3/2014 | Marliere |
| 2014/0141482 A1 | 5/2014 | Pearlman et al. |
| 2014/0186913 A1 | 7/2014 | Botes et al. |
| 2015/0079654 A1 | 3/2015 | Botes et al. |
| 2015/0291981 A1 | 10/2015 | Marliere et al. ......... C12P 5/02 |

FOREIGN PATENT DOCUMENTS

| | | |
|---|---|---|
| EP | 2336340 | 6/2011 |
| EP | 2336341 | 6/2011 |
| EP | 12190039 | 10/2012 |
| WO | WO2009/155382 | 12/2009 |
| WO | WO2010001078 | 1/2010 |
| WO | WO2010/099201 | 9/2010 |
| WO | WO2011/011689 | 1/2011 |
| WO | WO 2011/076261 | 6/2011 |
| WO | WO 2011/076689 | 6/2011 |
| WO | WO 2011/076691 | 6/2011 |
| WO | WO 2011/079314 | 6/2011 |
| WO | WO2011/140171 | 11/2011 |
| WO | WO2012/018624 | 2/2012 |
| WO | WO 2012/052427 | 4/2012 |
| WO | WO2012/174439 | 12/2012 |
| WO | WO 2013/007786 | 1/2013 |
| WO | WO 2013/020118 | 2/2013 |
| WO | WO 2013/028519 | 2/2013 |
| WO | WO 2013/040383 | 3/2013 |
| WO | WO2013036812 | 3/2013 |
| WO | WO 2013/057194 | 4/2013 |
| WO | WO2013/082542 | 6/2013 |
| WO | WO 2013/090915 | 6/2013 |
| WO | WO 2013/092567 | 6/2013 |
| WO | WO 2013/150100 | 10/2013 |
| WO | WO 2013/173437 | 11/2013 |
| WO | WO 2013/181647 | 12/2013 |
| WO | WO 2013/192183 | 12/2013 |
| WO | WO2013188546 | 12/2013 |
| WO | WO 2014/001517 | 1/2014 |

(Continued)

OTHER PUBLICATIONS

Akatsuka et al., "The Serratia marcescens bioH gene encodes an esterase," GENE, Jan. 2003, 302:185-192.

Eriksen et al., "Protein Design for Pathway Engenieering," Journal of Structural Biology, Apr. 2013, 185(2):234-242.

Invitation to pay additional fees and, where applicable, protest fee for PCT/US2015/036095, dated Sep. 18, 2015, 13 pages.

Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.

(Continued)

*Primary Examiner* — Kagnew H Gebreyesus
(74) *Attorney, Agent, or Firm* — Licata & Tyrrell P.C.; Robert B. Furr, Jr.

(57) ABSTRACT

This document describes biochemical pathways for producing isoprene by forming two vinyl groups in a central precursor produced from isobutyryl-CoA, 3-methyl-2-oxopentanoate, or 4-methyl-2-oxopentanoate as well as recombinant hosts for producing isoprene.

2 Claims, 19 Drawing Sheets

Specification includes a Sequence Listing.

(56) References Cited

FOREIGN PATENT DOCUMENTS

| WO | WO 2014/033129 | 3/2014 |
|---|---|---|
| WO | WO2014/064198 | 5/2014 |
| WO | WO2014/085612 | 6/2014 |
| WO | WO 2014/015210 | 11/2014 |

OTHER PUBLICATIONS

Lin et al., "Biotin Sythesis Begins by Hijacking the Fatty Acid Synthetic Pathway," Nature Chem Biol., Sep. 2010, 6:682-688.
Uniprot Accession No. 032472, Jun. 11, 2014, 2 pages.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A6Q6, Jun. 11, 2014, 3 pages.
Uniprot Accession No. P0A953, Jun. 11, 2014, 4 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
U.S. Final Office Action in U.S. Appl. No. 14/092,115, dated Oct. 27, 2015, 8 pages.
Westin et al., "The identification of a succinyl-CoA thioesterase suggests a novel pathway for succinate production in peroxisomes," J. Biol Chem, 2005, 280:38125-38132.
International Search Report and Written Opinion in Application No. PCT/U S2014/049786, dated Sep. 11, 2015, 17 pages.
Chinese Office Action in Chinese Application No. 201280040122.2, dated Jul. 17, 2015, 7 pages.
International Preliminary Report on Patentability and Written Opinion for PCT/US2013/072275, dated Jun. 2, 2015, 8 pages.
"Production of butadiene," China Synthetic Rubber Industry, Special issue of 1978, 21 pages (with partial English translation).
U.S. Non-Final Office Action in U.S. Appl. No. 13/916,156, dated Jul. 14, 2015, 35 pages.
U.S. Non-Final Office Action in U.S. Appl. No. 13/524,973, dated Jul. 23, 2015, 24 pages.
Zhang et al., "Genes encoding acyl-CoA dehydrogenase (AcdH) homologues from Streptomyces coelicolor and Streptomyces avermitilis provide insights into the metabolism of small branched-chain fatty acids and macrolide antibiotic production," Microbiology, 1999, 145(9):2323-2334, 12 pages.
Zhuang et al., "Divergence of function in the Hotdog-fold enzyme superfamily: the bacterial thioesterase YciA," Biochemistry, 2008, 47(9):2789-2796, 8 pages.
Daniel et al., "Biochemistry of coenzyme B12-dependent glycerol and diol dehydratases and organization of the encoding genes," 1999, FEMS Microbiology Reviews, 22: 553-566.
Genbank accession No. E1XUJ2.1. Sep. 5, 2012, 2 pages.
International Preliminary Report on Patentability in International Application No. PCT/US2013/045430, dated Dec. 24, 2014, 12 pages.
Jin et al., "The selective addition of water to C=C bonds; enzymes are the best chemists," Chem Commun., 2011, 47:2502-2510.
Kelada et al., "Delta-aminolevulinic acid dehydratase genotype and lead toxicity: A Huge Review," Am. J. Epidemiology, 2001, 154(1)1-13.
Luddeke et al. "Geraniol and Geranial Dehydrogenases Induced in Anaerobic Monoterpene Degradation by Castellaniella defragrans," Appl. and Environmental Microbiology, 2012, 78(7): 2128-2136.
Luddeke et al.,"Enantiospecific (S)-(+)-linalool formation from beta-myrcene by linalool dehydratase-isomerase," Z Naturforsch C., Jul./Aug. 2011, 66(7-8):409-412.
Toraya, "Radical catalysis of B12 enzymes: structure, mechanism, inactivation and reactivation of diol and glycerol dehydratases," Cellular and Molecular Life Sciences, 2000, 57:106-127.

U.S. Final Office Action in U.S. Appl. No. 13/691,623, dated Dec. 9, 2014, 15 pages.
U.S. Final Office Action in U.S. Appl. No. 13/524,973, dated Dec. 22, 2014, 24 pages.
U.S. Non-Final Office Action in U.S. Appl. No. 13/092,115, dated Apr. 1, 2015, 21 pages.
Barta et al., "Structural basis for nucleotide binding and reaction catalysis in mevalonate diphosphate decarboxylase," *Biochemistry*, 51(28):5611-5621, Epub Jul. 6, 2012.
Becker et al., "Metabolic flux engineering of L-lysine production in Corynebacterium glutamicum—over expression and modification of G6P dehydrogenase," *Journal of Biotechnology*, 132(2):99-109, Epub Jun. 6, 2007
Brigham et al., "Engineering Ralstonia eutropha for Production of Isobutanol from $CO_2$, $H_2$, and $O_2$," Advanced Biofuels and Bioproducts, Chapter 39, 1065-1090, 2012.
Brodkorb et al., "Linalool dehydratase-isomerase, a bifunctional enzyme in the anaerobic degradation of monoterpenes," *J Biol Chem.*, 285(40):30436-30442, Epub Jul. 27, 2010.
Buckel et al., "Glutaconate CoA-transferase from Acidaminococcus feimentans," *Eur J Biochem.*, 118(2):315-321, Aug. 1981
Buckel et al., "2-Hydroxyacyl-CoA dehydratases, a novel family of molybdenum enzymes," J Inorganic Biochemistry, 2003, 96(1):53, 1 page.
Bugg et al., "The emerging role for bacteria in lignin degradation and bio-product formation," *Curr Opin Biotechnol.*, 22(3):394-400, Epub Nov. 9, 2010.
Chayabutra and Ju, "Degradation of n-hexadecane and its metabolites by Pseudomonas aeruginosa under microaerobic and anaerobic denitrifying conditions," *Appl Environ Microbiol.*, 66(2):493-498, Feb. 2000.
Chung and Rhee, "Overexpression of the (R)-specific enoyl-CoA hydratase gene from Pseudomonas chlororaphis HS21 in Pseudomonas strains for the biosynthesis of polyhydroxyalkanoates of altered monomer composition," Biosci. Biotechnol. Biochem., 76(3): 613-616, 2012.
Dhe-Paganon et al., "Mechanism of mevalonate pyrophosphate decarboxylase: evidence for a carbocationic transition state," *Biochemistry*, 33(45):13355-13362, Nov. 15, 1994.
Eikmanns and Buckel, "Crystalline green 5-hydroxyvaleryl-CoA dehydratase from Clostridium aminovalericum," *Eur. J. Biochem.*, 197(3):661-668, May 8, 1991.
European Communication Pursuant to Rules 161(1) and 162 EPC in application No. EP 12799032.3, dated Jun. 25, 2014, 13 pages.
Ferrandez et al., "Genetic characterization and expression in heterologous hosts of the 3-(3-hydroxyphenyl)propionate catabolic pathway of *Escherichia coli* K-12," *J. Bacteriol.*, 179(8): 2573-2581, Apr. 1997
Forster-Fromme et al., "Biochemical characterization of isovaleryl-CoA dehydrogenase (LiuA) of Pseudomonas aeruginosa and the importance of liu genes for a functional catabolic pathway of methyl-branched compounds," FEMS Microbiol Lett, 2008, 286(1):78-84.
Fukui et al., "Expression and characterization of ®-specific enoyl coenzyme A hydratase involved in polyhydroxyalkanoate biosynthesis by Aeromonas caviae," J. Bacteriology, Feb. 1998, 180(3):667-673.
Gehret et al., "Terminal alkene formation by the thioesterase of curacin A biosynthesis: structure of a decarboxylating thioesterase," J. of Biological Chem., 2011, 186(16):14445-14454.
GENBANK accession No. AAD44196.1, Oct. 15, 1999, 1 page.
GENBANK accession No. AAG05403.1, Jan. 31, 2014, 2 pages.
GENBANK accession No. AAV40818.1, Feb. 4, 2005, 1 page.
GENBANK accession No. AAV40819.1, Feb. 4, 2005, 1 page.
GENBANK accession No. AAV40820.1, Feb. 4, 2005, 1 page.
GENBANK accession No. BAA21816.1, Aug. 19, 1997, 2 pages.
GENBANK accession No. BAA92740, Aug. 1, 2007, 2 pages.
GENBANK accession No. CAA32465.1, Jul. 26, 1995, 1 page.
GENBANK accession No. CAA32466.1, Jul. 26, 1995, 1 page.
GENBANK accession No. CAA42196.1, Oct. 16, 1995, 1 page.
GENBANK accession No. CAA99573.1, Nov. 14, 2006, 2 pages.
GENBANK accession No. NP 746661, Jun. 27, 2013, 2 pages.

(56) References Cited

OTHER PUBLICATIONS

Gogerty and Bobik, "Formation of isobutene from 3-hydroxy-3-methylbutyrate by diphosphomevalonate decarboxylase," *Appl Environ Microbiol.*, 76(24):8004-8010, Epub Oct. 22, 2010.
Gu et al., "Polyketide Decarboxylative chain Termination Preceded by 0-sulfonation in curacin A Biosynthesis," J. Am. Chemical Soc., Nov. 2009, 131(44):16033-16035.
Guan et al., "Cytochrome P450-dependent desaturation of lauric acid: isoform selectivity and mechanism of formation of 11-dodecenoic acid," *Chem Biol Interact.*, 110(1-2):103-121, Mar. 1998.
He and Spain, "A novel 2-aminomuconate deaminase in the nitrobenzene degradation pathway of Pseudomonas pseudoalcaligenes JS45," *J Bacteriol.*, 180(9):2502-2506, May 1998.
Hermann et al, "Industrial production of amino acids by coryneform bacteria," *J Biotechnol.*, 104(1-3):155-172, Sep. 2003
International Preliminary Report on Patentability and Written Opinion for PCT/US2012/042757, dated Dec. 17, 2013, 7 pages.
International Preliminary Report on Patentability and Written Opinion for PCT/US2012/064407, dated May 13, 2014, 8 pages.
International Preliminary Report on Patentability and Written Opinion for PCT/US2012/067463, dated Jun. 3, 2014, 12 pages.
International Search Report in Application No. PCT/US2012/042757 dated Mar. 6, 2013, 5 pages.
International Search Report in Application No. PCT/US2012/064407, dated Feb. 7, 2013, 13 pages.
International Search Report in Application No. PCT/US2012/067463, dated Jun. 17, 2013, 19 pages.
International Search Report and Written Opinion in Application No. PCT/US2013/072275, dated Mar. 6, 2014, 12 pages.
International Search Report and Written Opinion in Application No. PCT/US2013/045430, dated Feb. 3, 2014, 20 pages.
International Search Report and Written Opinion in Application No. PCT/US2014/048606, dated Oct. 31, 2014, 19 pages.
International Search Report and Written Opinion in Application No. PCT/US2014/049807, dated Nov. 5, 2014, 56 pages.
Invitation to pay additional fees and, where applicable, protest fee for PCT/US2012/067463, dated Mar. 13, 2013, 17 pages.
Invitation to pay additional fees and, where applicable, protest fee for PCT/US2013/045430, dated Nov. 25, 2013, 6 pages.
Jang et al., "Bio-based production of C2-C6 platfatm chemicals," *Biotechnol Bioeng.*, 109(10):2437-2459, Epub Jul. 13, 2012.
Jaremko et al., "The initial metabolic conversion of levulinic acid in Cupriavidus necator," J Biotechnol, 2011, 155(3):293-298.
Kasai et al., "Uncovering the protocatechuate 2,3-cleavage pathway genes," *J Bacteriol.*, 191(21):6758-6768, Epub Aug. 28, 2009.
Kim et al., "An allylic ketyl radical intermediate in clostridial amino-acid fermentation," *Nature.*, 452(7184):239-242, Mar. 2008.
Kim et al., "Dehydration of ®-2-hydro9xyacyl-CoA to enoyl-CoA in the fermentation of α-amino acids by anaerobic bacteria," FEMS Microbiol Rev, 2004, 28(4):455-468, 14 pages.
Kim, "On the enzymatic mechanism of 2-hydroxyisocaproyl-CoA dehydratase from Clostridium difficile," 2004, Ph.D. dissertation, Philipps-Universität, Marburg, 2004.
Kizer et al., "Application of Functional Genomics to Pathway Optimization for Increased Isoprenoid Production," *Applied and Environmental Microbiology*, 2008, 74(10):3229-3241.
Köpke et al., "2,3-Butanediol production by acetogenic bacteria, an alternative route to chemical synthesis, using industrial waste gas," App Enviro Microbiol, 2011, 77(15):5467-5475.
Kuzma et al., "Bacteria produce the volatile hydrocarbon isoprene," *Curr Microbiol.*, 30(2):97-103, Feb. 1995.
Kuzuyama, "Mevalonate and nonmevalonate pathways for the biosynthesis of isoprene units," *Biosci Biotechnol Biochem.*, 66(8):1619-1627, Aug. 2002.
Lan et al., "ATP drives direct photosynthetic production of 1-butanol in cyanobacterial," PNAS, 2012, 109(16):6018-6023, 6 pages.
Lee et al., "Synthesis of pure meso-2,3-butanediol from crude glycerol using an engineered metabolic pathway in *Escherichia coli*," Appl Biochem Biotechnol, 2012, 166(7):1801-1813.
Lee et al., "Conversion of beta-methylbutyric acid to beta-hydroxy-beta-methylbutyric acid by Galactomyces reessii," Appl Environ Microbiol, 1997, 63(11):4191-4195, 5 pages.
Li et al., "Cupriavidus necator JMP134 rapidly reduces furfural with a Zn-dependent alcohol dehydrogenase," Biodegradation, 22(6): 1215-1225, Nov. 2011.
Li et al., "JMP134 rapidly reduces furfural with a Zn-dependent alcohol dehydrogenase," Biodegradation, 2011, 22(6):1215-1225, 11 pages.
Lim et al., "Amplification of the NADPH-Related Genes zwf and gnd for the Oddball Biosynthesis of PHBin an *E. coli* Tranformant Harboring a Cloned phbCAB Operon," J Bioscience and Bioengineering, 2002, 93(6):543-549.
Liu et al., "Microbial production of R-3-hydroxybutyric acid by recombinant *E. coli* harboring genes of phbA, phbB, and tesB," *Appl Microbiol Biotechnol.*, 76(4):811-818, Epub Jul. 4, 2007.
Luo et al., "Production of 3-hydroxypropionic acid through propionaldehyde dehydrogenase PduP mediated biosynthetic pathway in Klebsiella pneumoniae," *Bioresour Technol.*, 103(1):1-6, Epub Oct. 2, 2011.
Martin et al., "High-titer production of monomeric hydroxyl valerates from levulinic acid I Pseudomonas putida," J Biotechnol, 2009, 139(1):61-67.
Martin et al., "Engineering a Mevalonate pathway to *Escherichia coli* for production of terpenoids," *Nature Biothechnology*, 2003, 21:796-802.
McCarthy et al., "Structural basis of functional group activation by sulfotransferases in complex metabolic pathways," ACS Chem. Biol., 2012, 7:1994-2003.
Meijnen et al., "Improved p-hydroxybenzoate productoin by engineered Pseudomonas putida S12 by using a mixed-substrate feeding strategy," Appl Microbiol Biotechnol, 2011, 90(3):885-893.
Mo et al., "Biosynthesis of the allylmalonyl-CoA extender unit for the FK506 polyketide synthase proceeds through a dedicated polyketide synthase and facilitates the mutasynthesis of analogues," *J Am Chem Soc.*, 133(4):976-985, Epub Dec. 22, 2010 [author manuscript].
Morone et al., "Increasing diterpene yield with a modular metabolic engineering system in *E. coli*: comparison of MEV and MEP isoprenoid precursor pathway engineering," *Applied Microbiology and Biotechnology*, 2010, 85:1893-1906.
Muraki et al., "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescens strain KU-7," *Appl Environ Microbiol.*, 69(3):1564-1572, Mar. 2003.
Ohashi et al., "Continuous production of lactic acid from molasses by perfusion culture of Lactococcus lactic using a stirred ceramic membrane reactor," J Bioscience and Bioengineering, 1999, 87(5):647-654.
Papanikolaou et al., "Citric acid production by Yarrowia lipolytica cultivated on olive-mill wastewater-based media,"Bioresour. Technol., 2008, 99(7):2419-2428.
Pérez-Pantoja et al., "Metabolic reconstruction of aromatic compounds degradation from the genome of the amazing pollutant-degrading bacterium Cupriavidus necator JMP134," FEMS Microbiol Rev., 2008, 32(5):736-794.
Prather et al., "De nova biosynthetic pathways: rational design of microbial chemical factories," 2008, 19:468-474.
Prybylski et al., "Third-generation feed stocks for the clean and sustainable biotechnological production of bulk chemicals: synthesis of 2-hydroxyisobutyric acid," Energy, Sustainability and Society, 2012, 2:11.
Ramsay et al., "Use of a Nylon Manufacturing Waste as an Industrial Fermentation Substrate," Appl Environ Microbiol, 1986, 52(1):152-156.
Rettie et al., "CYP4 Isozyme Specificity and the Relationship between co-Hydroxylation and Terminal Desaturation of Valproic Acid," Biochemistry, 34(24): 7889-7895 (1995).
Rude et al., "Terminal olefin (1-alkene) biosynthesis by a novel p450 fatty acid decarboxylase from Jeotgalicoccus speciesm," Appl. Environ. Microbiol., 2011, 77(5):1718-1727.

(56) References Cited

OTHER PUBLICATIONS

Schäfer et al., "Synthesis of short-chain diols and unsaturated alcohols from secondary alcohol substrates by the Rieske nonheme mononuclear iron oxygenase MdpJ.," Appl Environ Microbiol., 78(17):6280-6284, Epub Jun. 29, 2012.
Scherf and Buckel, "Purification and properties of an iron-sulfur and FAD-containing 4-hydroxybutyryl-CoA dehydratase/vinylacetyl-CoA delta 3-delta 2-isomerase from Clostridium aminobutyricum," Eur J Biochem., 215(2):421-429, Jul. 15, 1993.
Scherf et al., "Succinate-ethanol fermentation in Clostridium kluyveri: purification and characterisation of 4-hydroxybutyryl-CoA dehydratase/vinylacetyl-CoA delta 3-delta 2-isomerase," Arch Microbiol., 161(3):239-245, 1994.
Seedorf et al., "The genome of Clostridium kluyveri, a strict anaerobe with unique metabolic features," Proc Natl Acad Sci USA, 2008, 105(6):2128-2133.
Shen et al., "Driving Forces Enable High-Titer Anaerobic 1-Butanol Synthesis in Escherichia coli," Appl Environ Microbiol., 2011, 77(9):2905-2915.
Silver and Fall, "Characterization of aspen isoprene synthase, an enzyme responsible for leaf isoprene emission to the atmosphere," J Biol Chem., 270(22):13010-13016, Jun. 2, 1995.
Sweeney et al., "Physiologically based pharmacokinetic modeling of 1,3-butadiene, 1,2-epoxy-3-butene, and 1,2:3,4-diepoxybutane toxicokinetics in mice and rats" Carcinogenesis., 18(4):611-625, Apr. 1997.
Tseng et al., "Biosynthesis of chiral 3-hydroxyvalerate from single propionate-unrelated carbon sources in metabolically engineered E. coli," Microb Cell Fact., 9:96, Nov. 27, 2010.
Tsuge et al., "Molecular characterization and properties of (R)-specific enoyl-CoA hydratases from Pseudomonas aeruginosa: metabolic tools for synthesis of polyhydroxyalkanoates via fatty acid beta-oxidation," Int J Biol Macromol., 31(4-5):195-205, Jan. 2003.
Ulmer et al., "Bacterial production of poly(.beta.-hydroxyalkanoates) containing unsaturated repeating units by Rhodospirillum rubrum," Macromolecules, 27(7):1675-1679, 1994.
Uniprot Accession No. B8ZLF3, Jun. 15, 2010, 2 pages.
Uniprot Accession No. I3RA72, Sep. 5, 2012, 2 pages.
Uniprot Accession No. P32377, Jun. 15, 2010, 4 pages.
Uniprot Accession No. Q7CCL9, Jun. 15, 2010, 2 pages.
Upton and Mckinney, "Role of the methylcitrate cycle in propionate metabolism and detoxification in Mycobacterium smegmatis," Microbiology, 153(Pt 12):3973-3982, Dec. 2007.
U.S. Non-Final Office Action in U.S. Appl. No. 13/691,623, dated Jun. 25, 2014, 13 pages.
U.S. Non-Final Office Action in U.S. Appl. No. 13/524,973, dated Jun. 11, 2014, 17 pages.
Van Leeuwen et al., "Fermentative production of isobutene," Appl Microbiol Biotechnol, 2012, 93(4):1377-1387.
Wang and Liao, "Alteration of product specificity of Rhodobacter sphaeroides phytoene desaturase by directed evolution," J Biol Chem., 276(44):41161-41164, Epub Aug. 28, 2001.
Wee et al., "Biotechnological production of lactic acid and its recent applications," Food Technol. Biotechnol., 2006, 44(2):163-172.
Wendt et al., "Crystal structure of the carboxyltransferase subunit of the bacterial sodium ion pump glutaconyl-coenzyme A decarboxylase," EMBO J., 22(14):3493-3502, Jul. 15, 2003.
White, "Butadiene production process overview," Chem Biol Interact., 166(1-3):10-14, Epub Jan. 26, 2007.
Yang et al., "Enhancing production of bio-isoprene using hybrid MVA pathway and isoprene synthase in E. coli," PLoS One, Apr. 2012, 7:1-7.
Yang et al., "Value-added uses for crude glycerol—a byproduct of biodiesel production," Biotechnology for Biofuels, 2012, 5:13, 10 pages.
Zhao et al., "Biosynthesis of isoprene in Escherichia coli via methylerythritol phosphate (MEP) pathway," Applied Microbilogy and Biotechnology, Apr. 2011, 90:1915-1922.
Office Communication dated Dec. 3, 2015 in U.S. Appl. No. 13/916,156, filed Jun. 12, 2013.
Office Communication dated Mar. 15, 2016 in U.S. Appl. No. 13/916,156, filed Jun. 12, 2013.
Office Communication dated Apr. 7, 2016 in U.S. Appl. No. 13/916,156, filed Jun. 12, 2013.
Office Communication dated Apr. 20, 2016 in U.S. Appl. No. 13/916,156, filed Jun. 12, 2013.
Office Communication dated May 17, 2016 in U.S. Appl. No.. 13/916,156, filed Jun. 12, 2013.
Office Communication dated Dec. 7, 2015 in U.S. Appl. No. 13/691,623, filed Nov. 30, 2012.
Office Communication dated May 4, 2016 in U.S. Appl. No. 13/691,623, filed Nov. 30, 2012.
Office Communication dated Apr. 20, 2016 in U.S. Appl. No. 13/524,973, filed Jun. 15, 2012.
Office Communication dated Aug. 30, 2016 in U.S. Appl. No. 13/524,973, filed Jun. 15, 2012.
Office Communication dated Jan. 26, 2017 in U.S. Appl. No. 13/524,973, filed Jun. 15, 2012.
Office Communication dated Feb. 2, 2016 in U.S. Appl. No. 14/092,115, filed Jun. 12, 2013.
Office Communication dated Mar. 21, 2016 in U.S. Appl. No. 14/092,115, filed Jun. 12, 2013.
Office Communication dated Jul. 12, 2016 in U.S. Appl. No. 14/092,115, filed Jun. 12, 2013.
Office Communication dated Oct. 12, 2016 in U.S. Appl. No. 14/092,115, filed Jun. 12, 2013.
Office Communication dated Nov. 17, 2016 in U.S. Appl. No. 14/914,741, filed Feb. 26, 2016.
Office Communication dated Feb. 7, 2017 in U.S. Appl. No. 14/914,741, filed Feb. 26, 2016.
Office Communication dated Feb. 5, 2016 in U.S. Appl. No. 14/334,190, filed Jul. 17, 2014.
Office Communication dated Jul. 27, 2016 in U.S. Appl. No. 14/334,190, filed Jul. 17, 2014.
Office Communication dated Jan. 20, 2017 in U.S. Appl. No. 14/334,190, filed Jul. 17, 2014.
Office Communication in EP12731825.1 dated Nov. 17, 2015.
Office Communication in CN201280068870.1 dated Aug. 23, 2016.
Office Communication in EP12799032.3 dated Jun. 16, 2016.
Office Communication in EP12799032.3 dated Mar. 3, 2016.
Office Communication in EP12799032.3 dated Dec. 10, 2015.
Office Communication in CN201280040122.2 dated Jun. 8, 2016.
Office Communication in CN201280040122.2 dated Jul. 17, 2015.
Office Communication in CN201380043586.3 dated Nov. 8, 2016.
Office Communication in EP13812263.5 dated Jan. 12, 2017.
Chica et al. "Semi-rational approached to engineering enzyme activity: combining the benefits of directed evolution and rational design" Current Opinion in Biotechnology 2005 16:378-384.
Liu et al. "Zirconia microbial hollow fibre bioreactor for Escherichia coli culture" Ceramics International 2010 36:2087-2093.
Sen et al. "Developments in Directed Evolution for Improving Enzyme Functions" Appl. Biochem. Biotechnol. 2007 143:212-223.
Studier, F.W. "Protein production by auto-induction in high density shaking cultures" Protein Expression and Purification 2005 41:207-234.
International Preliminary Report on Patentability in PCT/US2014/049786 dated Feb. 9, 2016.
Office communication dated May 20, 2016 from U.S. Appl. No. 14/452,201, filed Aug. 5, 2014.
Office communication dated Oct. 28, 2016 from U.S. Appl. No. 14/452,201, filed Aug. 5, 2014.
Office communication dated Apr. 5, 2017 from U.S. Appl. No. 14/452,201, filed Aug. 5, 2014.
Office communication dated Aug. 30, 2017 from U.S. Appl. No. 14/452,201, filed Aug. 5, 2014.

FIG. 9A

| SEQ ID | Gene designation | Organism | GENBANK reference | FASTA sequence |
|---|---|---|---|---|
| 1 | YsiB | Bacillus subtilis | CAA99573.1 | MNAJSLAVDQFVAVLTIHNPPANALSSRILEELSSCLDQCETDAGVRSIIHGEGRFFSAGADIKEFTSLKGNEDSSLLAERGQQLMERIESFPKPIIAAIHGAALGGGLELAMACHIRIAAEDAKLGLPELNLGIIPGFAGTQRLPRYVGTAKALELIGSGEPISGKEALDLGLVSIGAKDEAEVIEKAKALAAKFAEKSPQTLASLLELLYSNKVYSEGSLKLEAKRFGEAFESEDAKEGIQAFLEKRKPQFKGE |
| 2 | HadI | Clostridium difficile | AAV40818.1 | MYTMGLDIGSTASKGVILKNGEDIVASETISSGTGTTGPSRVLEKLYGKTGLAREDIKKVVVTGYGRMNYSDADKQISELSCHARGVNFIIPETRTIIDIGGQDAKVLKLDNNGRLLNFLMNDKCAAGTGRFLDVMAKIIEVDVSELGSISMNSQNEVSISSTCTVFAESEVISHLSENAKIEDIVAGIHTSVAKRVSSLVKRIGVQRNVVMVGGVARNSGIVRAMAREINTEIIVPDIPQLTGALGAALYAFDEAKESQKEVKNI |
| 3 | HadBC | Clostridium difficile | AAV40819.1 | MSEKKEARVVINDLLAEQYANAFKAKEEGRPVGWSTSVFPQELAEVFDLNVLYPENQAAGVAAKKGSLELCEIAESKGYSIDLCAYARTNFGLLENGGCEALDMPAPDFLLCNNICNQVIKWYENISRELDIPLIMIDTTFNNEDEVTQSRIDYIKAQFEEAAIKQLEIISGKKFDPKKFEEVMKISAENGRLWKYSMSLPADSSPSPMNGFDLFTYMAVIVCARGKKETTEAFKLIIELEDNIMKTGKSSFRGEEKYRIMIEGIPCWPYIGYKMKTLAKFGVNIMTGSVPPHAWALQYEVNDLDGMAVAYSTMFNNVNLDRMTKYRVDSLVEGKCDGAFYHIMNRSCKLMSLIQYEMQRRAAEETGLPYAGFDGDQADPRAFTNAQFETRIQGLVEVMEERKKLNRGEI |
| 4 | | Clostridium difficile | AAV40820.1 | MEAILSKMKEVVENPNAAVKKYKSETGKKAIGCFPVYCPEEIIHAAGMLPVGIWGGQTELDLAKQYFPAFACSIMQSCLEYGLKGAYDELSGVIIPGMCDTLICLGQNWKSAVPHIKYISLVHPQNRKLEAGVKYLISEYKGVKRELEEICGYEIEEAKIHESIEVYNEHRKTMRDFVEVAYKHSNTIKPSIRSLVIKSGFFMRKEEHTELVKDLIAKLNAMPEEVCSGKKVLLTGILADSKDILDILEDNNISVVADDLAQETRQFRTDVPAGDDALERLARQWSNIEGCSLAYDPKKKRGSLIVDEVKKKDIDGVIFCMIMKFCDPEEYDYPLVRKDIEDSGIPTLYVEIDQQTQNNEQARTRIQTFAEMMSLA |

FIG. 9B

| SEQ ID | Gene designation | Organism | GENBANK reference | FASTA sequence |
|---|---|---|---|---|
| 5 | HgdC | Acidaminococcus fermentans | CAA42196.1 | MSIYTLGIDVGSTASKCIILKDGKEIVAKSLVAVGTGTSGPARSISEVLENAHMKKEDMA FTLATGYGRNSLEGIADKQMSELSCHAMGASFIWPNVHTVIDIGGQDVKIHVENGTMTN FQMNDKCAAGTGRFLDVMANILEVKVSDLAELGAKSTKRVAISSTCTVFAESEVISQLSK GTDKIDIIAGIHRSVASRVIGLANRVGIVKDVVNTGGVAQNYGVRGALEEGLGVEIKTSP LAQYNGALGAALYAYKKAAK |
| 6 | HdgAB | Acidaminococcus fermentans | CAA32465.1 | MPKTVSPGVQALRDVVEKVYRELREAKERGEKVGWSSSKFPCELAESFGLHVGYPENQAA GIAANRDGEVMCQAAEDIGYDNDICGYARISLAYAAGFRGANKMDKDGNYVINPHSGKQM KDANGKKVFDADGKPVIDPKTLKPFATTDNIYEIAALPEGEEKTRRQNALHKYRQMTMPM PDFVLCCNNICNCMTKWYEDIARRHNIPLIMIDVPYNEFDHVNEANVKYIRSQLDTAIRQ MEEITGKKFDEDKFEQCCQNANRTAKAWLKVCDYLQYKPAPFNGFDLFNHMADVVTARGR VEAAEAFELLAKELEQHVKEGTTTAPFKEQHRIMFEGIPCWPKLPNLFKPLKANGLNITG VVYAPAFGFVYNNLDELVKAYCKAPNSVSIEQGVAWREGLIRDNKVDGVLVHYNRSCKPW SGYMPEMQRRFTKDMGIPTAGFDGDQADPRNFNAAQYETRVQGLVEAMEANDEKKGK |
| 7 | | Acidaminococcus fermentans | CAA32466.1 | MAISALIEEFQKVSASPKTMLAKYKAQGKKAIGCLPYYVPEELVYAAGMVPMGVWGCNGK QEVRSKEYCASFYCTIAQQSLEMILLDGTLDGLDGIITPVLCDTLRPMSQNFKVAMKDKMP VIFLAHPQVRQNAAGKQFTYDAYSEVKGHLEEICGHEITNDAILDAIKVYNKSRAARREF CKLANEHPDLIPASVRATVLRAAYFMLKDEYTEKLEELNKELAAAPAGKFDGHKVVVSGI IYNMPGILKAMDDNKLAIAADDCAYESRSFAVDAPEDLDNGLQALAVQFSKQKNDVLLYD PEFAKNTRSEHVCNLVKESGAEGLIVFMMQFCDPEEMEYPDLKKALDAHHIPHVKIGVDQ MTRDFGQAQTALEAFFAESL |
| 8 | mdd | Streptococcus pyogenes M1 | AAK33797.1 | MDPNVITVTSYANIAIIKYWGKENQAKMIPSTSSISLTLENMFTTTSVSFLPDTATSDQF YINGILQNDEEHTKISAIIDQFRQPGQAFVKMETQNNMPTAAGLSSSSGLSALVKACDQ LFDTQLDQKALAQKAKFASGSSSRSFFGPVAAWDKDSGAIYKVETDLKMAMIMLVLNAAK KPISSREGMKLCRDTSTTFDQWVEQSAIDYQHMLTYLKTNNFEKVGQLTEANALAMHATT KTANPPFSYLTKESYQAMEAVKELRQEGFACYFTMDAGPNVKVLCLEKDLAQLAERLGKN YRIIVSKTKDLPDV |

FIG. 9C

| SEQ ID | Gene designation | Organism | GENBANK reference | FASTA sequence |
|---|---|---|---|---|
| 9 | mdd | Thioalkalimicrobium aerophilum AL3 | AHF01884.1 | MPTPNPRQVAFVQAVLATGKQACSSASTIKLEGKGHAPVNIALSKYWGKRDTILNLPQNG SVSISLPGLGTDTTLRPLASDSSQQVTAQDRISLNGQQLDAHQPFAHRLSQFLDLFRTAE VPFFEVITHNTVPTAAGLASSASGYAALVLALDDLFNWQLPATQLSLLARLGSGSASRSL FPGFAIWHAGOSEQGLDSFAEALDAPWPDFCVGLVEIDVAEKPVGSTAGMQQTTAACALY SAWPAQAERDKAVIINAIQQQDFSQLGATAEHNALSMHATMIASWPPLLYWQAESVIAMQ KVWALRQQGVEVYFTMDAGPNLKLLFLAAQKKAVSAAFSGLKVIEPFAKPDTQAAS |
| 10 | mdd | Streptococcus pneumoniae | CAR68209.1 | MDREPVTVRSYANIAIIKYWGKKKEKEMVPATSSISLTLENMYTETTLSPLPANVTADEF YINGQLQNEVEHAKMSKIIDRYRPAGEGFVRIDTQNNMPTAAGLSSSSSGLSALVKACNA YFKLGLDRSQLAQEAKFASGSSSRSFYGPLGAWDKDSGEIYPVETDLKLAMIMLVLEDKK KPISSRDGMKLCVETSTTFDDWVRQSEKDYQDMLIYLKENDFAKIGELTEKNALAMHATT KTASPAFSYLTDASYEAMDFVRQLREKGEACYFTMDAGPNVKVFCQEKDLEHLSEIFGHR YRLIVSKTKDLSQDDCC |
| 11 | mdd | Saccharomyces cerevisiae | CAA66158.1 | MTVYTASVTAPVNIATLKYWGKRDTKLNLPTNSSISVTLSQDDLRTLTSAATAPEFERDT LWLNGEPHSIDNERTQNCLRDLRQLRKEMESKDASLPTLSQWKLHIVSENNFPTAAGLAS SAAGFAALVSAIAKLYQLPQSTSEISRIARKGSGSACRSLFGGYVAWEMGKAEDGHDSMA VQIADSSDWPQMKACVLVVSDIKKDVSSTQGMQLTVATSELFKERIEHVVPKRFEVMRKA IVEKDFATFAKETMMDSNSFHATCLDSFPPIFYMNDTSKRIISWCHTINQFYGETIVAYT FDAGPNAVLYLAENESKLFAFIYKLFGSVPGWDKKFTTEQLEAFNHQFESSNFTARELD LELQKDVARVILTQVGSGPQETNESLIDAKTGLPKE |
| 12 | m3k | Thermoplasma acidophilum | CAC12426.1 | MTYRSIGSTAYPTIGVVLLGGIANPVTRTPLHTSAGIAYSDSCGSIRSETRIYADEATHI YFNGTESTDDNRSVRRVLDRYSSVFEEAFGTKTVSYSSQNFGILSGSSDAGAASIGAAIL GLKPDLDPHDVENDLRAVSESAGRSLFGGLTITWSDGFHAYTEKILDPEAFSGYSIVAFA FDYQRNPSDVIHQNIVRSDLYPARKKHADEHAHMIKEYAKTNDIKGIFDLAQEDTEEYHS ILRGVGVNVIRENMQKLISYLKLIRKDYWNAYIVTGGSNVYVAVESENADRLFSIENTFG SKKKMLRIVGGAWHRRPE |

FIG. 9D

| SEQ ID | Gene designation | Organism | GENBANK reference | FASTA sequence |
|---|---|---|---|---|
| 13 | Idi | Castellaniella defragrans | CBW30776.1 | MRFTLKTTAIVSAAALLAGFGPPPRAAELPPGRLATTEDYFAQQAKQAVTPDVMAQLAYM NYIDFISPFYSRGCSFEAWELKHTPQRVIKYSIAFYAYGLASVALIDPKLRALAGHDLDI AVSKMKCKRVWGDWEEDGFGTDPIEKENIMYKGHLNLMYGLYQLVTGSRRYEAEHAHLTR IIHDEIAANPFAGIVCEPDNYFVQCNSVAYLSLWVYDRLHGTDYRAATRAWLDFIQKDLI DPERGAFYLSYHPESGAVKPWISAYTTAWTLAMVHGMDPAFSERYYPRFKQTFVEVYDEG RKARVRETAGTDDADGGVGLASAFTLLLAREMGDQQLFDQLLNHLEPPAKPSIVSASLRY EHPGSLLFDELLFLAKVHAGFGALLRMPPPAAKLAGK |
| 14 | tcsD | Streptomyces kanamyceticus | ADU56239.1 | MSEPEHLDTVRKFVAQEVLGRETHLDSLADAPLALYERFAETGLMNWWVPEEHGGLGLGL EDSVRIVSELAYGDAGVAFTLFLPILTTSMVSWYGSAELKEKLLDPLVAHRGFCATLGSE HEAGSELAKISTVVRRDGEGLVLDGTKAFSTSTDFAQFLVVIARSAENPTRYLAVAVERD APGLRIDKRWDVIGLRASATYQVSFSDCHVPAGNALDGHGLRLLEIGLNASRILJAATAL GVARRIRDLCMEYAKTKSLKGAPLVNDAVFAGRLGQFEMQJEVMANQCLAAARTYDATAA RPDAARTLLRQGAQKSALTAKMFCGQTAWQJASTASEMFGGIGYTHDVPIGKLLRDVRHA SIIEGGDDVLRDLVFHRFVVPTAKRT |
| 15 | mdpJ | Aquincola tertiaricarbonis | AER12131.1 | MGNREPLAAAGQGTAYSGYRLRDLQNVAPTNLEILRTGPGTPMGEYMRRYWQPVCLSQEL TDVPKAIRILHEDLVAFRDRRGNVGVLHRKCAHRGASLEFGIVQERGIRCCYHGWHFDVD GSLLEAPAEPPDTKLKETVCQGAYPAFERNGLVFAYMGPADRRPEFPVFDGYVLPKGTRL IPFSNVFDCNWLQVYENQIDHYHTALLHNNIMTVAGVDAKLADGATLQGGFGEMPIIDWHP TDDNNGMIFTAGRRLSDDEVWIRISQMGLPNWMIQNAAIVAAAPQRHSGPAMSRWQVPVDD EHSIAFGWRHFNDEVDPEHRGREEECGVDKIDFLIGQTRHRPYEETQRVPGDYEAIVSQG PIALHGLEHPGRSDVGVVMCRSLLRDAVAGKAPPDPVRVKAGSTDGQTLPRYASDSRLRI RRRPSREADSDVIRKAAHQVFAIMKECDELPVVQRRPHVLRRLDEIEASL |
| 16 | phaJ | Aeromonas punctata | BAA21816.1 | MSAQSLEVGQKARLSKRFGAAEVAAFAALSEDFNPLHLDPAFAATTAFERPIVHGMLLAS LFSGLLGQQLPGKGSIYLGQSLSFKLPVFVGDEVTAEVEVTALREDKPIATLTRIFTQG GALAVTGEAVVKLP |
| 17 | MaoC | Escherichia coli | EIZ48549.1 | MLAAISKQWVRGAKVEEDRIHPFRKYFEELQPGDSLLTPRRTIMTEADIVNFACLSGDHFY AHMDKIAAAESIFGERVVHGYFVLSAAAGLFVDAGVGPVIANYGLESLRFIEPVKPGDTI QVRLTCKRKTLKKQRSAEEKPTGVVEWAVEVFNQHQTPVALYSILTLVARQHGDFVD |

FIG. 9E

| SEQ ID | Gene designation | Organism | GENBANK reference | FASTA sequence |
|---|---|---|---|---|
| 18 | AnlF | Streptomyces sp. CNH189 | AFY98994.1 | MEMAPGYVTSVLGTGSYLPERVVTNEEIEARVPGASAEWIAVRTAIVERRYAAPDEAASD LAVHAARAALDQAGILDADGIDFIIVATTTGDAPIPSTASLVQLALGARRAACFDVNIACT GFVTALSIARAYVALDPTTKVLVIGTDVWTRFIDFDNRATSVLFGDGAGAAVIGSVPHAP GDPERGLLKVELVSRGDAHELISMPAGGSRRPASVETVADGGHLLSMQGRGVRDFVLDNV PGLIAGLLKRSGHEPADVQHFVPHQANGRLVEELAGASGLVRADTHLPLRHSGNIGSASV PVALDAANRSGVLRDGDLVLLAGFGAGMAAGAALLRWTATEGGTR |
| 19 | OLS ST | Synechococcus PCC 7002 sulfotransferase domain | ACA99172.1 | SNASQSLSVKTKKQWQKPDHKNPNPIAFILSSPRSGSTLLRVMLAGHPGLYSPPELHLLPFET MGDRHQELGLSHLGEGLQRALMDLENLTPEASQAKVNQWVKANTPIADIYAYLQRQAEQR LLIDKSPSYGSDRHILDHSEILFDQAKYIHLVRHPYAVIESFTRLRMDKLLGAEQQNPYALAESIW RTSNRNILDLGRTVGADRYLQVIYEDLVRDPRKVLTNICDFLGVDFDEALLNPYSGDRLTDGLHQ QSMGVGDPNFLQHKTIDPALADKWRSITLPAALQLDTIQLAETFAYDLPQEPQLTPQTQ |
| 20 | CurM ST | Moorea producens 19L sulfotransferase domain | ACV42478.1 | SNASPTSLEIFATKSSPSGNSARPASVSSRLPGIIFILSSPRSGSTLLRVMLAGHSSLFSPPELHLLPF NTMKERQEQLNLSYLGEGLQKTFMEVKNLDATASQALIKDLESQNLSIQQVYGMILQENIAPRLL VDKSPTYAMEPTILERGEALFANSKYIYLVRHPYSVIESFVRMRMQKLVGLEENPYRVAEQVWA KSNQNILNFLSQLEPERQHQIRYEDLVKKPQQVLSQLCDFLNVPFEPELLQPYQGDRMTGGVHAA SLSISDPNFLKHNTIDESLADKWKTIQLPYPLKSETQRIASQLSYELPNLVTTPTNQQPQ |
| 21 | CurM TE | Moorea producens 19L thioesterase domain | ACV42478.1 | SNAMEEKFLEFGGNQICLCSWGSPEHPVVLCIHGILEQGLAWQEVALPLAAQGYRVAPDLFGHGR SSHLEMVTSYSSLTFLAQIDRVIQELPDQPLLLVGHSMGAMLATAIASVRPKKIKELILVELPLPAEESKK ESAVNQLTTCLDYLSSTPQHPIFPDVATAASRLRQAIPSLSEEFSYILAQRITQPNQGGVRWSWDAIIRT RSILGLNNLPGGRSQYLEMLKSIQVPTTLVYGDSSKLNRPEDLQQQKMTMTQAKRVFLSGGHNLHIDA AAALASLILTS |

FIG 9F

| SEQ ID | Gene designation | Organism | GENBANK reference | FASTA sequence |
|---|---|---|---|---|
| 22 | *ohyA* | *Elizabethkingia meningoseptica* | ACT54545.1 | MNPITSKFDKVLNASSEYGHVNHEPDSSKEQQRNTPQKSMPFSDQIGNYQRNKGIPVQSY<br>DNSKIYIIGSGIAGMSAAYYFIRDGHVPAKNITFLEQLHIDGGSLDGAGNPTDGYIIRGG<br>REMDMTYENLWDMFQDIPALEMPAPYSVLDEYRLINDNDSNYSKARLINNKGEIKDFSKF<br>GLNKMDQLAIIRLLLKNKEELDDLTIEDYFSESFLKSNFWTFWRTMFAFENWHSLLELKL<br>YMHRFLHAIDGLNDLSSLVFPKYNQYDTFVTPLRKFLQEKGVNIHLNTLVKDLDIHINTE<br>GKVVEGIITEQDGKEVKIPVGKNDYVIVTTGSMTEDTFYGNNKTAPIIGIDNSTSGQSAG<br>WKLWKNLAAKSEIFGKPEKFCSNIEKSAWESATLTCKPSALIDKLKEYSVNDPYSGKTVT<br>GGIITITDSNWLMSFTCNRQPHFPEQPDDVLVLWVYALFMDKEGNYIKKTMLECTGDEIL<br>AELCYHLGIEDQLENVQKNTIVRTAFMPYITSMFMPRAKGDRPRVVPEGCKNLGLVGQFV<br>ETNNDVVFTMESSVRTARIAVYKLLNLNKQVPDINPLQYDIRHLLKAAKTLNDDKPFVGE<br>GLLRKVLKGTYFEHVLPAGAAEEEEHESFIAEHVNKFREWVKGIRG |

FIG. 11

| Sample ID | Analyte | Mwt | Peak Retention Time (mins) | Peak Area @ 260nm (mAu) | Observed Mass (m/z) | | Comments |
|---|---|---|---|---|---|---|---|
| | | [g/mol] | [min] | [mAu] | Negative mode (M-H) | positive mode (M+H) | |
| 0.1 [mg/mL] crotonyl CoA as standard | Crotonyl-CoA | 835.6 | 5.374 | 1839.89 | 833.7 | 835.9 | |
| Biotransformation at 1 [h] time point | 3-hydroxybutanoyl-CoA | 853.6 | 4.531 | 10197.8 | 851.9 | 854 | Biotransformation undertaken at 1 [mM] substrate concentration. |
| | Crotonyl-CoA | 835.6 | 5.37 | 907.59 | 833.9 | 836 | (m/z) corresponds to desired product. |
| Standard only control 1 [h] time point | 3-hydroxybutanoyl-CoA | 853.6 | 4.529 | 10571.9 | 865.9 | 868.1 | |
| | Crotonyl-CoA | 835.6 | 5.37 | 9.207 | 833.9 | 836 | Weak signal in baseline noise of MS. |

FIG. 12

| Sample ID | Analyte | Mwt | Peak Retention Time | Peak Area @ 260nm | Observed Mass (m/z) | | Comments |
|---|---|---|---|---|---|---|---|
| | | [g/mol] | [min] | [mAu] | Negative mode (M-H) | Positive mode (M+H) | |
| 2 [mM] reference standard | 3-methyl-3-hydroxy pentanoyl-CoA methyl ester CoA | 881.2 | 5.148 | 8197.95 | 880 | 882 | methyl ester CoA impurity was formed during substrate preparation |
| | | 825.5 | 4.729 | 1922.02 | 823.9 | 826 | |
| Biotransformation at 1 [h] time point | 3-methyl-3-hydroxypentanoyl-CoA methyl ester CoA | 881.2 | 5.191 | 3600.47 | 880 | 882 | m/z corresponds to desired product |
| | | 825.5 | 4.75 | 869.84 | 823.9 | 826 | |
| | 3-methyl-pent-2-enoyl CoA | 863.2 | 6.618 | 295.12 | 861.9 | 864 | |
| Substrate only control at 1 [h] time point | 3-methyl-3-hydroxy pentanoyl CoA methyl ester CoA | 881.2 | 5.189 | 3791.53 | 880 | 882 | no peak/mass corresponding to product |
| | | 825.5 | 4.747 | 847.99 | 823.9 | 826 | |

FIG. 13

| Sample ID | Analyte | Mwt | Peak Retention Time (mins) | Peak Area @ 260nm (mAu) | Observed Mass (m/z) | | Comments |
|---|---|---|---|---|---|---|---|
| | | [g/mol] | [min] | [mAu] | Negative mode (M-H) | Positive mode (M+H) | |
| 2 [mM] reference standard | 4-methyl-3-hydroxy pentanoyl CoA | 881.2 | 5.343 | 9964.91 | 879.9 | 882 | |
| | methyl ester CoA | 825.5 | 4.691 | 5341.9 | 823.9 | 826 | Methyl ester CoA impurity was formed during substrate preparation |
| | CoA | 767.5 | 4.1 | 2482.42 | 765.9 | 768 | Background hydrolysis forming CoA |
| Biotransformation at 1 [h] time point | 4-methyl-3-hydroxy pentanoyl CoA | 881.2 | 5.394 | 4063.69 | 879.9 | 882 | |
| | methyl ester CoA | 825.5 | 4.721 | 2652.76 | 823.9 | 826 | |
| | CoA | 767.5 | 4.119 | 1132.55 | 765.9 | 768 | |
| | 4-methyl-pent-2-enoyl CoA | 863.2 | 6.58 | 940.49 | 862 | 864 | m/z corresponds to desired product |
| Substrate only control at 1 [h] time point | 4-methyl-3-hydroxy pentanoyl CoA | 881.2 | 5.419 | 2580.77 | 880 | 882 | no peak/mass corresponding to product |
| | methyl ester CoA | 825.5 | 4.741 | 1372.98 | 823.9 | 826 | |
| | CoA | 767.5 | 4.127 | 640.18 | 765.9 | 768 | |

SEQUENCE LISTING

```
<160> NUMBER OF SEQ ID NOS: 22

<210> SEQ ID NO 1
<211> LENGTH: 258
<212> TYPE: PRT
<213> ORGANISM: Bacillus subtilis

<400> SEQUENCE: 1

Met Asn Ala Ile Ser Leu Ala Val Asp Gln Phe Val Ala Val Leu Thr
1               5                   10                  15

Ile His Asn Pro Pro Ala Asn Ala Leu Ser Ser Arg Ile Leu Glu Glu
            20                  25                  30
```

Leu Ser Ser Cys Leu Asp Gln Cys Glu Thr Asp Ala Gly Val Arg Ser
            35                  40                  45

Ile Ile Ile His Gly Glu Gly Arg Phe Phe Ser Ala Gly Ala Asp Ile
 50                  55                  60

Lys Glu Phe Thr Ser Leu Lys Gly Asn Glu Asp Ser Ser Leu Leu Ala
 65                  70                  75                  80

Glu Arg Gly Gln Gln Leu Met Glu Arg Ile Glu Ser Phe Pro Lys Pro
                85                  90                  95

Ile Ile Ala Ala Ile His Gly Ala Ala Leu Gly Gly Leu Glu Leu
                100                 105                 110

Ala Met Ala Cys His Ile Arg Ile Ala Ala Glu Asp Ala Lys Leu Gly
            115                 120                 125

Leu Pro Glu Leu Asn Leu Gly Ile Ile Pro Gly Phe Ala Gly Thr Gln
            130                 135                 140

Arg Leu Pro Arg Tyr Val Gly Thr Ala Lys Ala Leu Glu Leu Ile Gly
145                 150                 155                 160

Ser Gly Glu Pro Ile Ser Gly Lys Glu Ala Leu Asp Leu Gly Leu Val
                165                 170                 175

Ser Ile Gly Ala Lys Asp Glu Ala Glu Val Ile Glu Lys Ala Lys Ala
            180                 185                 190

Leu Ala Ala Lys Phe Ala Glu Lys Ser Pro Gln Thr Leu Ala Ser Leu
            195                 200                 205

Leu Glu Leu Leu Tyr Ser Asn Lys Val Tyr Ser Tyr Glu Gly Ser Leu
            210                 215                 220

Lys Leu Glu Ala Lys Arg Phe Gly Glu Ala Phe Glu Ser Glu Asp Ala
225                 230                 235                 240

Lys Glu Gly Ile Gln Ala Phe Leu Glu Lys Arg Lys Pro Gln Phe Lys
                245                 250                 255

Gly Glu

<210> SEQ ID NO 2
<211> LENGTH: 266
<212> TYPE: PRT
<213> ORGANISM: Clostridium difficile

<400> SEQUENCE: 2

Met Tyr Thr Met Gly Leu Asp Ile Gly Ser Thr Ala Ser Lys Gly Val
 1               5                  10                  15

Ile Leu Lys Asn Gly Glu Asp Ile Val Ala Ser Glu Thr Ile Ser Ser
                20                  25                  30

Gly Thr Gly Thr Thr Gly Pro Ser Arg Val Leu Glu Lys Leu Tyr Gly
            35                  40                  45

Lys Thr Gly Leu Ala Arg Glu Asp Ile Lys Lys Val Val Thr Gly
 50                  55                  60

Tyr Gly Arg Met Asn Tyr Ser Asp Ala Asp Lys Gln Ile Ser Glu Leu
 65                  70                  75                  80

Ser Cys His Ala Arg Gly Val Asn Phe Ile Ile Pro Glu Thr Arg Thr
            85                  90                  95

Ile Ile Asp Ile Gly Gly Gln Asp Ala Lys Val Leu Lys Leu Asp Asn
            100                 105                 110

Asn Gly Arg Leu Leu Asn Phe Leu Met Asn Asp Lys Cys Ala Ala Gly
            115                 120                 125

Thr Gly Arg Phe Leu Asp Val Met Ala Lys Ile Ile Glu Val Asp Val
            130                 135                 140

```
Ser Glu Leu Gly Ser Ile Ser Met Asn Ser Gln Asn Glu Val Ser Ile
145                 150                 155                 160

Ser Ser Thr Cys Thr Val Phe Ala Glu Ser Glu Val Ile Ser His Leu
            165                 170                 175

Ser Glu Asn Ala Lys Ile Glu Asp Ile Val Ala Gly Ile His Thr Ser
        180                 185                 190

Val Ala Lys Arg Val Ser Ser Leu Val Lys Arg Ile Gly Val Gln Arg
    195                 200                 205

Asn Val Val Met Val Gly Gly Val Ala Arg Asn Ser Gly Ile Val Arg
210                 215                 220

Ala Met Ala Arg Glu Ile Asn Thr Glu Ile Ile Val Pro Asp Ile Pro
225                 230                 235                 240

Gln Leu Thr Gly Ala Leu Gly Ala Ala Leu Tyr Ala Phe Asp Glu Ala
                245                 250                 255

Lys Glu Ser Gln Lys Glu Val Lys Asn Ile
            260                 265

<210> SEQ ID NO 3
<211> LENGTH: 408
<212> TYPE: PRT
<213> ORGANISM: Clostridium difficile

<400> SEQUENCE: 3

Met Ser Glu Lys Lys Glu Ala Arg Val Val Ile Asn Asp Leu Leu Ala
1               5                   10                  15

Glu Gln Tyr Ala Asn Ala Phe Lys Ala Lys Glu Glu Gly Arg Pro Val
            20                  25                  30

Gly Trp Ser Thr Ser Val Phe Pro Gln Glu Leu Ala Glu Val Phe Asp
        35                  40                  45

Leu Asn Val Leu Tyr Pro Glu Asn Gln Ala Ala Gly Val Ala Ala Lys
    50                  55                  60

Lys Gly Ser Leu Glu Leu Cys Glu Ile Ala Glu Ser Lys Gly Tyr Ser
65                  70                  75                  80

Ile Asp Leu Cys Ala Tyr Ala Arg Thr Asn Phe Gly Leu Leu Glu Asn
                85                  90                  95

Gly Gly Cys Glu Ala Leu Asp Met Pro Ala Pro Asp Phe Leu Leu Cys
            100                 105                 110

Cys Asn Asn Ile Cys Asn Gln Val Ile Lys Trp Tyr Glu Asn Ile Ser
        115                 120                 125

Arg Glu Leu Asp Ile Pro Leu Ile Met Ile Asp Thr Thr Phe Asn Asn
    130                 135                 140

Glu Asp Glu Val Thr Gln Ser Arg Ile Asp Tyr Ile Lys Ala Gln Phe
145                 150                 155                 160

Glu Glu Ala Ile Lys Gln Leu Glu Ile Ile Ser Gly Lys Lys Phe Asp
                165                 170                 175

Pro Lys Lys Phe Glu Glu Val Met Lys Ile Ser Ala Glu Asn Gly Arg
            180                 185                 190

Leu Trp Lys Tyr Ser Met Ser Leu Pro Ala Asp Ser Pro Ser Pro
        195                 200                 205

Met Asn Gly Phe Asp Leu Phe Thr Tyr Met Ala Val Ile Val Cys Ala
    210                 215                 220

Arg Gly Lys Lys Glu Thr Thr Glu Ala Phe Lys Leu Leu Ile Glu Glu
225                 230                 235                 240

Leu Glu Asp Asn Met Lys Thr Gly Lys Ser Ser Phe Arg Gly Glu Glu
                245                 250                 255
```

```
Lys Tyr Arg Ile Met Met Glu Gly Ile Pro Cys Trp Pro Tyr Ile Gly
            260                 265                 270

Tyr Lys Met Lys Thr Leu Ala Lys Phe Gly Val Asn Met Thr Gly Ser
            275                 280                 285

Val Tyr Pro His Ala Trp Ala Leu Gln Tyr Glu Val Asn Asp Leu Asp
            290                 295                 300

Gly Met Ala Val Ala Tyr Ser Thr Met Phe Asn Asn Val Asn Leu Asp
305                 310                 315                 320

Arg Met Thr Lys Tyr Arg Val Asp Ser Leu Val Glu Gly Lys Cys Asp
            325                 330                 335

Gly Ala Phe Tyr His Met Asn Arg Ser Cys Lys Leu Met Ser Leu Ile
            340                 345                 350

Gln Tyr Glu Met Gln Arg Arg Ala Ala Glu Glu Thr Gly Leu Pro Tyr
            355                 360                 365

Ala Gly Phe Asp Gly Asp Gln Ala Asp Pro Arg Ala Phe Thr Asn Ala
            370                 375                 380

Gln Phe Glu Thr Arg Ile Gln Gly Leu Val Glu Val Met Glu Glu Arg
385                 390                 395                 400

Lys Lys Leu Asn Arg Gly Glu Ile
            405

<210> SEQ ID NO 4
<211> LENGTH: 375
<212> TYPE: PRT
<213> ORGANISM: Clostridium difficile

<400> SEQUENCE: 4

Met Glu Ala Ile Leu Ser Lys Met Lys Glu Val Val Glu Asn Pro Asn
1               5                   10                  15

Ala Ala Val Lys Lys Tyr Lys Ser Glu Thr Gly Lys Lys Ala Ile Gly
            20                  25                  30

Cys Phe Pro Val Tyr Cys Pro Glu Glu Ile Ile His Ala Ala Gly Met
            35                  40                  45

Leu Pro Val Gly Ile Trp Gly Gly Gln Thr Glu Leu Asp Leu Ala Lys
50                  55                  60

Gln Tyr Phe Pro Ala Phe Ala Cys Ser Ile Met Gln Ser Cys Leu Glu
65                  70                  75                  80

Tyr Gly Leu Lys Gly Ala Tyr Asp Glu Leu Ser Gly Val Ile Ile Pro
            85                  90                  95

Gly Met Cys Asp Thr Leu Ile Cys Leu Gly Gln Asn Trp Lys Ser Ala
            100                 105                 110

Val Pro His Ile Lys Tyr Ile Ser Leu Val His Pro Gln Asn Arg Lys
            115                 120                 125

Leu Glu Ala Gly Val Lys Tyr Leu Ile Ser Glu Tyr Lys Gly Val Lys
130                 135                 140

Arg Glu Leu Glu Glu Ile Cys Gly Tyr Glu Ile Glu Glu Ala Lys Ile
145                 150                 155                 160

His Glu Ser Ile Glu Val Tyr Asn Glu His Arg Lys Thr Met Arg Asp
            165                 170                 175

Phe Val Glu Val Ala Tyr Lys His Ser Asn Thr Ile Lys Pro Ser Ile
            180                 185                 190

Arg Ser Leu Val Ile Lys Ser Gly Phe Phe Met Arg Lys Glu Glu His
            195                 200                 205

Thr Glu Leu Val Lys Asp Leu Ile Ala Lys Leu Asn Ala Met Pro Glu
```

```
                 210                 215                 220

Glu Val Cys Ser Gly Lys Lys Val Leu Leu Thr Gly Ile Leu Ala Asp
225                 230                 235                 240

Ser Lys Asp Ile Leu Asp Ile Leu Glu Asp Asn Asn Ile Ser Val Val
                245                 250                 255

Ala Asp Asp Leu Ala Gln Glu Thr Arg Gln Phe Arg Thr Asp Val Pro
                260                 265                 270

Ala Gly Asp Asp Ala Leu Glu Arg Leu Ala Arg Gln Trp Ser Asn Ile
            275                 280                 285

Glu Gly Cys Ser Leu Ala Tyr Asp Pro Lys Lys Arg Gly Ser Leu
290                 295                 300

Ile Val Asp Glu Val Lys Lys Asp Ile Asp Gly Val Ile Phe Cys
305                 310                 315                 320

Met Met Lys Phe Cys Asp Pro Glu Glu Tyr Asp Tyr Pro Leu Val Arg
                325                 330                 335

Lys Asp Ile Glu Asp Ser Gly Ile Pro Thr Leu Tyr Val Glu Ile Asp
                340                 345                 350

Gln Gln Thr Gln Asn Asn Glu Gln Ala Arg Thr Arg Ile Gln Thr Phe
                355                 360                 365

Ala Glu Met Met Ser Leu Ala
                370                 375

<210> SEQ ID NO 5
<211> LENGTH: 260
<212> TYPE: PRT
<213> ORGANISM: Acidaminococcus fermentans

<400> SEQUENCE: 5

Met Ser Ile Tyr Thr Leu Gly Ile Asp Val Gly Ser Thr Ala Ser Lys
1               5                   10                  15

Cys Ile Ile Leu Lys Asp Gly Lys Glu Ile Val Ala Lys Ser Leu Val
                20                  25                  30

Ala Val Gly Thr Gly Thr Ser Gly Pro Ala Arg Ser Ile Ser Glu Val
            35                  40                  45

Leu Glu Asn Ala His Met Lys Lys Glu Asp Met Ala Phe Thr Leu Ala
        50                  55                  60

Thr Gly Tyr Gly Arg Asn Ser Leu Glu Gly Ile Ala Asp Lys Gln Met
65                  70                  75                  80

Ser Glu Leu Ser Cys His Ala Met Gly Ala Ser Phe Ile Trp Pro Asn
                85                  90                  95

Val His Thr Val Ile Asp Ile Gly Gly Gln Asp Val Lys Val Ile His
                100                 105                 110

Val Glu Asn Gly Thr Met Thr Asn Phe Gln Met Asn Asp Lys Cys Ala
            115                 120                 125

Ala Gly Thr Gly Arg Phe Leu Asp Val Met Ala Asn Ile Leu Glu Val
        130                 135                 140

Lys Val Ser Asp Leu Ala Glu Leu Gly Ala Lys Ser Thr Lys Arg Val
145                 150                 155                 160

Ala Ile Ser Ser Thr Cys Thr Val Phe Ala Glu Ser Glu Val Ile Ser
                165                 170                 175

Gln Leu Ser Lys Gly Thr Asp Lys Ile Asp Ile Ile Ala Gly Ile His
            180                 185                 190

Arg Ser Val Ala Ser Arg Val Ile Gly Leu Ala Asn Arg Val Gly Ile
        195                 200                 205
```

```
Val Lys Asp Val Val Met Thr Gly Gly Val Ala Gln Asn Tyr Gly Val
    210                 215                 220

Arg Gly Ala Leu Glu Glu Gly Leu Gly Val Glu Ile Lys Thr Ser Pro
225                 230                 235                 240

Leu Ala Gln Tyr Asn Gly Ala Leu Gly Ala Ala Leu Tyr Ala Tyr Lys
                245                 250                 255

Lys Ala Ala Lys
            260

<210> SEQ ID NO 6
<211> LENGTH: 477
<212> TYPE: PRT
<213> ORGANISM: Acidaminococcus fermentans

<400> SEQUENCE: 6

Met Pro Lys Thr Val Ser Pro Gly Val Gln Ala Leu Arg Asp Val Val
1               5                   10                  15

Glu Lys Val Tyr Arg Glu Leu Arg Glu Ala Lys Glu Arg Gly Glu Lys
            20                  25                  30

Val Gly Trp Ser Ser Ser Lys Phe Pro Cys Glu Leu Ala Glu Ser Phe
        35                  40                  45

Gly Leu His Val Gly Tyr Pro Glu Asn Gln Ala Ala Gly Ile Ala Ala
    50                  55                  60

Asn Arg Asp Gly Glu Val Met Cys Gln Ala Ala Glu Asp Ile Gly Tyr
65                  70                  75                  80

Asp Asn Asp Ile Cys Gly Tyr Ala Arg Ile Ser Leu Ala Tyr Ala Ala
                85                  90                  95

Gly Phe Arg Gly Ala Asn Lys Met Asp Lys Asp Gly Asn Tyr Val Ile
            100                 105                 110

Asn Pro His Ser Gly Lys Gln Met Lys Asp Ala Asn Gly Lys Lys Val
        115                 120                 125

Phe Asp Ala Asp Gly Lys Pro Val Ile Asp Pro Lys Thr Leu Lys Pro
130                 135                 140

Phe Ala Thr Thr Asp Asn Ile Tyr Glu Ile Ala Ala Leu Pro Glu Gly
145                 150                 155                 160

Glu Glu Lys Thr Arg Arg Gln Asn Ala Leu His Lys Tyr Arg Gln Met
                165                 170                 175

Thr Met Pro Met Pro Asp Phe Val Leu Cys Cys Asn Asn Ile Cys Asn
            180                 185                 190

Cys Met Thr Lys Trp Tyr Glu Asp Ile Ala Arg Arg His Asn Ile Pro
        195                 200                 205

Leu Ile Met Ile Asp Val Pro Tyr Asn Glu Phe Asp His Val Asn Glu
210                 215                 220

Ala Asn Val Lys Tyr Ile Arg Ser Gln Leu Asp Thr Ala Ile Arg Gln
225                 230                 235                 240

Met Glu Glu Ile Thr Gly Lys Lys Phe Asp Glu Asp Lys Phe Glu Gln
                245                 250                 255

Cys Cys Gln Asn Ala Asn Arg Thr Ala Lys Ala Trp Leu Lys Val Cys
            260                 265                 270

Asp Tyr Leu Gln Tyr Lys Pro Ala Pro Phe Asn Gly Phe Asp Leu Phe
        275                 280                 285

Asn His Met Ala Asp Val Val Thr Ala Arg Gly Arg Val Glu Ala Ala
    290                 295                 300

Glu Ala Phe Glu Leu Leu Ala Lys Glu Leu Glu Gln His Val Lys Glu
305                 310                 315                 320
```

```
Gly Thr Thr Thr Ala Pro Phe Lys Glu Gln His Arg Ile Met Phe Glu
                325                 330                 335

Gly Ile Pro Cys Trp Pro Lys Leu Pro Asn Leu Phe Lys Pro Leu Lys
                340                 345                 350

Ala Asn Gly Leu Asn Ile Thr Gly Val Val Tyr Ala Pro Ala Phe Gly
                355                 360                 365

Phe Val Tyr Asn Asn Leu Asp Glu Leu Val Lys Ala Tyr Cys Lys Ala
                370                 375                 380

Pro Asn Ser Val Ser Ile Glu Gln Gly Val Ala Trp Arg Glu Gly Leu
385                 390                 395                 400

Ile Arg Asp Asn Lys Val Asp Gly Val Leu Val His Tyr Asn Arg Ser
                405                 410                 415

Cys Lys Pro Trp Ser Gly Tyr Met Pro Glu Met Gln Arg Arg Phe Thr
                420                 425                 430

Lys Asp Met Gly Ile Pro Thr Ala Gly Phe Asp Gly Asp Gln Ala Asp
                435                 440                 445

Pro Arg Asn Phe Asn Ala Ala Gln Tyr Glu Thr Arg Val Gln Gly Leu
        450                 455                 460

Val Glu Ala Met Glu Ala Asn Asp Glu Lys Lys Gly Lys
465                 470                 475

<210> SEQ ID NO 7
<211> LENGTH: 379
<212> TYPE: PRT
<213> ORGANISM: Acidaminococcus fermentans

<400> SEQUENCE: 7

Met Ala Ile Ser Ala Leu Ile Glu Glu Phe Gln Lys Val Ser Ala Ser
1               5                   10                  15

Pro Lys Thr Met Leu Ala Lys Tyr Lys Ala Gln Gly Lys Lys Ala Ile
                20                  25                  30

Gly Cys Leu Pro Tyr Tyr Val Pro Glu Glu Leu Val Tyr Ala Ala Gly
                35                  40                  45

Met Val Pro Met Gly Val Trp Gly Cys Asn Gly Lys Gln Glu Val Arg
        50                  55                  60

Ser Lys Glu Tyr Cys Ala Ser Phe Tyr Cys Thr Ile Ala Gln Gln Ser
65                  70                  75                  80

Leu Glu Met Leu Leu Asp Gly Thr Leu Asp Gly Leu Asp Gly Ile Ile
                85                  90                  95

Thr Pro Val Leu Cys Asp Thr Leu Arg Pro Met Ser Gln Asn Phe Lys
                100                 105                 110

Val Ala Met Lys Asp Lys Met Pro Val Ile Phe Leu Ala His Pro Gln
                115                 120                 125

Val Arg Gln Asn Ala Ala Gly Lys Gln Phe Thr Tyr Asp Ala Tyr Ser
        130                 135                 140

Glu Val Lys Gly His Leu Glu Glu Ile Cys Gly His Glu Ile Thr Asn
145                 150                 155                 160

Asp Ala Ile Leu Asp Ala Ile Lys Val Tyr Asn Lys Ser Arg Ala Ala
                165                 170                 175

Arg Arg Glu Phe Cys Lys Leu Ala Asn Glu His Pro Asp Leu Ile Pro
                180                 185                 190

Ala Ser Val Arg Ala Thr Val Leu Arg Ala Ala Tyr Phe Met Leu Lys
                195                 200                 205

Asp Glu Tyr Thr Glu Lys Leu Glu Glu Leu Asn Lys Glu Leu Ala Ala
```

```
            210                 215                 220
Ala Pro Ala Gly Lys Phe Asp Gly His Lys Val Val Ser Gly Ile
225                 230                 235                 240

Ile Tyr Asn Met Pro Gly Ile Leu Lys Ala Met Asp Asn Lys Leu
                245                 250                 255

Ala Ile Ala Ala Asp Asp Cys Ala Tyr Glu Ser Arg Ser Phe Ala Val
                260                 265                 270

Asp Ala Pro Glu Asp Leu Asp Asn Gly Leu Gln Ala Leu Ala Val Gln
                275                 280                 285

Phe Ser Lys Gln Lys Asn Asp Val Leu Leu Tyr Asp Pro Glu Phe Ala
            290                 295                 300

Lys Asn Thr Arg Ser Glu His Val Cys Asn Leu Val Lys Glu Ser Gly
305                 310                 315                 320

Ala Glu Gly Leu Ile Val Phe Met Met Gln Phe Cys Asp Pro Glu Glu
                325                 330                 335

Met Glu Tyr Pro Asp Leu Lys Lys Ala Leu Asp Ala His His Ile Pro
                340                 345                 350

His Val Lys Ile Gly Val Asp Gln Met Thr Arg Asp Phe Gly Gln Ala
            355                 360                 365

Gln Thr Ala Leu Glu Ala Phe Ala Glu Ser Leu
            370                 375

<210> SEQ ID NO 8
<211> LENGTH: 314
<212> TYPE: PRT
<213> ORGANISM: Streptococcus pyogenes M1

<400> SEQUENCE: 8

Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
                20                  25                  30

Ser Ser Ile Ser Leu Thr Leu Glu Asn Met Phe Thr Thr Thr Ser Val
            35                  40                  45

Ser Phe Leu Pro Asp Thr Ala Thr Ser Asp Gln Phe Tyr Ile Asn Gly
        50                  55                  60

Ile Leu Gln Asn Asp Glu Glu His Thr Lys Ile Ser Ala Ile Ile Asp
65                  70                  75                  80

Gln Phe Arg Gln Pro Gly Gln Ala Phe Val Lys Met Glu Thr Gln Asn
                85                  90                  95

Asn Met Pro Thr Ala Ala Gly Leu Ser Ser Ser Ser Gly Leu Ser
                100                 105                 110

Ala Leu Val Lys Ala Cys Asp Gln Leu Phe Asp Thr Gln Leu Asp Gln
            115                 120                 125

Lys Ala Leu Ala Gln Lys Ala Lys Phe Ala Ser Gly Ser Ser Arg
        130                 135                 140

Ser Phe Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
                165                 170                 175

Asn Ala Ala Lys Lys Pro Ile Ser Ser Arg Glu Gly Met Lys Leu Cys
                180                 185                 190

Arg Asp Thr Ser Thr Thr Phe Asp Gln Trp Val Glu Gln Ser Ala Ile
            195                 200                 205
```

-continued

```
Asp Tyr Gln His Met Leu Thr Tyr Leu Lys Thr Asn Asn Phe Glu Lys
    210                 215                 220
Val Gly Gln Leu Thr Glu Ala Asn Ala Leu Ala Met His Ala Thr Thr
225                 230                 235                 240
Lys Thr Ala Asn Pro Pro Phe Ser Tyr Leu Thr Lys Glu Ser Tyr Gln
                245                 250                 255
Ala Met Glu Ala Val Lys Glu Leu Arg Gln Glu Gly Phe Ala Cys Tyr
            260                 265                 270
Phe Thr Met Asp Ala Gly Pro Asn Val Lys Val Leu Cys Leu Glu Lys
        275                 280                 285
Asp Leu Ala Gln Leu Ala Glu Arg Leu Gly Lys Asn Tyr Arg Ile Ile
    290                 295                 300
Val Ser Lys Thr Lys Asp Leu Pro Asp Val
305                 310

<210> SEQ ID NO 9
<211> LENGTH: 356
<212> TYPE: PRT
<213> ORGANISM: Thioalkalimicrobium aerophilum AL3

<400> SEQUENCE: 9

Met Pro Thr Pro Asn Pro Arg Gln Val Ala Phe Val Gln Ala Val Leu
1               5                   10                  15
Ala Thr Gly Lys Gln Ala Cys Ser Ser Ala Ser Thr Ile Lys Leu Glu
            20                  25                  30
Gly Lys Gly His Ala Pro Val Asn Ile Ala Leu Ser Lys Tyr Trp Gly
        35                  40                  45
Lys Arg Asp Thr Ile Leu Asn Leu Pro Gln Asn Gly Ser Val Ser Ile
    50                  55                  60
Ser Leu Pro Gly Leu Gly Thr Asp Thr Thr Leu Arg Pro Leu Ala Ser
65                  70                  75                  80
Asp Ser Ser Gln Gln Val Thr Ala Gln Asp Arg Ile Ser Leu Asn Gly
                85                  90                  95
Gln Gln Leu Asp Ala His Gln Pro Phe Ala His Arg Leu Ser Gln Phe
            100                 105                 110
Leu Asp Leu Phe Arg Thr Ala Glu Val Pro Phe Phe Glu Val Ile Thr
        115                 120                 125
His Asn Thr Val Pro Thr Ala Ala Gly Leu Ala Ser Ser Ala Ser Gly
    130                 135                 140
Tyr Ala Ala Leu Val Leu Ala Leu Asp Asp Leu Phe Asn Trp Gln Leu
145                 150                 155                 160
Pro Ala Thr Gln Leu Ser Leu Leu Ala Arg Leu Gly Ser Gly Ser Ala
                165                 170                 175
Ser Arg Ser Leu Phe Pro Gly Phe Ala Ile Trp His Ala Gly Gln Ser
            180                 185                 190
Glu Gln Gly Leu Asp Ser Phe Ala Glu Ala Leu Asp Ala Pro Trp Pro
        195                 200                 205
Asp Phe Cys Val Gly Leu Val Glu Ile Asp Val Ala Glu Lys Pro Val
    210                 215                 220
Gly Ser Thr Ala Gly Met Gln Gln Thr Thr Ala Ala Cys Ala Leu Tyr
225                 230                 235                 240
Ser Ala Trp Pro Ala Gln Ala Glu Arg Asp Lys Ala Val Ile Ile Asn
                245                 250                 255
Ala Ile Gln Gln Gln Asp Phe Ser Gln Leu Gly Ala Thr Ala Glu His
            260                 265                 270
```

Asn Ala Leu Ser Met His Ala Thr Met Ile Ala Ser Trp Pro Pro Leu
            275                 280                 285

Leu Tyr Trp Gln Ala Glu Ser Val Ile Ala Met Gln Lys Val Trp Ala
        290                 295                 300

Leu Arg Gln Gln Gly Val Glu Val Tyr Phe Thr Met Asp Ala Gly Pro
305                 310                 315                 320

Asn Leu Lys Leu Leu Phe Leu Ala Ala Gln Lys Lys Ala Val Ser Ala
            325                 330                 335

Ala Phe Ser Gly Leu Lys Val Ile Glu Pro Phe Ala Lys Pro Asp Thr
            340                 345                 350

Gln Ala Ala Ser
            355

<210> SEQ ID NO 10
<211> LENGTH: 317
<212> TYPE: PRT
<213> ORGANISM: Streptococcus pneumoniae

<400> SEQUENCE: 10

Met Asp Arg Glu Pro Val Thr Val Arg Ser Tyr Ala Asn Ile Ala Ile
1               5                   10                  15

Ile Lys Tyr Trp Gly Lys Lys Glu Lys Glu Met Val Pro Ala Thr
            20                  25                  30

Ser Ser Ile Ser Leu Thr Leu Glu Asn Met Tyr Thr Glu Thr Thr Leu
            35                  40                  45

Ser Pro Leu Pro Ala Asn Val Thr Ala Asp Glu Phe Tyr Ile Asn Gly
        50                  55                  60

Gln Leu Gln Asn Glu Val Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asp Arg
            115                 120                 125

Ser Gln Leu Ala Gln Glu Ala Lys Phe Ala Ser Gly Ser Ser Ser Arg
        130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Ile Tyr Leu Lys Glu Asn Asp Phe Ala Lys
    210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys

```
                    275                 280                 285
Asp Leu Glu His Leu Ser Glu Ile Phe Gly His Arg Tyr Arg Leu Ile
        290                 295                 300

Val Ser Lys Thr Lys Asp Leu Ser Gln Asp Asp Cys Cys
305                 310                 315

<210> SEQ ID NO 11
<211> LENGTH: 396
<212> TYPE: PRT
<213> ORGANISM: Saccharomyces cerevisiae

<400> SEQUENCE: 11

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ala Ala Gly Phe Ala Ala Leu
        115                 120                 125

Val Ser Ala Ile Ala Lys Leu Tyr Gln Leu Pro Gln Ser Thr Ser Glu
    130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
    210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
    290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335
```

Phe Thr Thr Glu Gln Leu Glu Ala Phe Asn His Gln Phe Glu Ser Ser
                340                 345                 350

Asn Phe Thr Ala Arg Glu Leu Asp Leu Glu Leu Gln Lys Asp Val Ala
    355                 360                 365

Arg Val Ile Leu Thr Gln Val Gly Ser Gly Pro Gln Glu Thr Asn Glu
370                 375                 380

Ser Leu Ile Asp Ala Lys Thr Gly Leu Pro Lys Glu
385                 390                 395

<210> SEQ ID NO 12
<211> LENGTH: 318
<212> TYPE: PRT
<213> ORGANISM: Thermoplasma acidophilum

<400> SEQUENCE: 12

Met Thr Tyr Arg Ser Ile Gly Ser Thr Ala Tyr Pro Thr Ile Gly Val
1               5                   10                  15

Val Leu Leu Gly Gly Ile Ala Asn Pro Val Thr Arg Thr Pro Leu His
            20                  25                  30

Thr Ser Ala Gly Ile Ala Tyr Ser Asp Ser Cys Gly Ser Ile Arg Ser
        35                  40                  45

Glu Thr Arg Ile Tyr Ala Asp Glu Ala Thr His Ile Tyr Phe Asn Gly
    50                  55                  60

Thr Glu Ser Thr Asp Asp Asn Arg Ser Val Arg Arg Val Leu Asp Arg
65                  70                  75                  80

Tyr Ser Ser Val Phe Glu Glu Ala Phe Gly Thr Lys Thr Val Ser Tyr
                85                  90                  95

Ser Ser Gln Asn Phe Gly Ile Leu Ser Gly Ser Ser Asp Ala Gly Ala
            100                 105                 110

Ala Ser Ile Gly Ala Ala Ile Leu Gly Leu Lys Pro Asp Leu Asp Pro
        115                 120                 125

His Asp Val Glu Asn Asp Leu Arg Ala Val Ser Glu Ser Ala Gly Arg
    130                 135                 140

Ser Leu Phe Gly Gly Leu Thr Ile Thr Trp Ser Asp Gly Phe His Ala
145                 150                 155                 160

Tyr Thr Glu Lys Ile Leu Asp Pro Glu Ala Phe Ser Gly Tyr Ser Ile
                165                 170                 175

Val Ala Phe Ala Phe Asp Tyr Gln Arg Asn Pro Ser Val Ile His
            180                 185                 190

Gln Asn Ile Val Arg Ser Asp Leu Tyr Pro Ala Arg Lys Lys His Ala
        195                 200                 205

Asp Glu His Ala His Met Ile Lys Glu Tyr Ala Lys Thr Asn Asp Ile
    210                 215                 220

Lys Gly Ile Phe Asp Leu Ala Gln Glu Asp Thr Glu Glu Tyr His Ser
225                 230                 235                 240

Ile Leu Arg Gly Val Gly Val Asn Val Ile Arg Glu Asn Met Gln Lys
                245                 250                 255

Leu Ile Ser Tyr Leu Lys Leu Ile Arg Lys Asp Tyr Trp Asn Ala Tyr
            260                 265                 270

Ile Val Thr Gly Gly Ser Asn Val Tyr Val Ala Val Glu Ser Glu Asn
        275                 280                 285

Ala Asp Arg Leu Phe Ser Ile Glu Asn Thr Phe Gly Ser Lys Lys Lys
    290                 295                 300

Met Leu Arg Ile Val Gly Gly Ala Trp His Arg Arg Pro Glu
305                 310                 315

<210> SEQ ID NO 13
<211> LENGTH: 397
<212> TYPE: PRT
<213> ORGANISM: Castellaniella defragrans

<400> SEQUENCE: 13

| | | | | | | | | | | | | | | | |
|---|---|---|---|---|---|---|---|---|---|---|---|---|---|---|---|
| Met | Arg | Phe | Thr | Leu | Lys | Thr | Thr | Ala | Ile | Val | Ser | Ala | Ala | Ala | Leu |
| 1 | | | | 5 | | | | | 10 | | | | | 15 | |
| Leu | Ala | Gly | Phe | Gly | Pro | Pro | Arg | Ala | Ala | Glu | Leu | Pro | Pro | Gly | |
| | | | 20 | | | | | 25 | | | | | 30 | | |
| Arg | Leu | Ala | Thr | Thr | Glu | Asp | Tyr | Phe | Ala | Gln | Gln | Ala | Lys | Gln | Ala |
| | | | 35 | | | | | 40 | | | | | 45 | | |
| Val | Thr | Pro | Asp | Val | Met | Ala | Gln | Leu | Ala | Tyr | Met | Asn | Tyr | Ile | Asp |
| | 50 | | | | | 55 | | | | | 60 | | | | |
| Phe | Ile | Ser | Pro | Phe | Tyr | Ser | Arg | Gly | Cys | Ser | Phe | Glu | Ala | Trp | Glu |
| 65 | | | | | 70 | | | | 75 | | | | | | 80 |
| Leu | Lys | His | Thr | Pro | Gln | Arg | Val | Ile | Lys | Tyr | Ser | Ile | Ala | Phe | Tyr |
| | | | | 85 | | | | | 90 | | | | | 95 | |
| Ala | Tyr | Gly | Leu | Ala | Ser | Val | Ala | Leu | Ile | Asp | Pro | Lys | Leu | Arg | Ala |
| | | | 100 | | | | | 105 | | | | | 110 | | |
| Leu | Ala | Gly | His | Asp | Leu | Asp | Ile | Ala | Val | Ser | Lys | Met | Lys | Cys | Lys |
| | | | 115 | | | | | 120 | | | | | 125 | | |
| Arg | Val | Trp | Gly | Asp | Trp | Glu | Glu | Asp | Gly | Phe | Gly | Thr | Asp | Pro | Ile |
| | | | 130 | | | | | 135 | | | | | 140 | | |
| Glu | Lys | Glu | Asn | Ile | Met | Tyr | Lys | Gly | His | Leu | Asn | Leu | Met | Tyr | Gly |
| 145 | | | | | 150 | | | | | 155 | | | | | 160 |
| Leu | Tyr | Gln | Leu | Val | Thr | Gly | Ser | Arg | Arg | Tyr | Glu | Ala | Glu | His | Ala |
| | | | | 165 | | | | | 170 | | | | | 175 | |
| His | Leu | Thr | Arg | Ile | Ile | His | Asp | Glu | Ile | Ala | Ala | Asn | Pro | Phe | Ala |
| | | | 180 | | | | | 185 | | | | | 190 | | |
| Gly | Ile | Val | Cys | Glu | Pro | Asp | Asn | Tyr | Phe | Val | Gln | Cys | Asn | Ser | Val |
| | | | 195 | | | | | 200 | | | | | 205 | | |
| Ala | Tyr | Leu | Ser | Leu | Trp | Val | Tyr | Asp | Arg | Leu | His | Gly | Thr | Asp | Tyr |
| | | | 210 | | | | | 215 | | | | | 220 | | |
| Arg | Ala | Ala | Thr | Arg | Ala | Trp | Leu | Asp | Phe | Ile | Gln | Lys | Asp | Leu | Ile |
| 225 | | | | | 230 | | | | | 235 | | | | | 240 |
| Asp | Pro | Glu | Arg | Gly | Ala | Phe | Tyr | Leu | Ser | Tyr | His | Pro | Glu | Ser | Gly |
| | | | | 245 | | | | | 250 | | | | | 255 | |
| Ala | Val | Lys | Pro | Trp | Ile | Ser | Ala | Tyr | Thr | Thr | Ala | Trp | Thr | Leu | Ala |
| | | | 260 | | | | | 265 | | | | | 270 | | |
| Met | Val | His | Gly | Met | Asp | Pro | Ala | Phe | Ser | Glu | Arg | Tyr | Tyr | Pro | Arg |
| | | | 275 | | | | | 280 | | | | | 285 | | |
| Phe | Lys | Gln | Thr | Phe | Val | Glu | Val | Tyr | Asp | Glu | Gly | Arg | Lys | Ala | Arg |
| | | | 290 | | | | | 295 | | | | | 300 | | |
| Val | Arg | Glu | Thr | Ala | Gly | Thr | Asp | Asp | Ala | Asp | Gly | Val | Gly | Leu | |
| 305 | | | | | 310 | | | | | 315 | | | | | 320 |
| Ala | Ser | Ala | Phe | Thr | Leu | Leu | Leu | Ala | Arg | Glu | Met | Gly | Asp | Gln | Gln |
| | | | | 325 | | | | | 330 | | | | | 335 | |
| Leu | Phe | Asp | Gln | Leu | Leu | Asn | His | Leu | Glu | Pro | Pro | Ala | Lys | Pro | Ser |
| | | | 340 | | | | | 345 | | | | | 350 | | |
| Ile | Val | Ser | Ala | Ser | Leu | Arg | Tyr | Glu | His | Pro | Gly | Ser | Leu | Leu | Phe |
| | | | 355 | | | | | 360 | | | | | 365 | | |
| Asp | Glu | Leu | Leu | Phe | Leu | Ala | Lys | Val | His | Ala | Gly | Phe | Gly | Ala | Leu |

Leu Arg Met Pro Pro Ala Ala Lys Leu Ala Gly Lys
385                 390                 395

<210> SEQ ID NO 14
<211> LENGTH: 386
<212> TYPE: PRT
<213> ORGANISM: Streptomyces kanamyceticus

<400> SEQUENCE: 14

Met Ser Glu Pro Glu His Leu Asp Thr Val Arg Lys Phe Val Ala Gln
1               5                   10                  15

Glu Val Leu Gly Arg Glu Thr His Leu Asp Ser Leu Ala Asp Ala Pro
            20                  25                  30

Leu Ala Leu Tyr Glu Arg Phe Ala Glu Thr Gly Leu Met Asn Trp Trp
        35                  40                  45

Val Pro Glu Glu His Gly Gly Leu Gly Leu Gly Leu Glu Asp Ser Val
    50                  55                  60

Arg Ile Val Ser Glu Leu Ala Tyr Gly Asp Ala Gly Val Ala Phe Thr
65                  70                  75                  80

Leu Phe Leu Pro Ile Leu Thr Thr Ser Met Val Ser Trp Tyr Gly Ser
                85                  90                  95

Ala Glu Leu Lys Glu Lys Leu Leu Asp Pro Leu Val Ala His Arg Gly
            100                 105                 110

Phe Cys Ala Thr Leu Gly Ser Glu His Glu Ala Gly Ser Glu Leu Ala
        115                 120                 125

Lys Ile Ser Thr Val Val Arg Arg Asp Gly Glu Gly Leu Val Leu Asp
    130                 135                 140

Gly Thr Lys Ala Phe Ser Thr Ser Thr Asp Phe Ala Gln Phe Leu Val
145                 150                 155                 160

Val Ile Ala Arg Ser Ala Glu Asn Pro Thr Arg Tyr Leu Ala Val Ala
                165                 170                 175

Val Glu Arg Asp Ala Pro Gly Leu Arg Ile Asp Lys Arg Trp Asp Val
            180                 185                 190

Ile Gly Leu Arg Ala Ser Ala Thr Tyr Gln Val Ser Phe Ser Asp Cys
        195                 200                 205

His Val Pro Ala Gly Asn Ala Leu Asp Gly His Gly Leu Arg Leu Leu
    210                 215                 220

Glu Ile Gly Leu Asn Ala Ser Arg Ile Leu Ile Ala Ala Thr Ala Leu
225                 230                 235                 240

Gly Val Ala Arg Arg Ile Arg Asp Leu Cys Met Glu Tyr Ala Lys Thr
                245                 250                 255

Lys Ser Leu Lys Gly Ala Pro Leu Val Asn Asp Ala Val Phe Ala Gly
            260                 265                 270

Arg Leu Gly Gln Phe Glu Met Gln Ile Glu Val Met Ala Asn Gln Cys
        275                 280                 285

Leu Ala Ala Ala Arg Thr Tyr Asp Ala Thr Ala Ala Arg Pro Asp Ala
    290                 295                 300

Ala Arg Thr Leu Leu Arg Gln Gly Ala Gln Lys Ser Ala Leu Thr Ala
305                 310                 315                 320

Lys Met Phe Cys Gly Gln Thr Ala Trp Gln Ile Ala Ser Thr Ala Ser
                325                 330                 335

Glu Met Phe Gly Gly Ile Gly Tyr Thr His Asp Val Pro Ile Gly Lys
            340                 345                 350

```
Leu Leu Arg Asp Val Arg His Ala Ser Ile Ile Glu Gly Gly Asp Asp
            355                 360                 365

Val Leu Arg Asp Leu Val Phe His Arg Phe Val Val Pro Thr Ala Lys
    370                 375                 380

Arg Thr
385

<210> SEQ ID NO 15
<211> LENGTH: 470
<212> TYPE: PRT
<213> ORGANISM: Aquincola tertiaricarbonis

<400> SEQUENCE: 15

Met Gly Asn Arg Glu Pro Leu Ala Ala Gly Gln Gly Thr Ala Tyr
1               5                  10                  15

Ser Gly Tyr Arg Leu Arg Asp Leu Gln Asn Val Ala Pro Thr Asn Leu
            20                  25                  30

Glu Ile Leu Arg Thr Gly Pro Gly Thr Pro Met Gly Glu Tyr Met Arg
        35                  40                  45

Arg Tyr Trp Gln Pro Val Cys Leu Ser Gln Glu Leu Thr Asp Val Pro
    50                  55                  60

Lys Ala Ile Arg Ile Leu His Glu Asp Leu Val Ala Phe Arg Asp Arg
65                  70                  75                  80

Arg Gly Asn Val Gly Val Leu His Arg Lys Cys Ala His Arg Gly Ala
                85                  90                  95

Ser Leu Glu Phe Gly Ile Val Gln Glu Arg Gly Ile Arg Cys Cys Tyr
            100                 105                 110

His Gly Trp His Phe Asp Val Asp Gly Ser Leu Leu Glu Ala Pro Ala
        115                 120                 125

Glu Pro Pro Asp Thr Lys Leu Lys Glu Thr Val Cys Gln Gly Ala Tyr
    130                 135                 140

Pro Ala Phe Glu Arg Asn Gly Leu Val Phe Ala Tyr Met Gly Pro Ala
145                 150                 155                 160

Asp Arg Arg Pro Glu Phe Pro Val Phe Asp Gly Tyr Val Leu Pro Lys
                165                 170                 175

Gly Thr Arg Leu Ile Pro Phe Ser Asn Val Phe Asp Cys Asn Trp Leu
            180                 185                 190

Gln Val Tyr Glu Asn Gln Ile Asp His Tyr His Thr Ala Leu Leu His
        195                 200                 205

Asn Asn Met Thr Val Ala Gly Val Asp Ala Lys Leu Ala Asp Gly Ala
    210                 215                 220

Thr Leu Gln Gly Gly Phe Gly Glu Met Pro Ile Ile Asp Trp His Pro
225                 230                 235                 240

Thr Asp Asp Asn Asn Gly Met Ile Phe Thr Ala Gly Arg Arg Leu Ser
                245                 250                 255

Asp Asp Glu Val Trp Ile Arg Ile Ser Gln Met Gly Leu Pro Asn Trp
            260                 265                 270

Met Gln Asn Ala Ala Ile Val Ala Ala Pro Gln Arg His Ser Gly
        275                 280                 285

Pro Ala Met Ser Arg Trp Gln Val Pro Val Asp Glu His Ser Ile
    290                 295                 300

Ala Phe Gly Trp Arg His Phe Asn Asp Glu Val Asp Pro Glu His Arg
305                 310                 315                 320

Gly Arg Glu Glu Glu Cys Gly Val Asp Lys Ile Asp Phe Leu Ile Gly
                325                 330                 335
```

```
Gln Thr Arg His Arg Pro Tyr Glu Glu Thr Gln Arg Val Pro Gly Asp
                340                 345                 350

Tyr Glu Ala Ile Val Ser Gln Gly Pro Ile Ala Leu His Gly Leu Glu
            355                 360                 365

His Pro Gly Arg Ser Asp Val Gly Val Tyr Met Cys Arg Ser Leu Leu
    370                 375                 380

Arg Asp Ala Val Ala Gly Lys Ala Pro Pro Asp Pro Val Arg Val Lys
385                 390                 395                 400

Ala Gly Ser Thr Asp Gly Gln Thr Leu Pro Arg Tyr Ala Ser Asp Ser
                405                 410                 415

Arg Leu Arg Ile Arg Arg Pro Ser Arg Glu Ala Asp Ser Asp Val
            420                 425                 430

Ile Arg Lys Ala Ala His Gln Val Phe Ala Ile Met Lys Glu Cys Asp
                435                 440                 445

Glu Leu Pro Val Val Gln Arg Arg Pro His Val Leu Arg Arg Leu Asp
            450                 455                 460

Glu Ile Glu Ala Ser Leu
465                 470
```

<210> SEQ ID NO 16
<211> LENGTH: 134
<212> TYPE: PRT
<213> ORGANISM: Aeromonas punctata

<400> SEQUENCE: 16

```
Met Ser Ala Gln Ser Leu Glu Val Gly Gln Lys Ala Arg Leu Ser Lys
1               5                   10                  15

Arg Phe Gly Ala Ala Glu Val Ala Ala Phe Ala Ala Leu Ser Glu Asp
                20                  25                  30

Phe Asn Pro Leu His Leu Asp Pro Ala Phe Ala Ala Thr Thr Ala Phe
            35                  40                  45

Glu Arg Pro Ile Val His Gly Met Leu Leu Ala Ser Leu Phe Ser Gly
    50                  55                  60

Leu Leu Gly Gln Gln Leu Pro Gly Lys Gly Ser Ile Tyr Leu Gly Gln
65                  70                  75                  80

Ser Leu Ser Phe Lys Leu Pro Val Phe Val Gly Asp Glu Val Thr Ala
                85                  90                  95

Glu Val Glu Val Thr Ala Leu Arg Glu Asp Lys Pro Ile Ala Thr Leu
                100                 105                 110

Thr Thr Arg Ile Phe Thr Gln Gly Gly Ala Leu Ala Val Thr Gly Glu
            115                 120                 125

Ala Val Val Lys Leu Pro
    130
```

<210> SEQ ID NO 17
<211> LENGTH: 177
<212> TYPE: PRT
<213> ORGANISM: Escherichia coli

<400> SEQUENCE: 17

```
Met Leu Ala Ala Ile Ser Lys Gln Trp Val Arg Gly Ala Lys Val Glu
1               5                   10                  15

Glu Asp Arg Ile His Pro Phe Arg Lys Tyr Phe Glu Glu Leu Gln Pro
                20                  25                  30

Gly Asp Ser Leu Leu Thr Pro Arg Arg Thr Met Thr Glu Ala Asp Ile
            35                  40                  45
```

```
Val Asn Phe Ala Cys Leu Ser Gly Asp His Phe Tyr Ala His Met Asp
 50                  55                  60

Lys Ile Ala Ala Ala Glu Ser Ile Phe Gly Glu Arg Val Val His Gly
 65                  70                  75                  80

Tyr Phe Val Leu Ser Ala Ala Gly Leu Phe Val Asp Ala Gly Val
                 85                  90                  95

Gly Pro Val Ile Ala Asn Tyr Gly Leu Glu Ser Leu Arg Phe Ile Glu
                100                 105                 110

Pro Val Lys Pro Gly Asp Thr Ile Gln Val Arg Leu Thr Cys Lys Arg
                115                 120                 125

Lys Thr Leu Lys Lys Gln Arg Ser Ala Glu Glu Lys Pro Thr Gly Val
130                 135                 140

Val Glu Trp Ala Val Glu Val Phe Asn Gln His Gln Thr Pro Val Ala
145                 150                 155                 160

Leu Tyr Ser Ile Leu Thr Leu Val Ala Arg Gln His Gly Asp Phe Val
                165                 170                 175

Asp

<210> SEQ ID NO 18
<211> LENGTH: 345
<212> TYPE: PRT
<213> ORGANISM: Streptomyces sp. CNH189

<400> SEQUENCE: 18

Met Glu Met Ala Pro Gly Tyr Val Thr Ser Val Leu Gly Thr Gly Ser
 1               5                  10                  15

Tyr Leu Pro Glu Arg Val Val Thr Asn Glu Glu Ile Glu Ala Arg Val
                 20                  25                  30

Pro Gly Ala Ser Ala Glu Trp Ile Ala Val Arg Thr Ala Ile Val Glu
             35                  40                  45

Arg Arg Tyr Ala Ala Pro Asp Glu Ala Ala Ser Asp Leu Ala Val His
 50                  55                  60

Ala Ala Arg Ala Ala Leu Asp Gln Ala Gly Leu Asp Ala Asp Gly Ile
 65                  70                  75                  80

Asp Phe Ile Ile Val Ala Thr Thr Thr Gly Asp Ala Pro Ile Pro Ser
                 85                  90                  95

Thr Ala Ser Leu Val Gln Leu Ala Leu Gly Ala Arg Ala Ala Cys
                100                 105                 110

Phe Asp Val Asn Ile Ala Cys Thr Gly Phe Val Thr Ala Leu Ser Ile
                115                 120                 125

Ala Arg Ala Tyr Val Ala Leu Asp Pro Thr Thr Lys Val Leu Val Ile
130                 135                 140

Gly Thr Asp Val Trp Thr Arg Phe Ile Asp Phe Asp Asn Arg Ala Thr
145                 150                 155                 160

Ser Val Leu Phe Gly Asp Gly Ala Gly Ala Ala Val Ile Gly Ser Val
                165                 170                 175

Pro His Ala Pro Gly Asp Pro Glu Arg Gly Leu Leu Lys Val Glu Leu
                180                 185                 190

Val Ser Arg Gly Asp Ala His Glu Leu Ile Ser Met Pro Ala Gly Gly
                195                 200                 205

Ser Arg Arg Pro Ala Ser Val Glu Thr Val Ala Asp Gly Gly His Leu
210                 215                 220

Leu Ser Met Gln Gly Arg Gly Val Arg Asp Phe Val Leu Asp Asn Val
225                 230                 235                 240
```

```
Pro Gly Leu Ile Ala Gly Leu Leu Lys Arg Ser Gly His Glu Pro Ala
                245                 250                 255

Asp Val Gln His Phe Val Pro His Gln Ala Asn Gly Arg Leu Val Glu
            260                 265                 270

Glu Leu Ala Gly Ala Ser Gly Leu Val Arg Ala Asp Thr His Leu Pro
        275                 280                 285

Leu Arg His Ser Gly Asn Ile Gly Ser Ala Ser Val Pro Val Ala Leu
    290                 295                 300

Asp Ala Ala Asn Arg Ser Gly Val Leu Arg Asp Gly Asp Leu Val Leu
305                 310                 315                 320

Leu Ala Gly Phe Gly Ala Gly Met Ala Ala Gly Ala Ala Leu Leu Arg
                325                 330                 335

Trp Thr Ala Thr Glu Gly Gly Thr Arg
                340                 345

<210> SEQ ID NO 19
<211> LENGTH: 313
<212> TYPE: PRT
<213> ORGANISM: Synechococcus PCC 7002

<400> SEQUENCE: 19

Ser Asn Ala Ser Gln Ser Leu Ser Val Lys Thr Lys Gln Trp Gln
1               5                   10                  15

Lys Pro Asp His Lys Asn Pro Asn Pro Ile Ala Phe Ile Leu Ser Ser
            20                  25                  30

Pro Arg Ser Gly Ser Thr Leu Leu Arg Val Met Leu Ala Gly His Pro
        35                  40                  45

Gly Leu Tyr Ser Pro Pro Glu Leu His Leu Leu Pro Phe Glu Thr Met
    50                  55                  60

Gly Asp Arg His Gln Glu Leu Gly Leu Ser His Leu Gly Glu Gly Leu
65                  70                  75                  80

Gln Arg Ala Leu Met Asp Leu Glu Asn Leu Thr Pro Glu Ala Ser Gln
                85                  90                  95

Ala Lys Val Asn Gln Trp Val Lys Ala Asn Thr Pro Ile Ala Asp Ile
            100                 105                 110

Tyr Ala Tyr Leu Gln Arg Gln Ala Glu Gln Arg Leu Leu Ile Asp Lys
        115                 120                 125

Ser Pro Ser Tyr Gly Ser Asp Arg His Ile Leu Asp His Ser Glu Ile
    130                 135                 140

Leu Phe Asp Gln Ala Lys Tyr Ile His Leu Val Arg His Pro Tyr Ala
145                 150                 155                 160

Val Ile Glu Ser Phe Thr Arg Leu Arg Met Asp Lys Leu Leu Gly Ala
                165                 170                 175

Glu Gln Gln Asn Pro Tyr Ala Leu Ala Glu Ser Ile Trp Arg Thr Ser
            180                 185                 190

Asn Arg Asn Ile Leu Asp Leu Gly Arg Thr Val Gly Ala Asp Arg Tyr
        195                 200                 205

Leu Gln Val Ile Tyr Glu Asp Leu Val Arg Asp Pro Arg Lys Val Leu
    210                 215                 220

Thr Asn Ile Cys Asp Phe Leu Gly Val Asp Phe Asp Glu Ala Leu Leu
225                 230                 235                 240

Asn Pro Tyr Ser Gly Asp Arg Leu Thr Asp Gly Leu His Gln Gln Ser
                245                 250                 255

Met Gly Val Gly Asp Pro Asn Phe Leu Gln His Lys Thr Ile Asp Pro
```

```
                    260                 265                 270
Ala Leu Ala Asp Lys Trp Arg Ser Ile Thr Leu Pro Ala Ala Leu Gln
                275                 280                 285

Leu Asp Thr Ile Gln Leu Ala Glu Thr Phe Ala Tyr Asp Leu Pro Gln
            290                 295                 300

Glu Pro Gln Leu Thr Pro Gln Thr Gln
305                 310
```

<210> SEQ ID NO 20
<211> LENGTH: 323
<212> TYPE: PRT
<213> ORGANISM: Moorea producens 19L

<400> SEQUENCE: 20

```
Ser Asn Ala Ser Pro Thr Ser Leu Glu Ile Phe Ala Thr Lys Ser Ser
1               5                   10                  15

Pro Ser Gly Asn Ser Ala Arg Pro Ala Ser Val Ser Ser Arg Leu Pro
            20                  25                  30

Gly Ile Ile Phe Ile Leu Ser Ser Pro Arg Ser Gly Ser Thr Leu Leu
        35                  40                  45

Arg Val Met Leu Ala Gly His Ser Ser Leu Phe Ser Pro Pro Glu Leu
50                  55                  60

His Leu Leu Pro Phe Asn Thr Met Lys Glu Arg Gln Glu Gln Leu Asn
65                  70                  75                  80

Leu Ser Tyr Leu Gly Glu Gly Leu Gln Lys Thr Phe Met Glu Val Lys
                85                  90                  95

Asn Leu Asp Ala Thr Ala Ser Gln Ala Leu Ile Lys Asp Leu Glu Ser
            100                 105                 110

Gln Asn Leu Ser Ile Gln Gln Val Tyr Gly Met Leu Gln Glu Asn Ile
        115                 120                 125

Ala Pro Arg Leu Leu Val Asp Lys Ser Pro Thr Tyr Ala Met Glu Pro
130                 135                 140

Thr Ile Leu Glu Arg Gly Glu Ala Leu Phe Ala Asn Ser Lys Tyr Ile
145                 150                 155                 160

Tyr Leu Val Arg His Pro Tyr Ser Val Ile Glu Ser Phe Val Arg Met
                165                 170                 175

Arg Met Gln Lys Leu Val Gly Leu Gly Glu Glu Asn Pro Tyr Arg Val
            180                 185                 190

Ala Glu Gln Val Trp Ala Lys Ser Asn Gln Asn Ile Leu Asn Phe Leu
        195                 200                 205

Ser Gln Leu Glu Pro Glu Arg Gln His Gln Ile Arg Tyr Glu Asp Leu
210                 215                 220

Val Lys Lys Pro Gln Gln Val Leu Ser Gln Leu Cys Asp Phe Leu Asn
225                 230                 235                 240

Val Pro Phe Glu Pro Glu Leu Leu Gln Pro Tyr Gln Gly Asp Arg Met
                245                 250                 255

Thr Gly Gly Val His Ala Ala Ser Leu Ser Ile Ser Asp Pro Asn Phe
            260                 265                 270

Leu Lys His Asn Thr Ile Asp Glu Ser Leu Ala Asp Lys Trp Lys Thr
        275                 280                 285

Ile Gln Leu Pro Tyr Pro Leu Lys Ser Glu Thr Gln Arg Ile Ala Ser
290                 295                 300

Gln Leu Ser Tyr Glu Leu Pro Asn Leu Val Thr Thr Pro Thr Asn Gln
305                 310                 315                 320
```

Gln Pro Gln

<210> SEQ ID NO 21
<211> LENGTH: 286
<212> TYPE: PRT
<213> ORGANISM: Moorea producens 19L

<400> SEQUENCE: 21

```
Ser Asn Ala Met Glu Glu Lys Phe Leu Glu Phe Gly Gly Asn Gln Ile
1               5                   10                  15

Cys Leu Cys Ser Trp Gly Ser Pro Glu His Pro Val Val Leu Cys Ile
            20                  25                  30

His Gly Ile Leu Glu Gln Gly Leu Ala Trp Gln Glu Val Ala Leu Pro
        35                  40                  45

Leu Ala Ala Gln Gly Tyr Arg Val Val Ala Pro Asp Leu Phe Gly His
    50                  55                  60

Gly Arg Ser Ser His Leu Glu Met Val Thr Ser Tyr Ser Ser Leu Thr
65                  70                  75                  80

Phe Leu Ala Gln Ile Asp Arg Val Ile Gln Glu Leu Pro Asp Gln Pro
                85                  90                  95

Leu Leu Leu Val Gly His Ser Met Gly Ala Met Leu Ala Thr Ala Ile
            100                 105                 110

Ala Ser Val Arg Pro Lys Lys Ile Lys Glu Leu Ile Leu Val Glu Leu
        115                 120                 125

Pro Leu Pro Ala Glu Glu Ser Lys Lys Glu Ser Ala Val Asn Gln Leu
    130                 135                 140

Thr Thr Cys Leu Asp Tyr Leu Ser Ser Thr Pro Gln His Pro Ile Phe
145                 150                 155                 160

Pro Asp Val Ala Thr Ala Ala Ser Arg Leu Arg Gln Ala Ile Pro Ser
                165                 170                 175

Leu Ser Glu Glu Phe Ser Tyr Ile Leu Ala Gln Arg Ile Thr Gln Pro
            180                 185                 190

Asn Gln Gly Gly Val Arg Trp Ser Trp Asp Ala Ile Ile Arg Thr Arg
        195                 200                 205

Ser Ile Leu Gly Leu Asn Asn Leu Pro Gly Gly Arg Ser Gln Tyr Leu
    210                 215                 220

Glu Met Leu Lys Ser Ile Gln Val Pro Thr Thr Leu Val Tyr Gly Asp
225                 230                 235                 240

Ser Ser Lys Leu Asn Arg Pro Glu Asp Leu Gln Gln Gln Lys Met Thr
                245                 250                 255

Met Thr Gln Ala Lys Arg Val Phe Leu Ser Gly Gly His Asn Leu His
            260                 265                 270

Ile Asp Ala Ala Ala Leu Ala Ser Leu Ile Leu Thr Ser
        275                 280                 285
```

<210> SEQ ID NO 22
<211> LENGTH: 646
<212> TYPE: PRT
<213> ORGANISM: Elizabethkingia meningoseptica

<400> SEQUENCE: 22

```
Met Asn Pro Ile Thr Ser Lys Phe Asp Lys Val Leu Asn Ala Ser Ser
1               5                   10                  15

Glu Tyr Gly His Val Asn His Glu Pro Asp Ser Ser Lys Glu Gln Gln
            20                  25                  30

Arg Asn Thr Pro Gln Lys Ser Met Pro Phe Ser Asp Gln Ile Gly Asn
```

```
                35                  40                  45
Tyr Gln Arg Asn Lys Gly Ile Pro Val Gln Ser Tyr Asp Asn Ser Lys
 50                  55                  60
Ile Tyr Ile Ile Gly Ser Gly Ile Ala Gly Met Ser Ala Ala Tyr Tyr
 65                  70                  75                  80
Phe Ile Arg Asp Gly His Val Pro Ala Lys Asn Ile Thr Phe Leu Glu
                 85                  90                  95
Gln Leu His Ile Asp Gly Gly Ser Leu Asp Gly Ala Gly Asn Pro Thr
                100                 105                 110
Asp Gly Tyr Ile Ile Arg Gly Arg Glu Met Asp Met Thr Tyr Glu
            115                 120                 125
Asn Leu Trp Asp Met Phe Gln Asp Ile Pro Ala Leu Glu Met Pro Ala
130                 135                 140
Pro Tyr Ser Val Leu Asp Glu Tyr Arg Leu Ile Asn Asp Asn Asp Ser
145                 150                 155                 160
Asn Tyr Ser Lys Ala Arg Leu Ile Asn Asn Lys Gly Glu Ile Lys Asp
                165                 170                 175
Phe Ser Lys Phe Gly Leu Asn Lys Met Asp Gln Leu Ala Ile Ile Arg
            180                 185                 190
Leu Leu Leu Lys Asn Lys Glu Glu Leu Asp Asp Leu Thr Ile Glu Asp
        195                 200                 205
Tyr Phe Ser Glu Ser Phe Leu Lys Ser Asn Phe Trp Thr Phe Trp Arg
210                 215                 220
Thr Met Phe Ala Phe Glu Asn Trp His Ser Leu Leu Glu Leu Lys Leu
225                 230                 235                 240
Tyr Met His Arg Phe Leu His Ala Ile Asp Gly Leu Asn Asp Leu Ser
                245                 250                 255
Ser Leu Val Phe Pro Lys Tyr Asn Gln Tyr Asp Thr Phe Val Thr Pro
            260                 265                 270
Leu Arg Lys Phe Leu Gln Glu Lys Gly Val Asn Ile His Leu Asn Thr
        275                 280                 285
Leu Val Lys Asp Leu Asp Ile His Ile Asn Thr Glu Gly Lys Val Val
    290                 295                 300
Glu Gly Ile Ile Thr Glu Gln Asp Gly Lys Glu Val Lys Ile Pro Val
305                 310                 315                 320
Gly Lys Asn Asp Tyr Val Ile Val Thr Thr Gly Ser Met Thr Glu Asp
                325                 330                 335
Thr Phe Tyr Gly Asn Asn Lys Thr Ala Pro Ile Ile Gly Ile Asp Asn
            340                 345                 350
Ser Thr Ser Gly Gln Ser Ala Gly Trp Lys Leu Trp Lys Asn Leu Ala
        355                 360                 365
Ala Lys Ser Glu Ile Phe Gly Lys Pro Glu Lys Phe Cys Ser Asn Ile
    370                 375                 380
Glu Lys Ser Ala Trp Glu Ser Ala Thr Leu Thr Cys Lys Pro Ser Ala
385                 390                 395                 400
Leu Ile Asp Lys Leu Lys Glu Tyr Ser Val Asn Asp Pro Tyr Ser Gly
                405                 410                 415
Lys Thr Val Thr Gly Gly Ile Ile Thr Ile Thr Asp Ser Asn Trp Leu
            420                 425                 430
Met Ser Phe Thr Cys Asn Arg Gln Pro His Phe Pro Glu Gln Pro Asp
        435                 440                 445
Asp Val Leu Val Leu Trp Val Tyr Ala Leu Phe Met Asp Lys Glu Gly
    450                 455                 460
```

```
Asn Tyr Ile Lys Lys Thr Met Leu Glu Cys Thr Gly Asp Glu Ile Leu
465                 470                 475                 480

Ala Glu Leu Cys Tyr His Leu Gly Ile Glu Asp Gln Leu Glu Asn Val
                485                 490                 495

Gln Lys Asn Thr Ile Val Arg Thr Ala Phe Met Pro Tyr Ile Thr Ser
            500                 505                 510

Met Phe Met Pro Arg Ala Lys Gly Asp Arg Pro Arg Val Val Pro Glu
            515                 520                 525

Gly Cys Lys Asn Leu Gly Leu Val Gly Gln Phe Val Glu Thr Asn Asn
        530                 535                 540

Asp Val Val Phe Thr Met Glu Ser Ser Val Arg Thr Ala Arg Ile Ala
545                 550                 555                 560

Val Tyr Lys Leu Leu Asn Leu Asn Lys Gln Val Pro Asp Ile Asn Pro
                565                 570                 575

Leu Gln Tyr Asp Ile Arg His Leu Leu Lys Ala Ala Lys Thr Leu Asn
            580                 585                 590

Asp Asp Lys Pro Phe Val Gly Glu Gly Leu Leu Arg Lys Val Leu Lys
        595                 600                 605

Gly Thr Tyr Phe Glu His Val Leu Pro Ala Gly Ala Ala Glu Glu Glu
        610                 615                 620

Glu His Glu Ser Phe Ile Ala Glu His Val Asn Lys Phe Arg Glu Trp
625                 630                 635                 640

Val Lys Gly Ile Arg Gly
                645
```

US 10,538,789 B2

METHODS FOR BIOSYNTHESIS OF ISOPRENE

CROSS-REFERENCE TO RELATED APPLICATIONS

This application is a continuation of U.S. application Ser. No. 14/452,201 filed Aug. 5, 2014, which claims priority to U.S. Provisional Ser. No. 61/862,401, filed Aug. 5, 2013, the disclosures of which are incorporated by reference in their entireties.

TECHNICAL FIELD

This invention relates to methods for biosynthesizing isoprene using one or more isolated enzymes such as one or more of a dehydratase, a monooxygenase, a cytochrome P450, an acyl-[acp] dehydrogenase, a mevalonate diphosphate decarboxylase, an acyl-[acp] decarboxylating thioesterase, and a mevalonate-3-kinase; or using recombinant host cells expressing one or more such enzymes.

BACKGROUND

Isoprene is an important monomer for the production of specialty elastomers including motor mounts/fittings, surgical gloves, rubber bands, golf balls and shoes. Styrene-isoprene-styrene block copolymers form a key component of hot-melt pressure-sensitive adhesive formulations and cis-poly-isoprene is utilised in the manufacture of tires (Whited et al., *Industrial Biotechnology*, 2010, 6(3), 152-163).

Manufacturers of rubber goods depend on either imported natural rubber from the Brazilian rubber tree or petroleum-based synthetic rubber polymers (Whited et al., 2010, supra).

Given a reliance on petrochemical feedstocks and the harvesting of trees, biotechnology offers an alternative approach via biocatalysis. Biocatalysis is the use of biological catalysts, such as enzymes, to perform biochemical transformations of organic compounds.

Accordingly, against this background, it is clear that there is a need for sustainable methods for producing intermediates, in particular isoprene, wherein the methods are biocatalysis based.

Both bioderived feedstocks and petrochemical feedstocks are viable starting materials for the biocatalysis processes.

The introduction of vinyl groups into medium carbon chain length enzyme substrates is a key consideration in synthesising isoprene via biocatalysis processes.

There are known metabolic pathways leading to the synthesis of isoprene in prokaryotes such as *Bacillis subtillis* and eukaryotes such as *Populus alba* (Whited et al., 2010, supra).

Isoprene may be synthesized via two routes leading to the precursor dimethylvinyl-PP, such as the mevalonate and the non-mevalonate pathway (Kuzuyama, *Biosci. Biotechnol. Biochem.*, 2002, 66(8), 1619-1627). The mevalonate pathway incorporates a decarboxylase enzyme, mevalonate diphosphate decarboxylase (hereafter MDD), that introduces the first vinyl-group into the precursors leading to isoprene. The second vinyl-group is introduced by isoprene synthase (hereafter ISPS) in the final step in synthesizing isoprene.

The mevalonate pathway (FIG. 1) has been exploited in the biocatalytic production of isoprene using *E. coli* as host. *E. coli* engineered with the mevalonate pathway requires three moles of acetyl-CoA, three moles of ATP and two moles of NAD(P)H to produce a mole of isoprene. Given a theoretical maximum yield of 25.2% (w/w) for the mevalonate pathway, isoprene has been produced biocatalytically at a volumetric productivity of 2 g/(L·h) with a yield of 11% (w/w) from glucose (Whited et al., 2010, supra). Particularly, the phosphate activation of mevalonate to 5-diphosphomevalonate is energy intensive metabolically, requiring two moles of ATP per mole of isoprene synthesis (FIG. 1). Accordingly, reducing the ATP consumption can improve the efficiency of the pathway.

SUMMARY

The inventors have determined that it is possible to construct a biochemical pathway to synthesize isoprene from (R)-mevalonate, 3-methyl-2-oxopentanoate, 4-methyl-2-oxopentanoate or isobutyryl-CoA, by introducing two vinyl groups without the need for terminal alcohol phosphorylation. Such pathways rely on a dehydratase, monooxygenase, cytochrome P450, or dehydrogenase enzyme to introduce the first vinyl group; and a MDD, mevalonate-3-kinase, acyl-[acp] decarboxylating thioesterase (e.g., CurM TE) or a linalool dehydratase to introduce the second vinyl group into the precursors leading to isoprene synthesis. The methods described herein can include introducing the first vinyl group, introducing the second vinyl group, or introducing both the first and second vinyl groups.

Prior to the present invention, it was not known that enzymes capable of introducing two vinyl groups, without the need for terminal alcohol phosphorylation, could be used to generate non-phosphorylated intermediates for the synthesis of isoprene. Thus the invention provides enzymes that can convert the central precursors mevalonate, 3-methyl-2-oxopentanoate, 4-methyl-2-oxopentanoate or isobutyryl-CoA into isoprene.

In some embodiments, 3-methyl-pent-2-enoyl-CoA or 4-methyl-pent-2-enoyl-CoA is formed by a 2-hydroxyacyl-CoA dehydratase classified, for example, under EC 4.2.1.-, such as the gene products of HadBC (SEQ ID NOs: 3 and 4) and its initiator HadI (SEQ ID NO: 2), or the gene products of HgdAB (SEQ ID NOs: 6 and 7) and its initiator HdgC (SEQ ID NO: 5). In some embodiments, the 2-hydroxyacyl-CoA dehydratase is the result of enzyme engineering. The 2-hydroxyacyl-CoA dehydratase enzymes isolated from anaerobic bacteria possess a common catalytic mechanism employed in amino acid degradation pathways. For example, the gene products of HadBC/HadI from *Clostridium difficile* catalyse the conversion of (R)-2-hydroxyisocaproyl-CoA to isocaprenoyl-CoA. Similarly, the gene products of HgdAB/HdgC catalyse the conversion of 2-hydroxyglutaryl-CoA to glutaconyl-CoA (Kim et al., FEMS Microbiol. Reviews, 2004, 28, 455-468). See FIGS. 2-5.

In some embodiments, the first vinyl group is introduced into 3-methyl-pent-2-enoyl-ACP, derived from the central metabolite 3-methyl-2-oxopentanoate, which may be enzymatically converted in one or more steps to 3-methyl-3-hydroxypent-4-enoate or 3-methyl-3-sulphoryl-pent-4-enoyl-ACP (as shown, for example, in FIG. 2). It has been demonstrated that the gene product of tcsD (SEQ ID NO: 14) from *Streptomyces kanamyceticus* has dehydrogenase activity for straight and branch chain C5 acyl-ACP substrates (Mo et al., *JACS*, 2011, 133, 976-985).

In some embodiments, the first vinyl group is introduced forming 4-methyl-pent-2-enoyl-ACP, derived from the central metabolite 4-methyl-2-oxopentanoate or isobutyryl- CoA, which may be enzymatically converted in one or more steps to 4-methyl-3-hydroxypent-4-enoate, 4-methyl-3-sulphoryl-pent-4-enoyl-ACP, or 3-methyl-3-buten-2-ol (see, for example, FIG. 3, FIG. 6, and FIG. 7). It has been demonstrated that the gene product of tcsD (SEQ ID NO: 14) from *Streptomyces kanamyceticus* has dehydrogenase activity for 4-methyl-pent-2-enoyl-ACP (Mo et al., 2011, supra).

In some embodiments, the first vinyl group is introduced into 3-methyl-3-hydroxy-pentanoate, which may be enzymatically converted in one or more steps to 3-methyl-3-hydroxypent-4-enoate (see, for example, FIG. 4). It has been demonstrated that the monooxygenase encoded by mdpJ (SEQ ID NO: 15) introduces a terminal double bond into allyl groups bound to a secondary alcohol (Schäfer et al., *Appl. Environ. Microbiol.*, 2012, 78(17), 6280-6284).

In some embodiments, the first vinyl group is introduced into 4-methyl-3-hydroxypentanoate, which may be enzymatically converted in one or more steps to 4-methyl-3-hydroxypent-4-enoate (see, for example, FIG. 5).

In some embodiments, the first vinyl group is introduced into mevalonate, which can be converted enzymatically in one or more steps to 3-hydroxy-3-methyl-pent-4-enoate (as shown, for example, in FIG. 8).

In some embodiments, the 3-hydroxy functional group is introduced into 3-methyl-pent-2-enoyl-CoA or 4-methyl-pent-2-enoyl-CoA by a (R)-specific enoyl-CoA hydratase enzyme classified, for example, under EC 4.2.1.119 such as the gene product of phaJ (SEQ ID NO: 16, Fukui et al., *J. Bacteriol.*, 1998, 180(3), 667-673) or MaoC (SEQ ID NO: 17; Park and Lee, *J. Bacteriol.*, 2003, 185(18), 5291-5397) or a bacterial (S)-specific enoyl-CoA hydratase classified, for example, under EC 4.2.1.17 such as the gene product of YsiB (SEQ ID NO: 1). In some embodiments, the enoyl-CoA hydratase enzyme is the result of enzyme engineering. A single enzyme candidate for the introduction of a 3-hydroxy functional group into 3-methylbuten-2-enoyl-CoA has been identified previously in the cell free extract of *Galactomyces reessii*, containing an enoyl-CoA hydratase classified in EC 4.2.1.17 that converts 3-methylbuten-2-enoyl-CoA to 3-hydroxy-3-methylbutanoyl-CoA (Lee et al., *Appl. Environ. Microbiol.*, 1997, 63(11), 4191-4195). Equivalent enoyl-CoA hydratase activity from bacterial origin has not been identified. See FIG. 4 and FIG. 5.

In some embodiments, 4-methyl-3-oxopentanoyl-ACP is formed by condensing isobutyryl-CoA and malonyl-ACP using a β-ketoacyl-ACP-synthase enzyme classified, for example, under EC 2.3.1.- (EC 2.3.1.41, EC 2.3.1.79, or EC 2.3.1.80) such as the gene product of AnlF (SEQ ID NO: 18). It has been demonstrated that the gene product of anlF condenses isobutyryl-CoA and malonyl-ACP (Lechner et al., *ACS Synth. Biol.*, 2013, 2(7), 379-83).

In some embodiments, the second vinyl group is introduced into a medium chain carbon alkenoate by a mevalonate diphosphate decarboxylase (Lefurgy et al., *J. Biol. Chem.*, 2010, 285(27), 20654-20663) or a mevalonate 3-kinase (Vinokur et al., *Biochemistry*, 2014, 53(25), 4161-4168), converting 3-methyl-3-hydroxypent-4-enoate or 4-methyl-3-hydroxypent-4-enoate to isoprene (FIGS. 2-5).

In some embodiments, the second vinyl group is introduced into a medium chain carbon alkenoate by a decarboxylating thioesterase (CurM TE), converting 3-methyl-3-sulphoryl-pent-4-enoyl-ACP or 4-methyl-3-sulphoryl-pent-4-enoyl-ACP to isoprene (see, FIG. 2, FIG. 3 and FIG. 6; Gehret et al., *J. Biol. Chem.*, 2011, 286(16), 14445-14454).

In some embodiments, the second vinyl group is introduced by a linalool dehydratase classified, for example, under EC 4.2.1.127 (Brodkorb et al., *J. Biol. Chem.*, 2010, 285(40), 30436-30442) or a dehydratase classified under EC 4.2.1.- (such as one isolated from species such as *Aquincola tertiaricarbonis* or *Methylibium petroleiphilum* PM1; Schäfer et al., 2011, supra) (FIG. 3 and FIG. 7).

In one aspect, this document features a method for enzymatically synthesizing isoprene. The method includes enzymatically introducing a terminal vinyl group into 3-methyl-pent-2-enoyl-[acp], 4-methyl-pent-2-enoyl-[acp], 3-methyl-3-hydroxy-pentanoate, 4-methyl-3-hydroxypentanoate, or mevalonate, and converting the resulting product in one or more steps to isoprene. The first vinyl group can be introduced using a dehydratase classified under EC 4.2.1.- (e.g., a dehydratase having at least 70% homology to the amino acid sequence set forth in SEQ ID NO: 22), a monooxygenase (e.g., a monooxygenase having at least 70% homology to the amino acid sequence set forth in SEQ ID NO: 15), a cytochrome P450 reductase, or an acyl-[acp] dehydrogenase (e.g., an acyl-[acp] dehydrogenase having at least 70% homology to the amino acid sequence set forth in SEQ ID NO:14). For example, a terminal vinyl group can be introduced into 3-methyl-pent-2-enoyl-[acp] or 4-methyl-pent-2-enoyl-[acp] using an acyl-[acp] dehydrogenase. For example, a terminal vinyl group can be introduced into mevalonate using a dehydratase classified under EC 4.2.1.-. For example, a terminal vinyl group can be introduced into 3-methyl-3-hydroxy-pentanoate or 4-methyl-3-hydroxypentanoate using a monooxygenase or a cytochrome P450 reductase. 3-methyl-pent-2-enoyl-[acp], 4-methyl-pent-2-enoyl-[acp], 3-methyl-3-hydroxy-pentanoate, or 4-methyl-3-hydroxypentanoate, can be enzymatically formed from 3-methyl-2-oxopentanoate, 4-methyl-2-oxopentanoate, or isobutyryl-CoA.

This document also features a method for enzymatically synthesizing isoprene that includes enzymatically introducing a second terminal vinyl group into 3-methyl-3-hydroxypent-4-enoate, 4-methyl-3-hydroxypent-4-enoate, 4-methyl-3-sulphorylpent-4-enoyl-[acp], or 3-methyl-3-buten-2-ol to produce isoprene. The second vinyl group can be introduced using a mevalonate diphosphate decarboxylase, a mevalonate 3-kinase, an acyl-[acp] decarboxylating thioesterase, or a linalool dehydratase. The mevalonate diphosphate decarboxylase can have at least 70% homology to the mevalonate diphosphate decarboxylase of any one of the amino acid sequences set forth in SEQ ID NOs:8-11. The mevalonate 3-kinase can have at least 70% homology to the amino acid sequence of SEQ ID NO: 12. The acyl-[acp] decarboxylating thioesterase can have at least 70% homology to the amino acid sequence of SEQ ID NO: 21. The linalool dehydratase can have at least 70% homology to the amino acid sequence of SEQ ID NO: 13. The mevalonate diphosphate decarboxylase can have a histidine at the position aligning with residue 74 of SEQ ID NO:11 and/or a phenylalanine at the position aligning with residue 145 of SEQ ID NO:11. The mevalonate diphosphate decarboxylase can have the amino acid sequence set forth in SEQ ID NO:11, except that a histidine is substituted at position 74 for arginine and/or a phenylalanine is substituted at position 145 for isoleucine. For example, the mevalonate diphosphate decarboxylase can convert 3-methyl-3-hydroxypent-4-enoate or 4-methyl-3-hydroxypent-4-enoate to isoprene. For example, a mevalonate 3-kinase can convert 3-methyl-3-hydroxypent-4-enoate or 4-methyl-3-hydroxypent-4-enoate to isoprene. For example, the acyl-[acp] decarboxylating thioesterase can convert 3-methyl-3-sulphorylpent-4-enoyl-[acp] or 4-methyl-3-sulphorylpent-4-enoyl-[acp] to isoprene. For example, the linalool dehydratase can convert 3-methyl-3-buten-2-ol to isoprene.

Any of the methods described herein can be performed using isolated enzymes.

Any of the methods described herein can be performed using cell lysates comprising the enzymes.

Any of the methods described herein can be performed in a recombinant host. For example, the host can be a prokaryote selected from the group consisting of the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens* or *Pseudomonas putida*; from the genus *Bacillus* such as *Bacillus subtillis*; or from the genus *Rhodococcus* such as *Rhodococcus equi*. The host can be a eukaryote selected from the group consisting of the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*.

The host can be subjected to a fermentation strategy entailing anaerobic, micro-aerobic or aerobic cultivation. A cell retention strategy using a ceramic hollow fiber membrane can be employed to achieve and maintain a high cell density during fermentation.

The principal carbon source fed to the fermentation can derive from a biological or a non-biological feedstock. The biological feedstock can be, or can derive from, monosaccharides, disaccharides, hemicellulose such as levulinic acid and furfural, cellulose, lignocellulose, lignin, triglycerides such as glycerol and fatty acids, agricultural waste or municipal waste. The non-biological feedstock can be, or can derive from, either natural gas, syngas, $CO_2/H_2$, methanol, ethanol, non-volatile residue (NVR), caustic wash from cyclohexane oxidation processes or other waste stream from either the chemical or petrochemical industries.

This document also features a recombinant host producing isoprene. The host includes at least one exogenous nucleic acid encoding (i) a 2-hydroxyacyl-CoA dehydratase or a β-ketoacyl-ACP-synthase; (ii) an acyl-ACP dehydrogenase, a monooxygenase, a cytochrome P450, or a dehydratase classified under EC 4.2.1.- and (iii) a mevalonate diphosphate decarboxylase, a mevalonate 3-kinase, an acyl-ACP decarboxylating thioesterase, or a linalool dehydratase, the host producing isoprene. The host can include at least one exogenous nucleic acid encoding (i) the 2-hydroxyacyl-CoA dehydratase, (ii) the acyl-ACP dehydrogenase, and (iii) the mevalonate diphosphate decarboxylase, mevalonate 3-kinase, acyl ACP decarboxylating thioesterase, or linalool dehydratase. The host can include at least one exogenous nucleic acid encoding (i) the 2-hydroxyacyl-CoA dehydratase, (ii) the monooxygenase or cytochrome P450, and (iii) the mevalonate diphosphate decarboxylase, mevalonate 3-kinase, acyl-ACP decarboxylating thioesterase, or linalool dehydratase. The host can include at least one exogenous nucleic acid encoding (i) the β-ketoacyl-ACP-synthase, (ii) the acyl-ACP dehydrogenase, and (iii) the mevalonate diphosphate decarboxylase, mevalonate 3-kinase, acyl-ACP decarboxylating thioesterase, or linalool dehydratase.

This document also features a recombinant host that includes at least one exogenous nucleic acid encoding (i) a dehydratase classified under EC 4.2.1.- and (ii) a mevalonate diphosphate decarboxylase or a mevalonate 3-kinase, the host producing isoprene.

In any of the recombinant hosts, the enzymes from the mevalonate pathway leading to isoprenoid synthesis, such as enzymes classified under EC 2.3.1.9, EC 2.3.3.10, EC 1.1.1.34 or EC 1.1.1.88, can be introduced or gene dosed into the host that utilizes the non-mevalonate or 2-C-methyl-D-erythritol 4-phosphate pathway for isoprenoid synthesis.

In the recombinant host, the enzymes from the non-mevalonate or 2-C-methyl-D-erythritol 4-phosphate pathway can be introduced into a host microorganism that utilizes the mevalonate pathway for isoprenoid synthesis.

In any of the recombinant hosts described herein, the host can include one or more of the following attenuated enzymes: the enzyme classified under EC 2.7.1.36 accepting mevalonate as substrate, a polymer synthase, an acetate kinase, a lactate dehydrogenase, an enzyme degrading phosphoenolpyruvate to succinate, and an enzyme degrading acetyl-CoA to ethanol.

In any of the recombinant hosts described herein, the host can overexpress one or more genes encoding: an enzyme for 3'-phosphoadenosine-5'-phosphosulfate synthesis, a puridine nucleotide transhydrogenase, a glyceraldehyde-3-phosphate-dehydrogenase, a malic enzyme, a glucose-6-phosphate dehydrogenase, and a fructose 1,6-diphosphatase.

In any of the recombinant hosts described herein, the host can include a feedback inhibition resistant mutant of an acetolactate synthase.

In any of the recombinant hosts described herein, the host can include an acetolactate synthase under control of a promoter not subject to genetic repression by a branched chain amino acid.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes can optionally be immobilized to a solid substrate such as the floors and/or walls of appropriate reaction vessels. Moreover, such extracts include lysates (e.g., cell lysates) that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DESCRIPTION OF DRAWINGS

FIGS. 9A-9F contain the amino acid sequences of a *Bacillus subtilis* enoyl-CoA hydratase encoded by YsiB (see Genbank Accession No. CAA99573.1, SEQ ID NO:1), a *Clostridium difficile* 2-hydroxyacyl-CoA dehydratase activator encoded by HadI (See Genbank Accession No. AAV40818.1, SEQ ID NO: 2), a *Clostridium difficile* 2-hydroxyacyl-CoA dehydratase encoded by HadBC (see Genbank Accession Nos. AAV40819.1 and AAV40820.1, SEQ ID NO: 3 and SEQ ID NO:4, respectively), an *Acidaminococcus fermentans* 2-hydroxyacyl-CoA dehydratase activator encoded by HgdC (See Genbank Accession No. CAA42196.1, SEQ ID NO: 5), an *Acidaminococcus fermentans* 2-hydroxyacyl-CoA dehydratase encoded by HdgAB (see Genbank Accession Nos. CAA32465.1 and CAA32466.1, SEQ ID NO: 6 and SEQ ID NO:7, respectively), a *Streptococcus pyogenes* mevalonate diphosphate decarboxylase (see Genbank Accession No. AAK33797.1, SEQ ID NO: 8), a *Thioalkalimicrobium aerophilum* mevalonate diphosphate decarboxylase (see Genbank Accession No. AHF01884.1, SEQ ID NO: 9), a *Streptococcus pneumoniae* mevalonate diphosphate decarboxylase (see Genbank Accession No. CAR68209.1, SEQ ID NO: 10), a *Saccharomyces cerevisiae* mevalonate diphosphate decarboxylase (see Genbank Accession No. CAA66158.1, SEQ ID NO: 11), a *Thermoplasma acidophilum* mevalonate 3-kinase (see Genbank Accession No. CAC12426.1, SEQ ID NO: 12), a *Castellaniella defragrans* linalool dehydratase (see Genbank Accession No. CBW30776.1, SEQ ID NO: 13), a *Streptomyces kanamyceticus* acyl-ACP dehydrogenase encoded by tcsD (see Genbank Accession No. ADU56239.1, SEQ ID NO: 14), an *Aquincola tertiaricarbonis* monooxygenase encoded by mdpJ (see Genbank Accession No. AER12131.1, SEQ ID NO: 15), an *Aeromonas punctata* enoyl-CoA hydratase encoded by phaJ (see Genbank Accession No. BAA21816.1, SEQ ID NO: 16), an *Escherichia coli* enoyl-CoA hydratase encoded by MaoC (see Genbank Accession No. AFY98994.1, SEQ ID NO: 17), a *Streptomyces* sp. CNH189 β-ketoacyl-ACP-synthase encoded by AnlF (see Genbank Accession No. AFY98994.1, SEQ ID NO: 18), a *Synechococcus* PCC 7002 sulfotransferase domain encoded by OLS ST (see Genbank Accession No. ACA99172.1, SEQ ID NO: 19), a *Moorea producens* 19L sulfotransferase domain encoded by CurM ST (see Genbank Accession No. ACV42478.1, SEQ ID NO: 20), a *Moorea producens* 19L thioesterase domain encoded by CurM TE (see Genbank Accession No. ACV42478.1, SEQ ID NO: 21) and an *Elizabethkingia meningoseptica* oleate hydratase encoded by ohyA (see Genbank Accession No. ACT54545.1, SEQ ID NO: 22).

FIG. 11 is a table providing the details of an LC-MS analysis of an enzyme assay for enoyl-CoA hydratase (encoded by phaJ) activity in the reverse direction, accepting racemic 3-hydroxybutanoyl-CoA as substrate.

FIG. 12 is a table providing details of an LC-MS analysis of an enzyme assay for enoyl-CoA hydratase (encoded by phaJ) activity in the reverse direction, accepting 3-methyl-3-hydroxypentanoyl-CoA as substrate.

FIG. 13 is a table providing details of an LC-MS analysis of an enzyme assay for enoyl-CoA hydratase (encoded by phaJ) activity in the reverse direction, accepting 4-methyl-3-hydroxypentanoyl-CoA as substrate.

DETAILED DESCRIPTION

Figure 1:
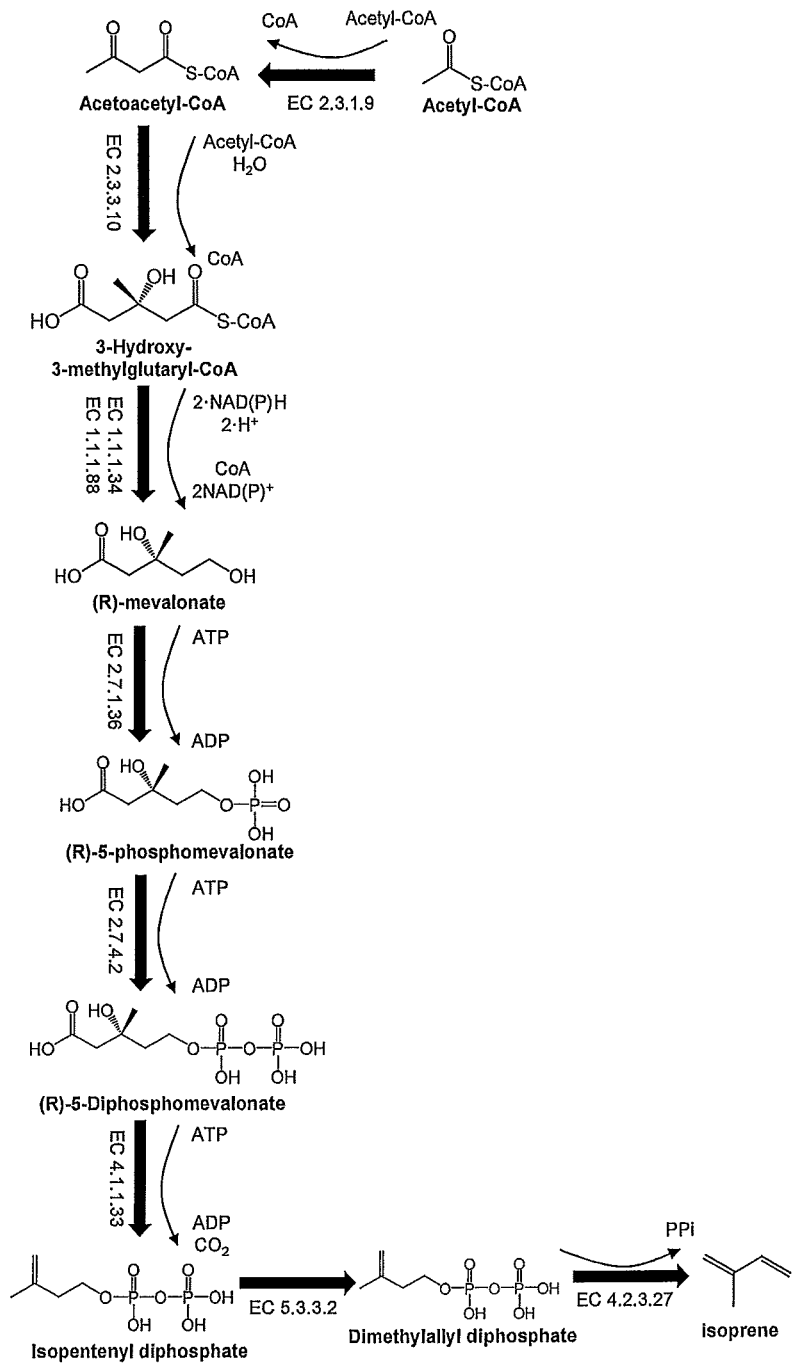
FIG. 1 is a schematic of an exemplary biochemical pathway leading to isoprene using (R)-mevalonate as a central precursor via isopentenyl diphosphate and dimethyl allyl diphosphate.

In particular, the invention provides enzymes and recombinant host microorganisms for isoprene synthesis in which two vinyl groups are introduced into central precursors such as 3-methyl-pent-2-enoyl-[acp], 4-methyl-pent-2-enoyl-[acp], 3-methyl-3-hydroxy-pentanoate, 4-methyl-3-hydroxypentanoate, or mevalonate, to produce isoprene in one or more enzymatic steps. 3-methyl-pent-2-enoyl-[acp], 4-methyl-pent-2-enoyl-[acp], 3-methyl-3-hydroxy-pentanoate, 4-methyl-3-hydroxypentanoate can be enzymatically produced from 3-methyl-2-oxopentanoate, 4-methyl-2-oxopentanoate, or isobutyryl-CoA, in one or more enzymatic steps. As used herein, the term "central precursor" is used to denote any metabolite in any metabolic pathway shown herein leading to the synthesis of isoprene. The term "central metabolite" is used herein to denote a metabolite that is produced in all microorganisms to support growth.

As such, host microorganisms described herein can include pathways that can be manipulated such that isoprene can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host: 2-hydroxyacyl-CoA dehydratase, a 3-hydroxyacyl-[acp] dehydratase, a (R)-2-hydroxyacyl dehydrogenase, an acyl-ACP dehydrogenase such as the gene product of tcsD, a monooxgyenase such as the gene product of mdpJ, a (R)-specific enoyl-CoA hydratase such as the gene product of pha or MaoC, a (S)-specific enoyl-CoA hydratase such as the gene product of YsiB, a β-ketoacyl-ACP synthase such as the gene product of AnlF, a mevalonate diphosphate decarboxylase, a mevalonate 3-kinase, a decarboxylating thioesterase, a dehydratase, a linalool dehydratase, an oleate hydratase such as the gene product of ohyA, a kevitone hydrase, a carotenoid 1,2-hydratase, a CoA transferase, a CoA ligase, an acyl transferase, a thioesterase, an acyl[acp] thioesterase, a 3-hydroxyacyl-[acp]:CoA transacylase, a sulfotransferase, an acetoacetate decarboxylase, a secondary alcohol dehydrogenase, a hydroxymethylglutaryl-CoA reductase, a hydroxymethylglutaryl-CoA synthase, or a 3-oxoacyl-[acp] reductase.

In some embodiments, a recombinant host includes at least one exogenous nucleic acid encoding (i) a 2-hydroxyacyl-CoA dehydratase or a β-ketoacyl-ACP-synthase; (ii) an acyl-ACP dehydrogenase, a monooxygenase, a cytochrome P450, or a dehydratase classified under EC 4.2.1.- and (iii) a mevalonate diphosphate decarboxylase, a mevalonate 3-kinase, an acyl-ACP decarboxylating thioesterase, or a linalool dehydratase, and produces isoprene. For example, a host can include at least one exogenous nucleic acid encoding a 2-hydroxyacyl-CoA dehydratase, an acyl-ACP dehydrogenase, and a mevalonate diphosphate decarboxylase, mevalonate 3-kinase, an acyl-ACP decarboxylating thioesterase, or a linalool dehydratase. For example, a host can include at least one exogenous nucleic acid encoding (i) a 2-hydroxyacyl-CoA dehydratase, (ii) a monooxygenase or a cytochrome P450, and (iii) a mevalonate diphosphate decarboxylase, mevalonate 3-kinase, acyl-ACP decarboxylating thioesterase, or linalool dehydratase. For example, a host can include at least one exogenous nucleic acid encoding (i) a β-ketoacyl-ACP-synthase, (ii) an acyl-ACP dehydrogenase, and (iii) a mevalonate diphosphate decarboxylase, mevalonate 3-kinase, acyl-ACP decarboxylating thioesterase, or linalool dehydratase.

In some embodiments, a recombinant host can include at least one exogenous nucleic acid encoding a (R)-2-hydroxyacyl dehydrogenase, a 2-hydroxyacyl-CoA dehydratase and 2-hydroxyacyl-CoA dehydratase initiator, and an acyl-[acp] dehydrogenase and produce 3-methyl-pent-2,4-dienoyl-[acp] or 4-methyl-pent-2,4-dienoyl-[acp]. Such a host also can include one or more of the following exogenous enzymes: a CoA transferase or a CoA ligase, and/or an acyl transferase and a 4' phosphopantetheinyl transferase, and produce 3-methyl-pent-2,4-dienoyl-[acp] or 4-methyl-pent-2,4-dienoyl-[acp]. Either of such hosts further can include an exogenous 3-hydroxyacyl-[acp] dehydratase and further produce 3-methyl-3-hydroxypent-4-enoyl-[acp] or 4-methyl-3-hydroxypent-4-enoyl-[acp]. See, FIGS. 2 and 3.

Figure 6:
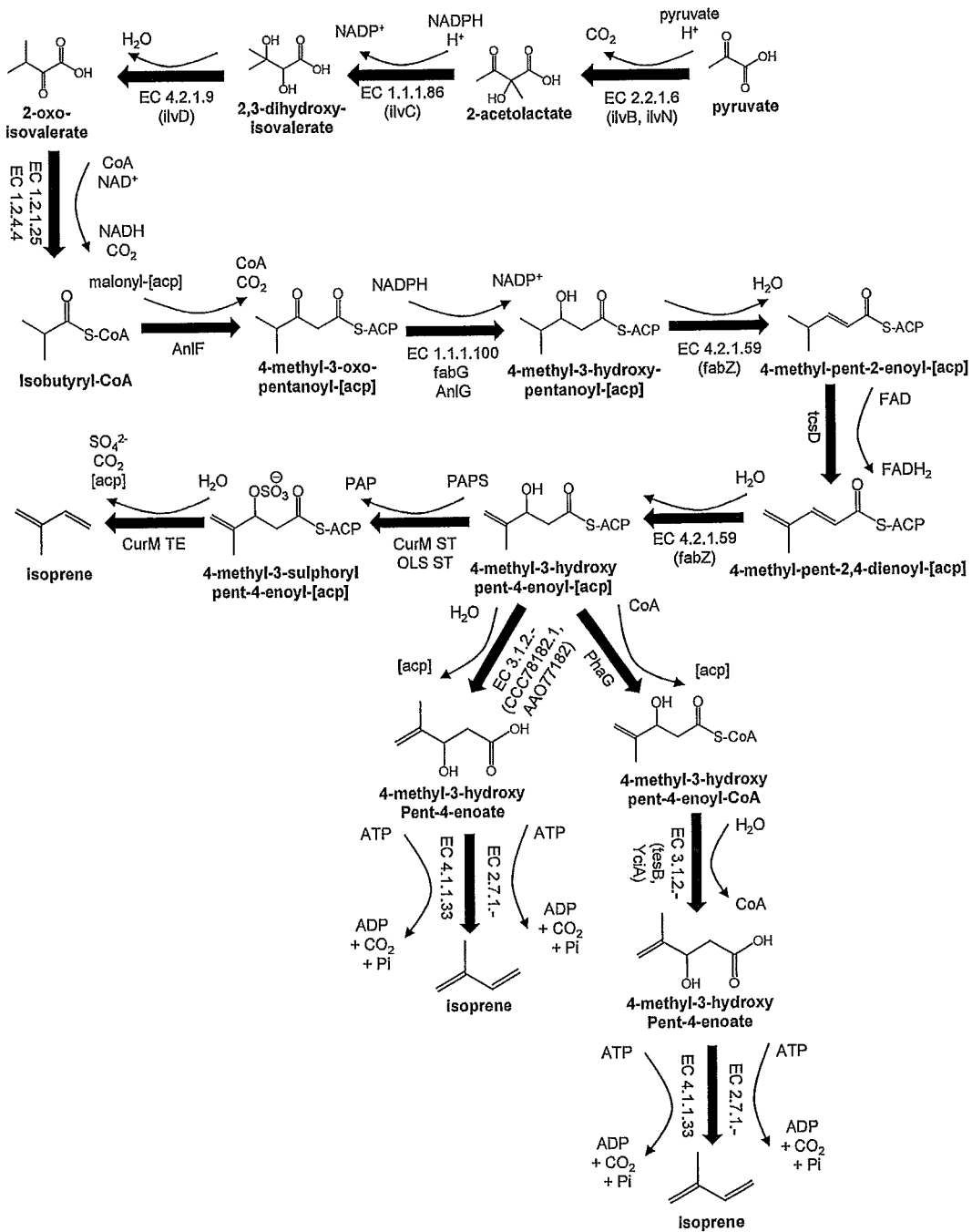
FIG. 6 is a schematic of exemplary biochemical pathways leading to isoprene using isobutyryl-CoA as a central precursor and an acyl-ACP dehydrogenase to introduce the first vinyl group and a GHMP superfamily enzyme to introduce the second vinyl group.

In some embodiments, a recombinant host can include an exogenous nucleic acid encoding one or more of a β-ketoacyl-ACP-synthase and produce 4-methyl-3-hydroxypent-4-enoyl-[acp]. Such a host also can include one or more of the following exogenous enzymes: a 3-oxoacyl-[acp] reductase, a 3-hydroxyacyl-[acp] dehydratase, and an acyl-CoA dehydrogenase and produce 4-methyl-3-hydroxypent-4-enoyl-[acp]. See, FIG. 6 and FIG. 7.

In some embodiments, a recombinant host producing 3-methyl-3-hydroxypent-4-enoyl-[acp] or 4-methyl-3-hydroxypent-4-enoyl-[acp] further can include an exogenous sulfotransferase and an exogenous decarboxylating thioesterase and produce isoprene. See, FIG. 2, FIG. 3, and FIG. 6.

In some embodiments, a recombinant host producing 3-methyl-3-hydroxypent-4-enoyl-[acp] or 4-methyl-3-hydroxypent-4-enoyl-[acp] can include one or more of an exogenous (R)-3-hydroxyacyl-ACP:CoA transacylase, and a mevalonate diphosphate decarboxylase or a mevalonate 3-kinase and produce isoprene. Such a host also can include a thioesterase or a CoA transferase, and produce isoprene. See, FIG. 2, FIG. 3, and FIG. 6.

In some embodiments, a recombinant host producing 3-methyl-3-hydroxypent-4-enoyl-[acp] or 4-methyl-3-hydroxypent-4-enoyl-[acp] further can include one or more of an exogenous thioesterase (e.g., an acyl [acp] thioesterase) and a mevalonate diphosphate decarboxylase or a mevalonate 3-kinase and produce isoprene. See, FIG. 2, FIG. 3, and FIG. 6.

In some embodiments, a recombinant host producing 4-methyl-3-hydroxypent-4-enoyl-[acp] can include one or more of an exogenous (R)-3-hydroxyacyl-ACP:CoA transacylase, an acetoacetate decarboxylase, a secondary alcohol dehydrogenase, and a linalool dehydratase and produce isoprene. Such a host also can include one or more of the following exogenous enzymes: a dehydrogenase, a CoA-transferase, and/or a thioesterase and produce isoprene. See, FIG. 3 and FIG. 7.

In some embodiments, a recombinant host producing 4-methyl-3-hydroxypent-4-enoyl-[acp] can include one or more of an exogenous a thioesterase (e.g., an acyl-[acp] thioesterase), an acetoacetate decarboxylase, a secondary alcohol dehydrogenase, and a linalool dehydratase and produce isoprene. Such a host also can include an exogenous 3-oxoacyl-[acp] reductase and produce isoprene. See, FIG. 7.

In some embodiments, a recombinant host can include at least one exogenous nucleic acid encoding a (R)-2-hydroxyacyl dehydrogenase, a 2-hydroxyacyl-CoA dehydratase and 2-hydroxyacyl-CoA dehydratase initiator, and an (R)-specific or (S)-specific enoyl-CoA hydratase and produce 3-methyl-3-hydroxy-pentanoyl-CoA or 4-methyl-3-hydroxy-pentanoyl-CoA. Such a host also can include one or more of the following exogenous enzymes: a CoA transferase or a CoA ligase, and/or an acyl transferase and a 4' phosphopantetheinyl transferase, and produce 3-methyl-3-hydroxy-pentanoyl-CoA or 4-methyl-3-hydroxy-pentanoyl-CoA. Such hosts further can include an exogenous thioesterase or a CoA transferase and further produce 3-methyl-3-hydroxypentanoate or 4-methyl-3-hydroxypentanoate. Any of such hosts further can include a monooxygenase and produce 3-methyl-3-hydroxy-pent-4-enoate or 4-methyl-3-hydroxypent-4-enoate. See, FIG. 4 and FIG. 5.

A recombinant host producing 3-methyl-3-hydroxy-pent-4-enoate or 4-methyl-3-hydroxypent-4-enoate can include a mevalonate diphosphate decarboxylase or a mevalonate 3-kinase and produce isoprene. See, FIG. 4 and FIG. 5.

In some embodiments, a recombinant host can include an exogenous dehydratase, and a mevalonate diphosphate decarboxylase or a mevalonate 3-kinase and produce isoprene. Such a host further can include one or more of the following exogenous enzymes: an acetyl-CoA C-acetyltransferase, a hydroxymethylglutaryl-CoA synthase, and/or a hydroxymethylglutaryl-CoA reductase, See, FIG. 8.

Within an engineered pathway, the enzymes can be from a single source, i.e., from one species, or can be from multiple sources, i.e., different species. Nucleic acids encoding the enzymes described herein have been identified from various organisms and are readily available in publicly available databases such as GenBank or EMBL.

Any of the enzymes described herein that can be used for isoprene production can have at least 70% sequence identity (homology) (e.g., at least 75%, 80%, 85%, 90%, 95%, 97%, 98%, 99%, or 100%) to the amino acid sequence of the corresponding wild-type enzyme.

For example, an enoyl-CoA hydratase described herein can have at least 70% sequence identity (homology) (e.g., at least 75%, 80%, 85%, 90%, 95%, 97%, 98%, 99%, or 100%) to the amino acid sequence of a *Bacillus subtilis* (GenBank Accession No. CAA99573.1, SEQ ID NO:1), a *Aeromonas punctata* (Genbank Accession No. BAA21816.1, SEQ ID NO: 16), or an *Escherichia coli* (Genbank Accession No. AFY98994.1, SEQ ID NO: 17) enoyl-CoA hydratase. See, FIGS. 9A-9F.

For example, a 2-hydroxyacyl-CoA dehydratase described herein can have at least 70% sequence identity (homology) (e.g., at least 75%, 80%, 85%, 90%, 95%, 97%, 98%, 99%, or 100%) to the amino acid sequence of a *Clostridium difficile* 2-hydroxyacyl-CoA dehydratase encoded by HadBC (Genbank Accession Nos. AAV40819.1 and AAV40820.1, SEQ ID NO: 3 and SEQ ID NO:4, respectively) or an *Acidaminococcus fermentans* 2-hydroxyacyl-CoA dehydratase encoded by HdgAB (Genbank Accession Nos. CAA32465.1 and CAA32466.1, SEQ ID NO: 6 and SEQ ID NO:7, respectively). See, FIGS. 9A-9F.

A 2-hydroxyacyl-CoA dehydratase activator described herein can have at least 70% sequence identity (homology) (e.g., at least 75%, 80%, 85%, 90%, 95%, 97%, 98%, 99%, or 100%) to the amino acid sequence of a *Clostridium difficile* (Genbank Accession No. AAV40818.1, SEQ ID NO: 2) or an *Acidaminococcus fermentans* (Genbank Accession No. CAA42196.1, SEQ ID NO: 5) 2-hydroxyacyl-CoA dehydratase activator. See, FIGS. 9A-9F.

For example, a mevalonate diphosphate decarboxylase (MDD) described herein can have at least 70% sequence identity (homology) (e.g., at least 75%, 80%, 85%, 90%, 95%, 97%, 98%, 99%, or 100%) to the amino acid sequence of a *Streptococcus pyogenes* (Genbank Accession No. AAK33797.1, SEQ ID NO: 8), *Thioalkalimicrobium aerophilum* (Genbank Accession No. AHF01884.1, SEQ ID NO: 9), *Saccharomyces cerevisiae* (GenBank Accession No. CAA66158.1, SEQ ID NO:11), or *Streptococcus pneumonia* (GenBank Accession No. CAR68209.1, SEQ ID NO:10). See, FIGS. 9A-9F.

For example, a mevalonate 3-kinase described herein can have at least 70% sequence identity (homology) (e.g., at least 75%, 80%, 85%, 90%, 95%, 97%, 98%, 99%, or 100%) to the amino acid sequence of a *Thermoplasma acidophilum* (Genbank Accession No. CAC12426.1, SEQ ID NO: 12) mevalonate 3-kinase. See, FIGS. 9A-9F.

For example, a dehydratase described herein can have at least 70% sequence identity (homology) (e.g., at least 75%, 80%, 85%, 90%, 95%, 97%, 98%, 99%, or 100%) to the amino acid sequence of the linalool dehydratase from *Castellaniella defragrans* (GenBank Accession No. CBW30776.1, SEQ ID NO:13). See FIGS. 9A-9F.

For example, an acyl-ACP dehydrogenase described herein can have at least 70% sequence identity (homology) (e.g., at least 75%, 80%, 85%, 90%, 95%, 97%, 98%, 99%, or 100%) to the amino acid sequence of the acyl-CoA dehydrogenase from *Streptomyces kanamyceticus* (encoded by the tcsD gene) (GenBank Accession No. ADU56239.1, SEQ ID NO: 14). See, FIGS. 9A-9F.

For example, a monooxygenase described herein can have at least 70% sequence identity (homology) (e.g., at least 75%, 80%, 85%, 90%, 95%, 97%, 98%, 99%, or 100%) to the amino acid sequence of an *Aquincola tertiaricarbonis* monooxygenase encoded by mdpJ (Genbank Accession No. AER12131.1, SEQ ID NO: 15). See, FIGS. 9A-9F.

For example, a β-ketoacyl-ACP synthase described herein can have at least 70% sequence identity (homology) (e.g., at least 75%, 80%, 85%, 90%, 95%, 97%, 98%, 99%, or 100%) to the amino acid sequence of a *Streptomyces* sp. CNH189

(Genbank Accession No. AFY98994.1, SEQ ID NO: 18) β-ketoacyl-ACP-synthase. See, FIGS. 9A-9F.

For example, a sulfotransferase described herein can have at least 70% sequence identity (homology) (e.g., at least 75%, 80%, 85%, 90%, 95%, 97%, 98%, 99%, or 100%) to the amino acid sequence of a *Synechococcus* PCC 7002 (Genbank Accession No. ACA99172.1, SEQ ID NO: 19) or *Moorea producens* 19L (Genbank Accession No. ACV42478.1, SEQ ID NO: 20) sulfotransferase. See, FIGS. 9A-9F.

For example, a decarboxylating thioesterase described herein can have at least 70% sequence identity (homology) (e.g., at least 75%, 80%, 85%, 90%, 95%, 97%, 98%, 99%, or 100%) to the amino acid sequence of a *Moorea producens* 19L (Genbank Accession No. ACV42478.1, SEQ ID NO: 21) decarboxylating thioesterase. See, FIGS. 9A-9F.

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagluttanin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Recombinant hosts can naturally express none or some (e.g., one or more, two or more, three or more, four or more, five or more, or six or more) of the enzymes of the pathways described herein. Endogenous genes of the recombinant hosts also can be disrupted to prevent the formation of undesirable metabolites or prevent the loss of intermediates in the pathway through other enzymes acting on such intermediates. Recombinant hosts can be referred to as recombinant host cells, engineered cells, or engineered hosts. Thus, as described herein, recombinant hosts can include nucleic acids encoding one or more of a decarboxylase, a kinase, a dehydrogenase, a monooxygenase, an acyl [acyl carrier protein (acp)] dehydrogenase, a dehydratase, a thioesterase, or a decarboxylating thioesterase as described in more detail below.

In addition, the production of isoprene can be performed in vitro using the isolated enzymes described herein, using a lysate (e.g., a cell lysate) from a host microorganism as a source of the enzymes, or using a plurality of lysates from different host microorganisms as the source of the enzymes.

Production of Branched C5 Central Metabolite Backbones

In some embodiments, 3-methyl-pent-2-enoyl-CoA or 4-methyl-pent-2-enoyl-CoA is formed by a 2-hydroxyacyl-CoA dehydratase classified, for example, under EC 4.2.1.-, such as the gene product of HadBC (SEQ ID NO: 3 and SEQ ID NO:4) and its initiator HadI (SEQ ID NO: 2), or by the gene product of HgdAB (SEQ ID NO: 6 and SEQ ID NO:7) and its initiator HdgC (SEQ ID NO: 5). See, FIG. 2-5.

In some embodiments, the 2-hydroxyacyl-CoA dehydratase is the result of enzyme engineering. The 2-hydroxyacyl-CoA dehydratase enzymes isolated from anaerobic bacteria possess a common catalytic mechanism employed in amino acid degradation pathways. For example, the gene products of HadBC/HadI from *Clostridium difficile* catalyse the conversion of (R)-2-hydroxyisocaproyl-CoA to isocaprenoyl-CoA. Similarly, the gene products of HgdAB/HdgC catalyse the conversion of 2-hydroxyglutaryl-CoA to glutaconyl-CoA (Kim et al., *FEMS Microbiol. Reviews*, 2004, 28, 455-468). See FIGS. 2-5.

In some embodiments, a 3-hydroxy functional group is introduced into 3-methyl-pent-2-enoyl-CoA or 4-methyl-pent-2-enoyl-CoA by a (R)-specific enoyl-CoA hydratase enzyme classified, for example, under EC 4.2.1.119 such as the gene product of phaJ (SEQ ID NO: 16, Fukui et al., *J. Bacteriol.*, 1998, 180(3), 667-673) or MaoC (SEQ ID NO: 17; Park and Lee, *J. Bacteriol.*, 2003, 185(18), 5291-5397) or a bacterial (S)-specific enoyl-CoA hydratase classified, for example, under EC 4.2.1.17 such as the gene product of YsiB (SEQ ID NO: 1). See, for example, FIGS. 4 and 5.

In some embodiments, the enoyl-CoA hydratase enzyme is the result of enzyme engineering. A single enzyme candidate for the introduction of a 3-hydroxy functional group into 3-methylbuten-2-enoyl-CoA has been identified previously in the cell free extract of *Galactomyces reessii*, containing an enoyl-CoA hydratase, classified in EC 4.2.1.17, that converts 3-methylbuten-2-enoyl-CoA to 3-hydroxy-3-methylbutanoyl-CoA (Lee et al., *Appl. Environ. Microbiol.*, 1997, 63(11), 4191-4195). Equivalent enoyl-CoA hydratase activity from bacterial origin has not been identified. See FIG. 4 and FIG. 5.

In some embodiments, 4-methyl-3-oxopentanoyl-ACP is formed by condensing isobutyryl-CoA and malonyl-ACP using a β-ketoacyl-ACP-synthase enzyme classified, for example, under EC 2.3.1.- (e.g., EC 2.3.1.41, EC 2.3.1.79, or EC 2.3.1.80) such as the gene product of AnlF (SEQ ID NO: 18). It has been demonstrated that the gene product of anlF condenses isobutyryl-CoA and malonyl-ACP (Lechner et al., *ACS Synth. Biol.*, 2013, 2(7), 379-83). See, FIG. 6.

In some embodiments (FIG. 8), the central precursor to 3-methyl-3-hydroxypent-4-enoate, acetyl-CoA, is converted to acetoacetyl-CoA by an acetyl-CoA C-acetyltransferase classified, for example, under EC 2.3.1.9, followed by conversion to 3-hydroxy-3-methylglutaryl-CoA by a hydroxymethylglutaryl-CoA synthase classified, for example, under EC 2.3.3.10; followed by conversion to (R)-mevalonate by a hydroxymethylglutaryl-CoA reductase classified under EC 1.1.1.88 or EC 1.1.1.34; followed by conversion to 3-methyl-3-hydroxypent-4-enoate by an enzyme classified, for example, under EC 4.2.1.-such as an oleate hydratase, (e.g., a the gene product of ohyA (SEQ ID NO: 22) or a dehydratase classified under EC 4.2.1.- (such as one isolated from species such as *Aquincola tertiaricarbonis* or *Methylibium petroleiphilum* PM1).

In some embodiments, the dehydratase enzyme converting mevalonate to 3-methyl-3-hydroxypent-4-enoate is the result of enzyme engineering to improve activity or specificity using the structure and wild-type residue diversity of, for example, an oleate hydratase (SEQ ID NO: 22).

Enzymes Generating First Terminal Vinyl Group

Figure 2:
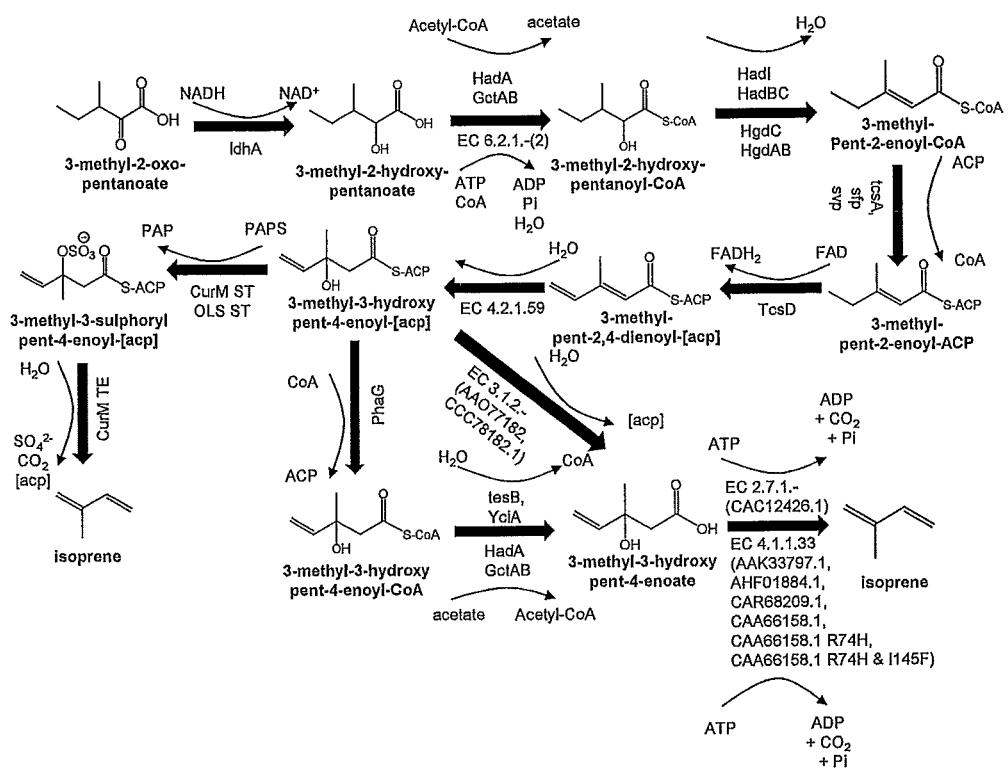
FIG. 2 is a schematic of exemplary biochemical pathways leading to isoprene using 3-methyl-2-oxopentanoate as a central precursor and an acyl ACP dehydrogenase.

In some embodiments, a first terminal vinyl group is introduced into 3-methyl-pent-2-enoyl-ACP, forming 3-methyl-pent-2,4-dienoyl-[acp] and then enzymatically converted in one or more steps to 3-methyl-3-hydroxypent-4-enoate or 3-methyl-3-sulphoryl-pent-4-enoyl-ACP (as shown, for example, in FIG. 2). It has been demonstrated that the gene product of tcsD (SEQ ID NO: 14) from *Streptomyces kanamyceticus* has dehydrogenase activity for straight and branch chain C5 acyl-ACP substrates (Mo et al., *JACS*, 2011, 133, 976-985). 3-methyl-pent-2-enoyl-ACP can be derived from the central metabolite 3-methyl-2-oxopentanoate.

Figure 3:
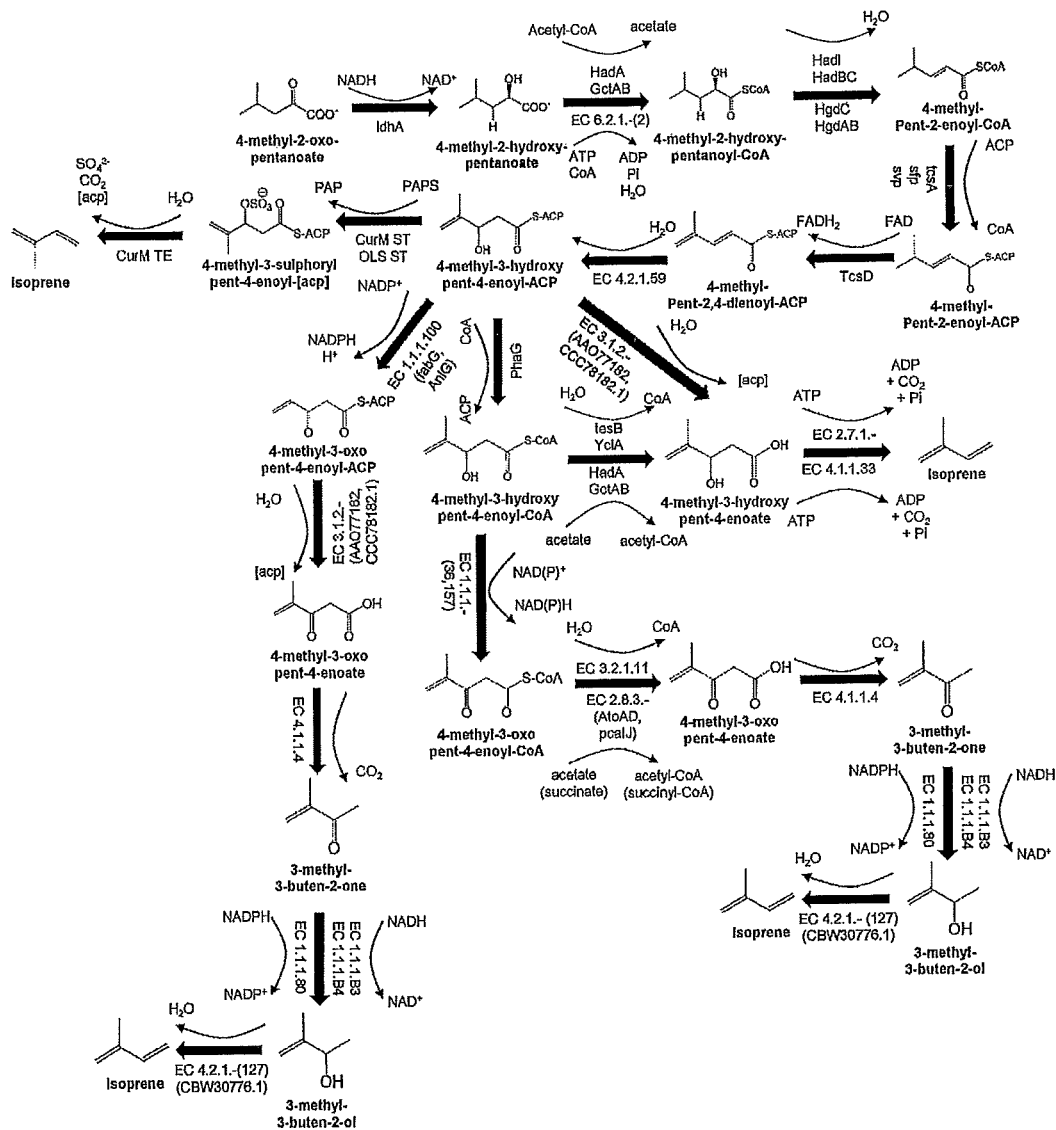
FIG. 3 is a schematic of exemplary biochemical pathways leading to isoprene using 4-methyl-2-oxopentanoate as a central precursor and an acyl-ACP dehydrogenase.
Figure 7:
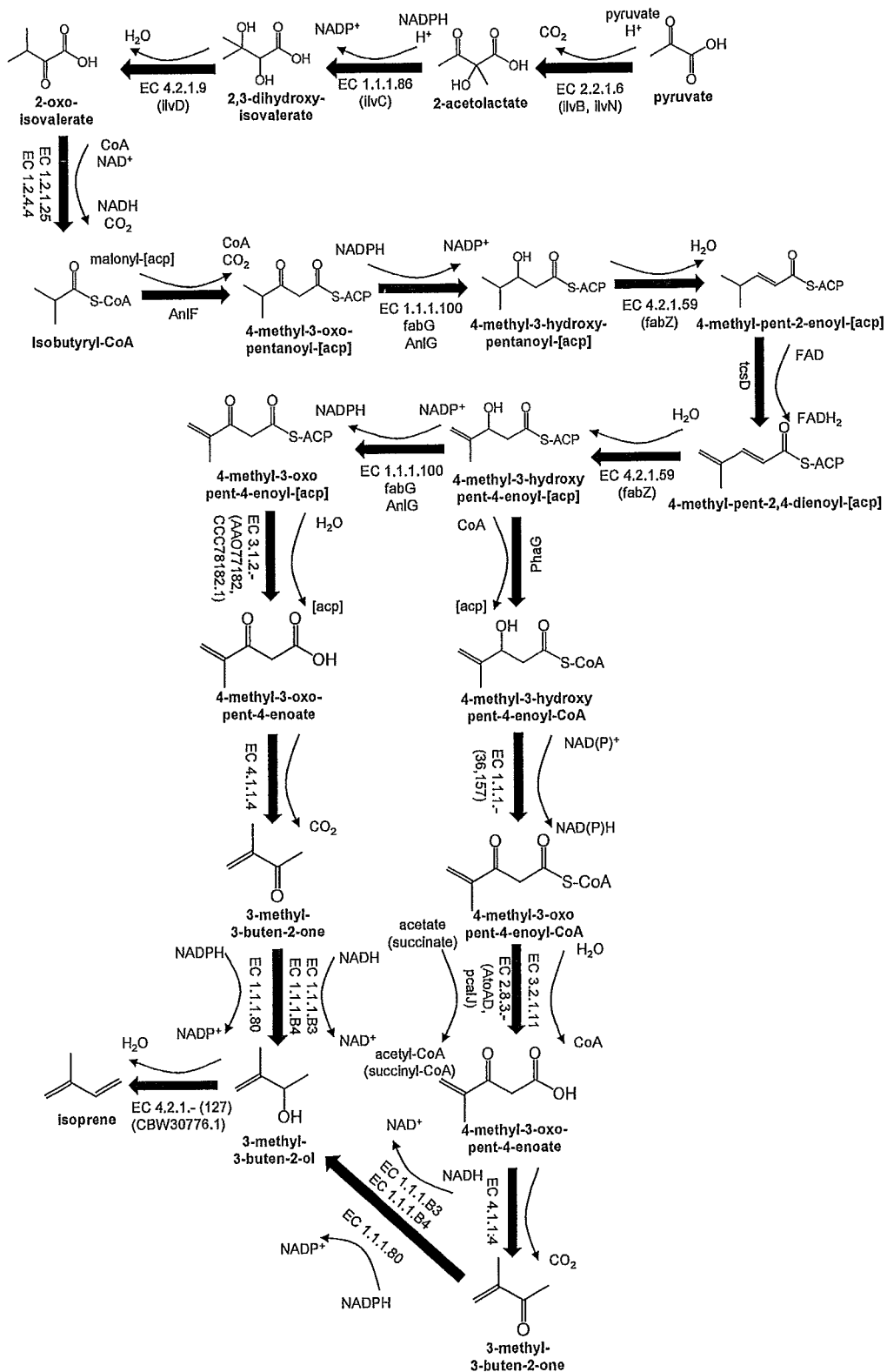
FIG. 7 is a schematic of exemplary biochemical pathways leading to isoprene using isobutyryl-CoA as a central precursor and an acyl ACP dehydrogenase to introduce the first vinyl group and a dehydratase, such as linalool dehydratase, to introduce the second vinyl group.

In some embodiments, a first terminal vinyl group is introduced into 4-methyl-pent-2-enoyl-[acp], forming 4-methyl-pent-2,4-dienoyl-[acp], which may be enzymatically converted in one or more steps to 4-methyl-3-hydroxypent-4-enoate (see, for example FIG. 3 and FIG. 6), 4-methyl-3-sulphoryl-pent-4-enoyl-ACP (see, for example, FIG. 3 and FIG. 6), or 3-methyl-3-buten-2-ol (see, for example, FIG. 3 and FIG. 7). It has been demonstrated that the gene product of tcsD (SEQ ID NO: 14) from *Streptomyces kanamyceticus* has dehydrogenase activity for 4-methyl-pent-2-enoyl-ACP (Mo et al., 2011, supra). 4-methyl-pent-2-enoyl-[acp] can be derived from the central metabolite 4-methyl-2-oxopentanoate or isobutyryl-CoA.

Figure 4:
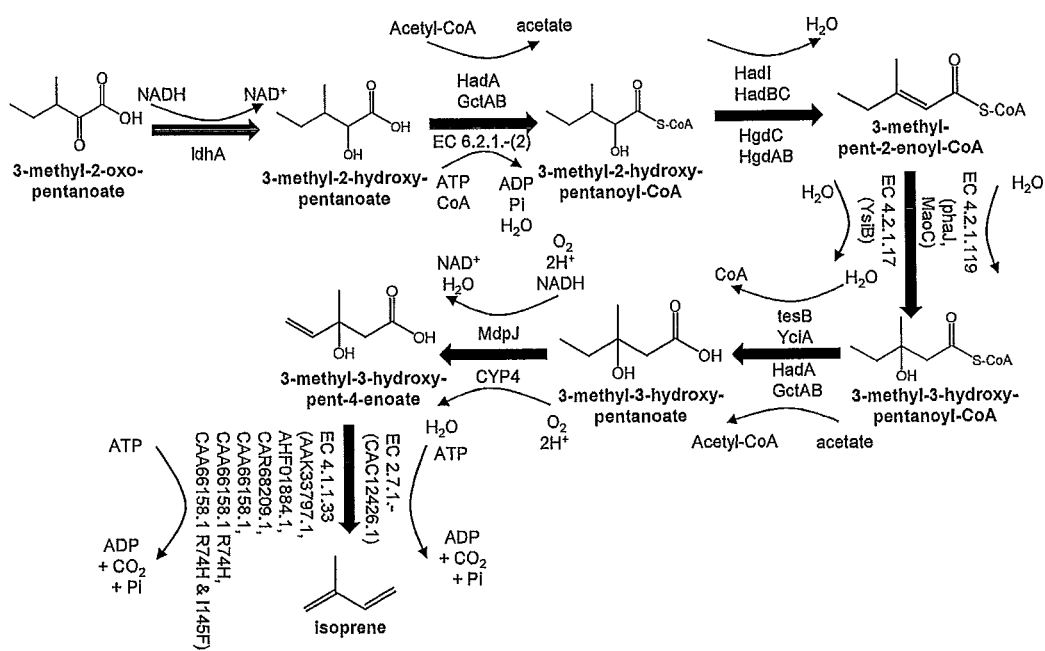
FIG. 4 is a schematic of an exemplary biochemical pathway leading to isoprene using 3-methyl-2-oxopentanoate as a central precursor and a monooxygenase.

In some embodiments, the first vinyl group is introduced into 3-methyl-3-hydroxy-pentanoate by a monooxygenase, forming 3-methyl-3-hydroxy-pent-4-enoate (see, for example, FIG. 4). It has been demonstrated that the monooxygenase encoded by mdpJ (SEQ ID NO: 15) introduces a terminal double bond into allyl groups bound to a secondary alcohol (Schäfer et al., *Appl. Environ. Microbiol.*, 2012, 78(17), 6280-6284).

Figure 5:
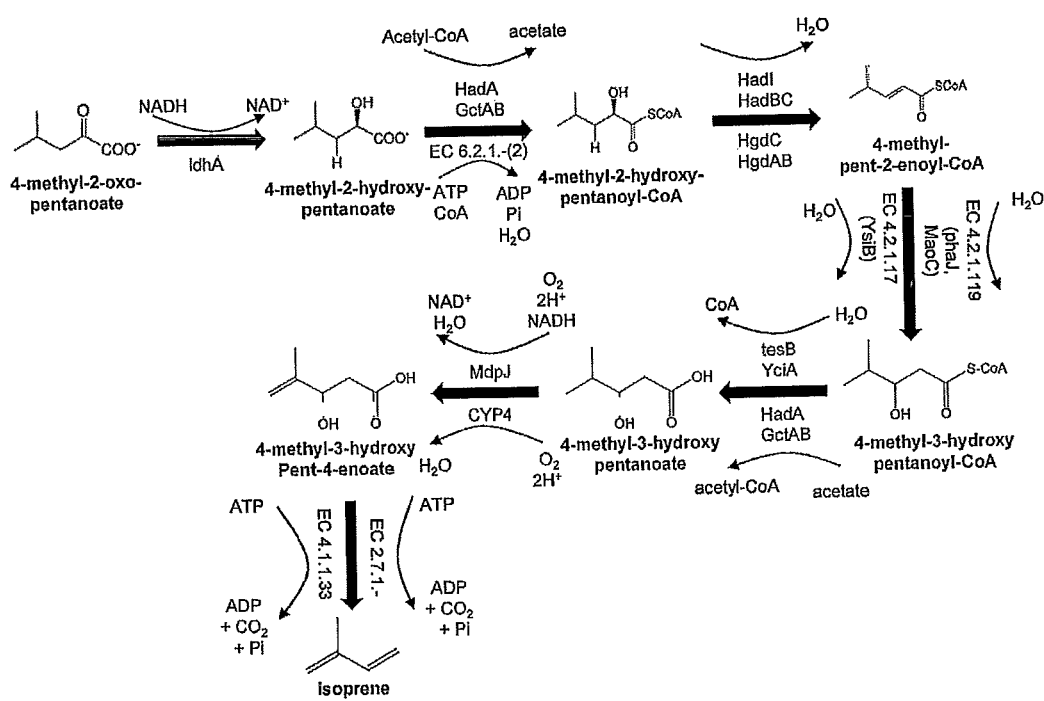
FIG. 5 is a schematic of an exemplary biochemical pathway leading to isoprene using 4-methyl-2-oxopentanoate as a central precursor and a monooxygenase.

In some embodiments, the first vinyl group is introduced into 4-methyl-3-hydroxypentanoate, forming 4-methyl-3-hydroxypent-4-enoate (see, for example, FIG. 5).

Figure 8:
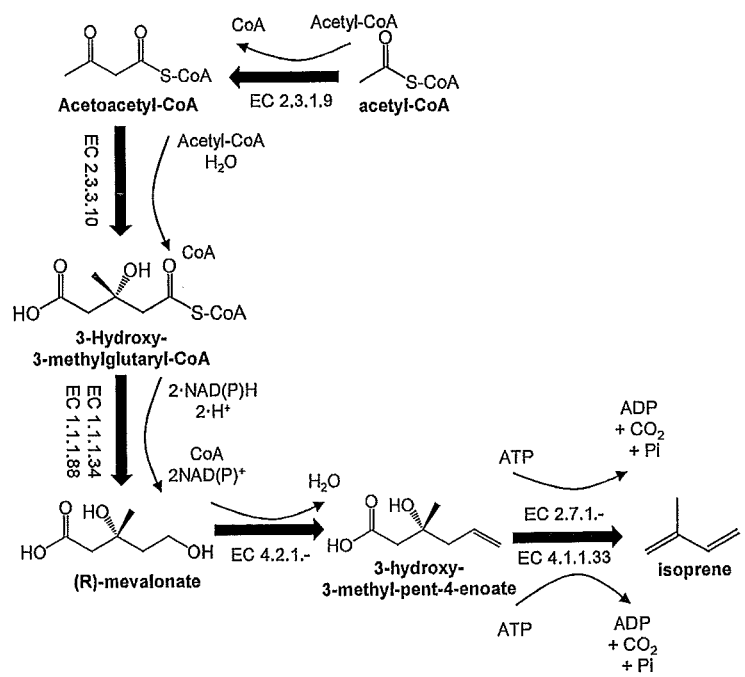
FIG. 8 is a schematic of an exemplary biochemical pathway leading to isoprene using (R)-mevalonate as a central precursor via 3-hydroxy-3-methyl-pent-4-enoate.

In some embodiments, the first vinyl group is introduced into mevalonate, forming 3-hydroxy-3-methyl-pent-4-enoate (as shown, for example, in FIG. 8).

Enzymes Generating Second Terminal Vinyl Group and Producing Isoprene

In some embodiments, the second vinyl group is introduced into a medium chain carbon alkenoate such as 3-methyl-3-hydroxypent-4-enoate or 4-methyl-3-hydroxypent-4-enoate by a GHMP superfamily enzyme such as a mevalonate diphosphate decarboxylase classified, for example, under EC 4.1.1.33 (e.g., SEQ ID NOs: 8-11) (Lefurgy et al., *J. Biol. Chem.*, 2010, 285(27), 20654-20663)) or a mevalonate 3-kinase classified, for example, under EC 2.7.1.- (e.g., SEQ ID NO: 12) (Vinokur et al., *Biochemistry*, 2014, 53(25), 4161-4168), producing isoprene (FIGS. 2-6 and 8). In some embodiments, a MDD has an amino acid substitution at one or both positions corresponding to amino acids 74 and/or 145 of the amino acid sequence set forth in SEQ ID NO:11. For example, a histidine residue can be substituted for arginine at a position aligning with residue 74 of SEQ ID NO:11 and/or a phenylalanine residue can be substituted for an isoleucine at a position aligning with residue 145 of SEQ ID NO:11. In some embodiments, a MDD has the amino acid sequence set forth in SEQ ID NO:11, except that a histidine is substituted at position 74 for arginine and/or a phenylalanine is substituted at position 145 for isoleucine.

In some embodiments, the second vinyl group is introduced into medium chain carbon alkenoate such as 3-methyl-3-sulphoryl-pent-4-enoyl-ACP or 4-methyl-3-sulphoryl-pent-4-enoyl-ACP by a decarboxylating thioesterase (e.g., from *Lyngbya majuscula* (CurM TE), *Moorea producens* (SEQ ID NO: 21), *Pseudomonas entomophila*, *H. ochraceum*, *Synechococcus* PCC 7002, *Cyanothece* PCC 7424 or *Cyanothece* PCC 7822) (see Gehret et al., *J. Biol. Chem.*, 2011, 286(16), 14445-14454), converting 3-methyl-3-sulphoryl-pent-4-enoyl-ACP or 4-methyl-3-sulphoryl-pent-4-enoyl-ACP to isoprene (see, FIG. 2, FIG. 3 and FIG. 6).

In some embodiments, the second vinyl group is introduced into a medium chain carbon alkenoate such as 3-methyl-3-buten-2-ol by a linalool dehydratase classified, for example, under EC 4.2.1.-such as EC 4.2.1.127 (SEQ ID NO: 13, GenBank Accession No. CBW30776.1, Brodkorb et al., *J. Biol. Chem.*, 2010, 285(40), 30436-30442) or a dehydratase classified under EC 4.2.1.-such as one isolated from a species such as *Aquincola tertiaricarbonis* or *Methylibium petroleiphilum* PM1; Schäfer et al., *Appl. Environ. Microbiol.*, 2011, 77(17), 5981-5987). See, FIG. 3 and FIG. 7.

Pathways to 3-Methyl-3-Hydroxypent-4-Enoyl-[Acp]

In some embodiments (FIG. 2), the central precursor to 3-methyl-3-hydroxypent-4-enoyl-[acp], 3-methyl-2-oxopentanoate, is converted to 3-methyl-2-hydroxypentanoate by a (R)-2-hydroxyacyl dehydrogenase classified, for example, under EC 1.1.1.272 such as the gene product of ldhA, followed by conversion to 3-methyl-2-hydroxy-pentanoyl-CoA by a CoA-transferase such as the gene product of HadA or GctAB (e.g., a glutaconate CoA transferase classified, for example, under EC 2.8.3.12) or a CoA-ligase classified, for example, under EC 6.2.1.- (e.g., EC 6.2.1.2); followed by conversion to 3-methyl-pent-2-enoyl-CoA by a (R)-2-Hydroxyacyl-CoA dehydratase such as the gene products of HadBC (SEQ ID NOs: 3 and 4) and the initiator HadI (SEQ ID NO: 2) or the gene products of HgdAB (SEQ ID NOs: 6 and 7) and the initiator HgdC (SEQ ID NO: 5); followed by conversion to 3-methyl-pent-2-enoyl-[acp] by an acyl transferase such as encoded by tcsA (see Genbank Accession No. ADU56236.1) or a 4' phosphopantetheinyl transferase such as encoded by sfp (see Genbank Accession No. CAA44858.1) or svp (see Genbank Accession No. AAG43513.1); followed by conversion to 3-methyl-pent-2,4-dienoyl-ACP by an acyl-[acp] dehydrogenase such as the gene product of TcsD (SEQ ID NO:14); followed by conversion to 3-methyl-3-hydroxypent-4-enoyl-ACP by a 3-hydroxyacyl-[acp] dehydratase classified, for example, under EC 4.2.1.59.

In some embodiments (FIG. 2), 3-methyl-3-hydroxypent-4-enoyl-[acp], a central precursor to 3-methyl-3-hydroxypent-4-enoate, is converted to 3-methyl-3-hydroxypent-4-enoyl-CoA by a (R)-3-hydroxyacyl-ACP: CoA transacylase such as the gene product of PhaG; followed by conversion to 3-methyl-3-hydroxypent-4-enoate by a CoA-tranferase such as the gene product of HadA or GctAB or by a thioesterase classified, for example, under EC 3.1.2.-such as the gene product of tesB (e.g., GenBank Accession No. AAA24665.1) or YciA (See Genbank Accession No. BAA14785.1).

In some embodiments (FIG. 2), 3-methyl-3-hydroxypent-4-enoyl-ACP, a central precursor to 3-methyl-3-hydroxypent-4-enoate, is converted to 3-methyl-3-hydroxypent-4-enoate by a thioesterase such as an acyl [acp] thioesterase (e.g., the gene product encoded by GenBank Accession No. AAO77182 or CCC78182.1).

In some embodiments (FIG. 2), 3-methyl-3-hydroxypent-4-enoyl-[acp], the central precursor to 3-methyl-3-sulphoryl-pent-4-enoyl-[acp], is converted to 3-methyl-3-sulphoryl-pent-4-enoyl-[acp] by a sulfotransferase classified under EC 2.8.2.-such as the gene product of CurM ST or OLS ST.

Pathways to 4-Methyl-3-Hydroxypent-4-Enoyl-[Acp]

In some embodiments (FIG. 3), the central precursor to 4-methyl-3-hydroxypent-4-enoyl-[acp], 4-methyl-2-oxopentanoate, is converted to 4-methyl-2-hydroxypentanoate by a (R)-2-hydroxyacyl dehydrogenase classified, for example, under EC 1.1.1.272 such as the gene product of ldhA, followed by conversion to 4-methyl-2-hydroxy-pentanoyl-CoA by a CoA-transferase such as the gene product of HadA or GctAB or a CoA-ligase such as classified under EC 6.2.1.- (2); followed by conversion to 4-methyl-pent-2-enoyl-CoA by a (R)-2-Hydroxyacyl-CoA dehydratase such as the gene products HadBC and the initiator HadI; followed by conversion to 4-methyl-pent-2-enoyl-[acp] by an acyl transferase such as the reaction with the gene product from TcsA & sfp/svp; followed by conversion to 4-methyl-pent-2,4-dienoyl-[acp] by an acyl-ACP dehydrogenase such as the gene product of TcsD; followed by conversion to 4-methyl-3-hydroxypent-4-enoyl-[acp] by a 3-hydroxyacyl-[acp] dehydratase classified, for example, under EC 4.2.1.59 such as the gene product of fabZ.

In some embodiments (FIG. 6), the central precursor to 4-methyl-3-hydroxypent-4-enoyl-[acp], isobutyryl-CoA, is converted to 4-methyl-3-oxo-pentanoyl-[acp] by a β-ketoacyl-[acp]-synthase such as the gene product of AnlF; followed by conversion to 4-methyl-3-hydroxy-pentanoyl-[acp] by a 3-oxoacyl-[acp] reductase (EC 1.1.1.100) such as the gene product of fabG or AnlG; followed by conversion to 4-methyl-pent-2-enoyl-[acp] by a 3-hydroxyacyl-[acp] dehydratase (EC 4.2.1.59) such as the gene product of fabZ; followed by conversion to 4-methyl-pent-2,4-dienoyl-[acp] by an acyl-[acp] dehydrogenase such as the gene product of tcsD; followed by conversion to 4-methyl-3-hydroxypent-4-enoyl-[acp] by a 3-hydroxyacyl-[acp] hydratase such as EC 4.2.1.59 such as the gene product of fabZ.

In some embodiments (FIG. 7), the central precursor to 4-methyl-3-hydroxypent-4-enoyl-[acp], isobutyryl-CoA, is converted to 4-methyl-3-oxo-pentanoyl-[acp] by a/1-ketoacyl-[acp]-synthase such as the gene product of AnlF; followed by conversion to 4-methyl-3-hydroxy-pentanoyl-[acp] by a 3-oxoacyl-[acp] reductase (EC 1.1.1.100) such as the gene product of fabG or AnlG; followed by conversion to 4-methyl-pent-2-enoyl-[acp] by a 3-hydroxyacyl-[acp]

dehydratase (EC 4.2.1.59) such as the gene product of fabZ; followed by conversion to 4-methyl-pent-2,4-dienoyl-[acp] by an acyl-[acp] dehydrogenase such as the gene product of tcsD; followed by conversion to 4-methyl-3-hydroxypent-4-enoyl-[acp] by a 3-hydroxyacyl-ACP hydratase such as EC 4.2.1.59 such as the gene product of fabZ.

Pathways to 3-Methyl-3-Hydroxypent-4-Enoate

In some embodiments (FIG. 2), the central precursor to 3-methyl-3-hydroxypent-4-enoate, 3-methyl-3-hydroxypent-4-enoyl-[acp], is converted to 3-methyl-3-hydroxypent-4-enoyl-CoA by a (R)-3-hydroxyacyl-[acp]:CoA transacylase such as the gene product of PhaG; followed by conversion to 3-methyl-3-hydroxypent-4-enoate by a CoA-transferase such as the gene product of HadA or GctAB or by a thioesterase such as the gene product of tesB (e.g., GenBank Accession No. AAA24665.1) or YciA (See Genbank Accession No. BAA14785.1).

In some embodiments (FIG. 2), the central precursor to 3-methyl-3-hydroxypent-4-enoate, 3-methyl-3-hydroxypent-4-enoyl-[acp], is converted to 3-methyl-3-hydroxypent-4-enoate by a thioesterase classified, for example, under EC 3.2.1.-such as the *Bacteroides thetaiotaomicron* acyl-[acp] thioesterase (GenBank Accession No. AAO77182) or *Lactobacillus plantarum* thioesterase (GenBank Accession No. CCC78182.1).

In some embodiments (FIG. 4), the central precursor to 3-methyl-3-hydroxypent-4-enoate, 3-methyl-2-oxo-pentanoate, is converted to 3-methyl-2-hydroxypentanoate by a (R)-2-hydroxyacyl dehydrogenase classified, for example, under EC 1.1.1.272 such as the gene product of ldhA, followed by conversion to 3-methyl-2-hydroxy-pentanoyl-CoA by a CoA-transferase such as the gene product of HadA or GctAB or a CoA-ligase such as classified under EC 6.2.1.- (e.g., EC 6.2.1.2); followed by conversion to 3-methyl-pent-2-enoyl-CoA by a (R)-2-Hydroxyacyl-CoA dehydratase such as the gene products of HadBC (SEQ ID NOs: 3 and 4) and the initiator HadI (SEQ ID NO:2) or the gene product HgdAB (SEQ ID NOs: 6 and 7) and the initiator HgdC (SEQ ID NO:5); followed by conversion to 3-methyl-3-hydroxypentanoyl-CoA by an enoyl-CoA hydratase such as the gene product of phaJ (SEQ ID NO:16), MaoC (SEQ ID NO: 17) or YsiB (SEQ ID NO: 1); followed by conversion to 3-methyl-3-hydroxypentanoate by a CoA-transferase such as the gene product of HadA or GctAB or a thioesterase such as the gene product of tesB (e.g., GenBank Accession No. AAA24665.1) or YciA (see Genbank Accession No. BAA14785.1); followed by conversion to 3-methyl-3-hydroxypent-4-enoate by a monooxygenase such as the gene product of MdpJ (SEQ ID NO: 15) or a cytochrome P450 such as the gene product of the CYP4 family.

In some embodiments, the enzymes shown in FIG. 4 are the result of enzyme engineering to improve activity or specificity using the enzyme structure and wild-type residue diversity to inform the rational enzyme design.

Pathways to 4-Methyl-3-Hydroxypent-4-Enoate

In some embodiments (FIG. 3 and FIG. 6), the central precursor to 4-methyl-3-hydroxypent-4-enoate, 4-methyl-3-hydroxypent-4-enoyl-[acp], is converted to 4-methyl-3-hydroxypent-4-enoyl-CoA by (R)-3-hydroxyacyl-[acp]:CoA transacylase such as the gene product of PhaG; followed by conversion to 4-methyl-3-hydroxypent-4-enoate by a CoA-tranferase such as the gene product of HadA or GctAB or by a thioesterase such as the gene product of tesB (e.g., GenBank Accession No. AAA24665.1) or YciA (see Genbank Accession No. BAA14785.1).

In some embodiments (FIG. 3 and FIG. 6), the central precursor to 4-methyl-3-hydroxypent-4-enoate, 4-methyl-3-hydroxypent-4-enoyl-[acp], is converted to 4-methyl-3-hydroxypent-4-enoate by a thioesterase classified, for example, under EC 3.2.1.-such as the *Bacteroides* thetaiotaomicron acyl-[acp] thioesterase (GenBank Accession No. AAO77182) or *Lactobacillus plantarum* thioesterase (GenBank Accession No. CCC78182.1).

In some embodiments (FIG. 5), the central precursor to 4-methyl-3-hydroxypent-4-enoate, 4-methyl-2-oxo-pentanoate, is converted to 4-methyl-2-hydroxypentanoate by a (R)-2-hydroxyacyl dehydrogenase classified, for example, under EC 1.1.1.272 such as the gene product of ldhA, followed by conversion to 4-methyl-2-hydroxy-pentanoyl-CoA by a CoA-transferase such as the gene product of HadA or GctAB or a CoA-ligase classified, for example, under EC 6.2.1.- (e.g., EC 6.2.1.2); followed by conversion to 4-methyl-pent-2-enoyl-CoA by a (R)-2-Hydroxyacyl-CoA dehydratase such as the gene products of HadBC (SEQ ID NOs: 3 and 4) and the initiator HadI (SEQ ID NO: 2) or the gene products of HgdAB (SEQ ID NO: 6 and 7) and the initiator HgdC (SEQ ID NO:5); followed by conversion to 4-methyl-3-hydroxypentanoyl-CoA by an enoyl-CoA hydratase such as the gene product of phaJ (SEQ ID NO: 16), MaoC (SEQ ID NO: 17) or YsiB (SEQ ID NO: 1); followed by conversion to 4-methyl-3-hydroxypentanoate by a CoA-transferase such as the gene product of HadA or GctAB or a thioesterase such as the gene product of tesB (e.g., GenBank Accession No. AAA24665.1) or YciA (e.g., Genbank Accession No. BAA14785.1); followed by conversion to 4-methyl-3-hydroxypent-4-enoate by a monooxygenase such as the gene product of MdpJ (SEQ ID NO: 15) or a cytochrome P450 such as the gene product of the CYP4 family.

In some embodiments, the enzymes shown in FIG. 5 are the result of enzyme engineering to improve activity or specificity using the enzyme structure and wild-type residue diversity to inform the rational enzyme design.

Pathway to 4-Methyl-3-Sulphoryl-Pent-4-Enoyl-[Acp]

In some embodiments, the central precursor to 4-methyl-3-sulphoryl-pent-4-enoyl-[acp], 4-methyl-3-hydroxypent-4-enoyl-[acp], is converted to 4-methyl-3-sulphoryl-pent-4-enoyl-[acp] by a sulfotransferase such as the gene product of CurM ST or OLS ST. See, FIG. 3 and FIG. 6.

Pathways to 3-Methyl-3-Buten-2-Ol

In some embodiments (e.g., FIG. 3 and FIG. 7), the central precursor to 3-methyl-3-buten-2-ol, 4-methyl-3-hydroxypent-4-enoyl-[acp], can be converted to 4-methyl-3-hydroxypent-4-enoyl-[acp] by (R)-3-hydroxyacyl-[acp]: CoA transacylase such as the gene product of PhaG; followed by conversion to 4-methyl-3-oxopent-4-enoyl-CoA by a dehydrogenase classified, for example under EC 1.1.1.-such as EC 1.1.1.36 or EC 1.1.1.157); followed by conversion to 4-methyl-3-oxopent-4-enoate by a thio-esterase classified for example, under EC 3.2.1.11 or a CoA-transferase classified under EC 2.8.3.-encoded by AtoAD or pcaIJ; followed by conversion to 3-methyl-3-buten-2-one by an acetoacetate decarboxylase classified, for example, under EC 4.1.1.4; followed by conversion to 3-methyl-3-buten-2-ol by a secondary alcohol dehydrogenase, classified, for example, under EC 1.1.1.B3, EC 1.1.1.B4 or EC 1.1.1.80.

In some embodiments (e.g., FIG. 3 and FIG. 7), the central precursor to 3-methyl-3-buten-2-ol, 4-methyl-3-hydroxypent-4-enoyl-[acp], can be converted to 4-methyl-3-oxopent-4-enoyl-[acp] by a 3-oxoacyl-[acp] reductase such as an enzyme classified under EC 1.1.1.100 (e.g., the gene product of fabG or AnlG); following by conversion to 4-methyl-3-oxopent-4-enoate by a thioesterase classified, for example, under EC 3.1.2.-such as the *Bacteroides thetaiotaomicron* acyl-[acp] thioesterase (GenBank Accession No. AAO77182) or *Lactobacillus plantarum* thioesterase (GenBank Accession No. CCC78182.1); followed by conversion to 3-methyl-3-buten-one by an acetoacetate decarboxylase classified, for example, under EC 4.1.1.4; followed by conversion to 3-methyl-3-buten-2-ol by a secondary alcohol dehydrogenase, classified, for example, under EC 1.1.1.B3, EC 1.1.1.B4 or EC 1.1.1.80.

In some embodiments, the enzymes shown in FIG. 3 and FIG. 7 are the result of enzyme engineering to improve activity or specificity using the enzyme structure and wild-type residue diversity to inform the rational enzyme design.

In some embodiments, the enzymes shown in FIG. 3 and FIG. 7 are the result of enzyme engineering to improve activity or specificity using the enzyme structure and wild-type residue diversity to inform the rational enzyme design.

Cultivation Strategies

In some embodiments, the nucleic acids encoding the enzymes of the pathways described in FIGS. 2-8 are introduced into a host microorganism that is either a prokaryote or eukaryote.

For example, the prokaryote can be a bacterium from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus* necator or *Cupriavidus metallidurans*; from the genus *Pseudomonas* such as *Pseudomonas fluorescens*, *Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing isoprene or precursors thereof.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing isoprene or precursors thereof.

In some embodiments, isoprene is biosynthesized in a recombinant host using a fermentation strategy that can include anaerobic, micro-aerobic or aerobic cultivation of the recombinant host.

In some embodiments, isoprene is biosynthesized in a recombinant host using a fermentation strategy that uses an alternate final electron acceptor to oxygen such as nitrate.

In some embodiments, a cell retention strategy using, for example, ceramic hollow fiber membranes can be employed to achieve and maintain a high cell density during either fed batch or continuous fermentation in the synthesis of isoprene.

In some embodiments, the biological feedstock can be, can include, or can derive from, monosaccharides, disaccharides, lignocellulose, hemicellulose, cellulose, lignin, levulinic acid & formic acid, triglycerides, glycerol, fatty acids, agricultural waste, condensed distillers' solubles or municipal waste.

The efficient catabolism of crude glycerol stemming from the production of biodiesel has been demonstrated in several microorganisms such as *Escherichia coli*, *Cupriavidus necator*, *Pseudomonas oleavorans*, *Pseudomonas putida* and *Yarrowia lipolytica* (Lee et al., *Appl. Biochem. Biotechnol.*, 2012, 166, 1801-1813; Yang et al., *Biotechnology for Biofuels*, 2012, 5:13; Meijnen et al., *Appl. Microbiol. Biotechnol.*, 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology*, 2011, 155, 2011, 293-298; Martin and Prather, *Journal of Biotechnology*, 2009, 139, 61-67).

The efficient catabolism of lignin-derived aromatic compounds such benzoate analogues has been demonstrated in several microorganisms such as *Pseudomonas putida*, *Cupriavidus* necator (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7), 2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli*, *Corynebacterium glutamicum* and *Lactobacillus delbrueckii* and *Lactococcus lactis* (see, e.g., Hermann et al, *Journal of Biotechnology*, 2003, 104, 155-172; Wee et al., *Food Technol. Biotechnol.*, 2006, 44(2), 163-172; Ohashi et al., *Journal of Bioscience and Bioengineering*, 1999, 87(5), 647-654).

The efficient utilization of furfural, derived from a variety of agricultural lignocellulosic sources, has been demonstrated for *Cupriavidus necator* (Li et al., *Biodegradation*, 2011, 22, 1215-1225).

In some embodiments, the non-biological feedstock can be or can derive from natural gas, syngas, $CO_2/H_2$, methanol, ethanol, benzoic acid, non-volatile residue (NVR) or a caustic wash waste stream from cyclohexane oxidation processes, or terephthalic acid/isophthalic acid mixture waste streams.

The efficient catabolism of methanol has been demonstrated for the methylotropic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Köpke et al., *Applied and Environmental Microbiology*, 2011, 77(15), 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1), 152-156).

In some embodiments, substantially pure cultures of recombinant host microorganisms are provided. As used herein, a "substantially pure culture" of a recombinant host microorganism is a culture of that microorganism in which less than about 40% (i.e., less than about 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the recombinant microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of recombinant microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

Metabolic Engineering

The present document provides methods involving less than all the steps described for all the above pathways. Such methods can involve, for example, one, two, three, four, five, six, seven, eight, nine, ten, or more of such steps. Where less than all the steps are included in such a method, the first step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein can be the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined herein can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to isoprene.

Attenuation strategies include, but are not limited to, the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to isoprene.

In some embodiments using hosts that naturally accumulate polyhydroxyalkanoates, the polymer synthase enzymes can be attenuated in the host strain.

In some embodiments, the enzymes from the mevalonate pathway, for example, EC 2.3.1.9, EC 2.3.3.10, EC 1.1.1.34 or EC 1.1.1.88, are introduced or gene dosed into a host microorganism that utilizes the non-mevalonate or 2-C-methyl-D-erythritol 4-phosphate pathway for isoprenoid synthesis.

In some embodiments, the enzymes from the non-mevalonate or 2-C-methyl-D-erythritol 4-phosphate pathway leading to isoprenoid synthesis are introduced into a host microorganism that utilizes the mevalonate pathway for isoprenoid synthesis and EC 2.7.1.36 is attenuated.

In some embodiments, the enzymes responsible for 3'-Phosphoadenosine-5'-phosphosulfate (PAPS) synthesis classified under EC 2.7.7.4 & EC 2.7.1.25 are constitutively expressed in the host organisms.

In some embodiments requiring the intracellular availability of pyruvate for isoprene synthesis, a gene in an acetate synthesis pathway encoding an acetate kinase, such as ack, can be attenuated (Shen et al., *Appl. Environ. Microbiol.*, 2011, 77(9), 2905-2915).

In some embodiments requiring the intracellular availability of pyruvate for isoprene synthesis, a gene encoding the degradation of pyruvate to lactate such as ldhA can be attenuated (Shen et al., *Appl. Environ. Microbiol.*, 2011, 77(9), 2905-2915).

In some embodiments requiring the intracellular availability of pyruvate for isoprene synthesis, a gene encoding the degradation of phosphoenolpyruvate to succinate such as frdBC can be attenuated (see, e.g., Shen et al., 2011, supra).

In some embodiments requiring the intracellular availability of pyruvate for isoprene synthesis, a gene encoding the degradation of acetyl-CoA to ethanol such as adhE can be attenuated (Shen et al., 2011, supra).

In some embodiments, where pathways require excess NADPH co-factor in the synthesis of isoprene, a puridine nucleotide transhydrogenase gene such as UdhA can be overexpressed in the host organism (Brigham et al., *Advanced Biofuels and Bioproducts*, 2012, Chapter 39, 1065-1090).

In some embodiments, where pathways require excess NADPH co-factor in the synthesis of isoprene, a glyceraldehyde-3P-dehydrogenase gene such as GapN can be overexpressed in the host organism (Brigham et al., 2012, supra).

In some embodiments, where pathways require excess NADPH co-factor in the synthesis of isoprene, a malic enzyme gene such as maeA or maeB can be overexpressed in the host organism (Brigham et al., 2012, supra).

In some embodiments, where pathways require excess NADPH co-factor in the synthesis of isoprene, a glucose-6-phosphate dehydrogenase gene such as zwf can be overexpressed in the host organism (Lim et al., *Journal of Bioscience and Bioengineering*, 2002, 93(6), 543-549).

In some embodiments, where pathways require excess NADPH co-factor in the synthesis of isoprene, a fructose 1,6 diphosphatase gene such as fbp can be overexpressed in the host (Becker et al., *Journal of Biotechnology*, 2007, 132, 99-109).

In some embodiments, a feedback inhibition resistant mutant of an acetolactate synthase classified, for example, under EC 2.2.1.6, such as mutants of ilvB and/or ilvN that are resistant to feedback inhibition by lysine and leucine, can be overexpressed in the host.

In some embodiments, acetolactate synthase can be expressed under a promoter not subject to genetic repression by branch-chain amino acids (e.g., valine, leucine, or isoleucine).

In some embodiments, the efflux of isoprene across the cell membrane to the extracellular media can be enhanced or amplified by genetically engineering structural modifications to the cell membrane or increasing any associated transporter activity for isoprene.

Producing Isoprene Using a Recombinant Host

Typically, isoprene is produced by providing a host microorganism and culturing the provided microorganism with a culture medium containing a suitable carbon source as described above. In general, the culture media and/or culture conditions can be such that the microorganisms grow to an adequate density and produce isoprene efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of isoprene. Once produced, any method can be used to isolate isoprene.

Once produced, any method can be used to isolate isoprene. For example, isoprene can be recovered from the fermenter off-gas stream as a volatile product as the boiling point of isoprene is 34.1° C. At a typical fermentation temperature of approximately 30° C., isoprene has a high vapour pressure and can be stripped by the gas flow rate through the broth for recovery from the off-gas. Isoprene can be selectively adsorbed onto, for example, an adsorbent and separated from the other off-gas components. Membrane separation technology may also be employed to separate isoprene from the other off-gas compounds. Isoprene may desorbed from the adsorbent using, for example, nitrogen and condensed at low temperature and high pressure.

EXAMPLES

Example 1

Enzyme Activity of R-Specific Enoyl-CoA Hydratase Accepting 3-Methyl-3-Hydroxypentanoyl-CoA and 4-Methyl-3-Hydroxypentanoyl-CoA as Substrate The C-terminal his-tagged phaJ gene (SEQ ID NO: 16) from *Aeromonas punctata* was cloned into a pE23a expression vector under the T7 promoter. The expression vector was transformed into a BL21[DE3] *E. coli* host.

The resulting recombinant *E. coli* strain was cultivated in a 1L shake flask culture containing 100 mL Luria Broth media at 30° C., shaking at 200 rpm. The culture was induced using 1 mM IPTG for 2 h.

The pellet from each of the induced shake flask cultures was harvested by centrifugation. The pellet was resuspended in 20 mM HEPES (pH=7.2), 1 mM PMSF and 29U benzonase. The resuspended pellet was lysed via sonication. The cell debris was separated from the supernatant via centrifugation and filtered using a 0.2 μm filter.

The phaJ enzyme was purified from the supernatant using Ni-affinity chromatography and concentrated to 1.25 mg/mL.

Figure 10:
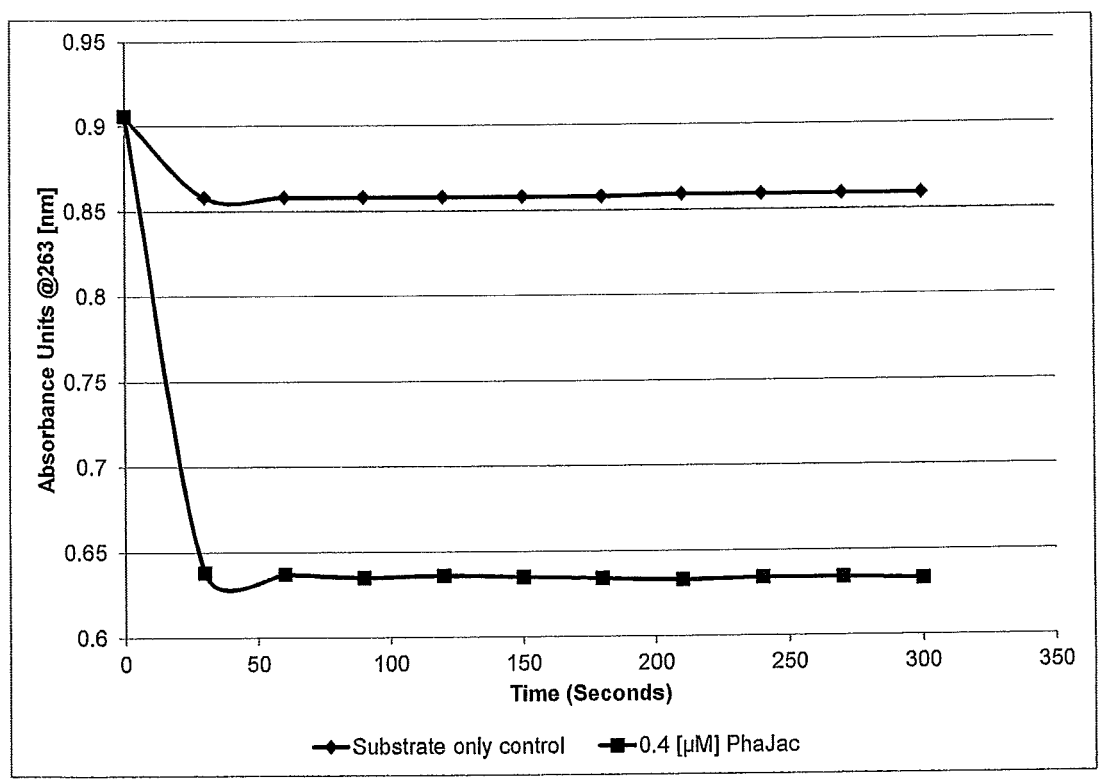
FIG. 10 is a graph of the results from a spectrophotometric enzyme assay for enoyl-CoA hydratase (encoded by phaJ) activity in the forward direction, accepting crotonyl-CoA as substrate.

The native enzyme activity assay in the forward (hydration) direction was undertaken in a buffer composed of 10 mM ammonium acetate (pH=8) and 1 mM of crotonyl-CoA from Sigma-Aldrich at 30° C. The enzyme activity assay reaction was initiated by adding 0.4 μM of purified enoyl-CoA hydratase to the assay buffer containing the substrate. The enzyme encoded by phaJ accepted crotonyl-CoA as substrate as confirmed via spectrophotometry at 263 nm at 30° C. The substrate only control showed minimal spontaneous hydration of crotonyl-CoA as determined by spectrophotometry at 263 nm. See FIG. 10.

The native enzyme activity assay in the reverse (dehydration) direction was undertaken in a buffer composed of 10 mM ammonium acetate (pH=8) and 1 mM of racemic 3-hydroxybutanoyl-CoA. The enzyme activity assay reaction was initiated by adding 5 μM of purified enoyl-CoA hydratase to the assay buffer containing the substrate and incubated at 30° C. for 1 h. The enzyme encoded by phaJ accepted 3-hydroxybutanoyl-CoA as substrate as confirmed via LC-MS. The substrate only control showed negligible spontaneous dehydration of 3-hydroxybutanoyl-CoA. As demonstrated previously (Lan and Liao, PNAS, 2012, 109 (16), 6018-6023), the enoyl-CoA hydratase encoded by phaJ is reversible, though favors the forward (hydration) direction. See FIG. 11.

The non-native enzyme activity assay in the reverse (dehydration) direction was undertaken in a buffer composed of 10 mM ammonium acetate (pH=8) and 1 mM of 3-methyl-3-hydroxypentanoyl-CoA. The enzyme activity assay reaction was initiated by adding 5 μM of purified enoyl-CoA hydratase to the assay buffer containing the substrate and incubated at 30° C. for 1 h. The enzyme encoded by phaJ accepted 3-methyl-3-hydroxypentanoyl-CoA as substrate as confirmed via LC-MS. The substrate only control showed no spontaneous dehydration of 3-methyl-3-hydroxypentanoyl-CoA. See FIG. 12.

The non-native enzyme activity assay in the reverse (dehydration) direction was undertaken in a buffer composed of 10 mM ammonium acetate (pH=8) and 1 mM of 4-methyl-3-hydroxypentanoyl-CoA. The enzyme activity assay reaction was initiated by adding 5 μM of purified enoyl-CoA hydratase to the assay buffer containing the substrate and incubated at 30° C. for 1 h. The enzyme encoded by phaJ accepted 4-methyl-3-hydroxypentanoyl-CoA as substrate as confirmed via LC-MS. The substrate only control showed no spontaneous dehydration of 4-methyl-3-hydroxypentanoyl-CoA. See FIG. 13.

The enoyl-CoA hydratase encoded by phaJ from *Aeromonas punctata* accepted 3-methyl-3-hydroxypentanoyl-CoA and 4-methyl-3-hydroxypentanoyl-CoA as substrate in the dehydration direction. Given the reversibility of the enzyme reaction and the favoured hydration direction, the enoyl-CoA hydratase encoded by phaJ from *Aeromonas punctata* accepts 3-methyl-pent-2-enoyl-CoA and 4-methyl-pent-2-enoyl-CoA as substrate.

Example 2

Enzyme Activity of GHMP Superfamily Enzymes, Mevalonate Diphosphate Decarboxylase and Mevalonate-3-Kinase, Accepting 3-Methyl-3-Hydroxypent-4-Enoate as Substrate, Forming Isoprene Each of the sequences encoding a C-terminal His-tagged gene encoding the mevalonate diphosphate decarboxylase of SEQ ID NOs: 8, 9, 10, and 11 respectively (see FIGS. 9A-9F) and the mevalonate 3-kinase of SEQ ID NO: 12 (see FIGS. 9A-9F) was cloned into a PD681-CH expression vector under control of the rhapBAD promoter, such that a C-terminal HIS tagged GHMP superfamily enzyme could be produced. Each expression vector was transformed into a BL21[DE3] *E. coli* host. The resulting recombinant *E. coli* strains were cultivated at 37° C. in a 5L shake flask culture containing 1L Luria Broth (LB) media and kanamycin antibiotic selection pressure, with shaking at 90 rpm. At an $OD_{600}$ between 0.6 to 0.8, the culture was induced with L-rhamnose to a final concentration of 2 g/L. The cultures was induced for 6 h at 37° C. The pellets from the induced shake flask cultures were harvested via centrifugation and stored at –20° C.

Each frozen pellet was thawed, resuspended and lysed in a lysis buffer containing 50 mM Tris.HCl (pH=8.0), 50 mM NaCl, 1 mM $MgCl_2$ 1% (w/v) Triton X-100, 1 mg/mL lysozyme and 10 U/mL benzonase for 1 h at 30° C. The cell debris was removed via centrifugation. The GHMP superfamily enzymes were purified from the resulting supernatant using Ni-affinity chromatography and the eluate was buffer exchanged and concentrated via ultrafiltration (10 kDa MWCO) into 100 mM HEPES (pH=7.0), 100 mM KCl to a final enzyme concentration of 200 µM.

Figure 14:
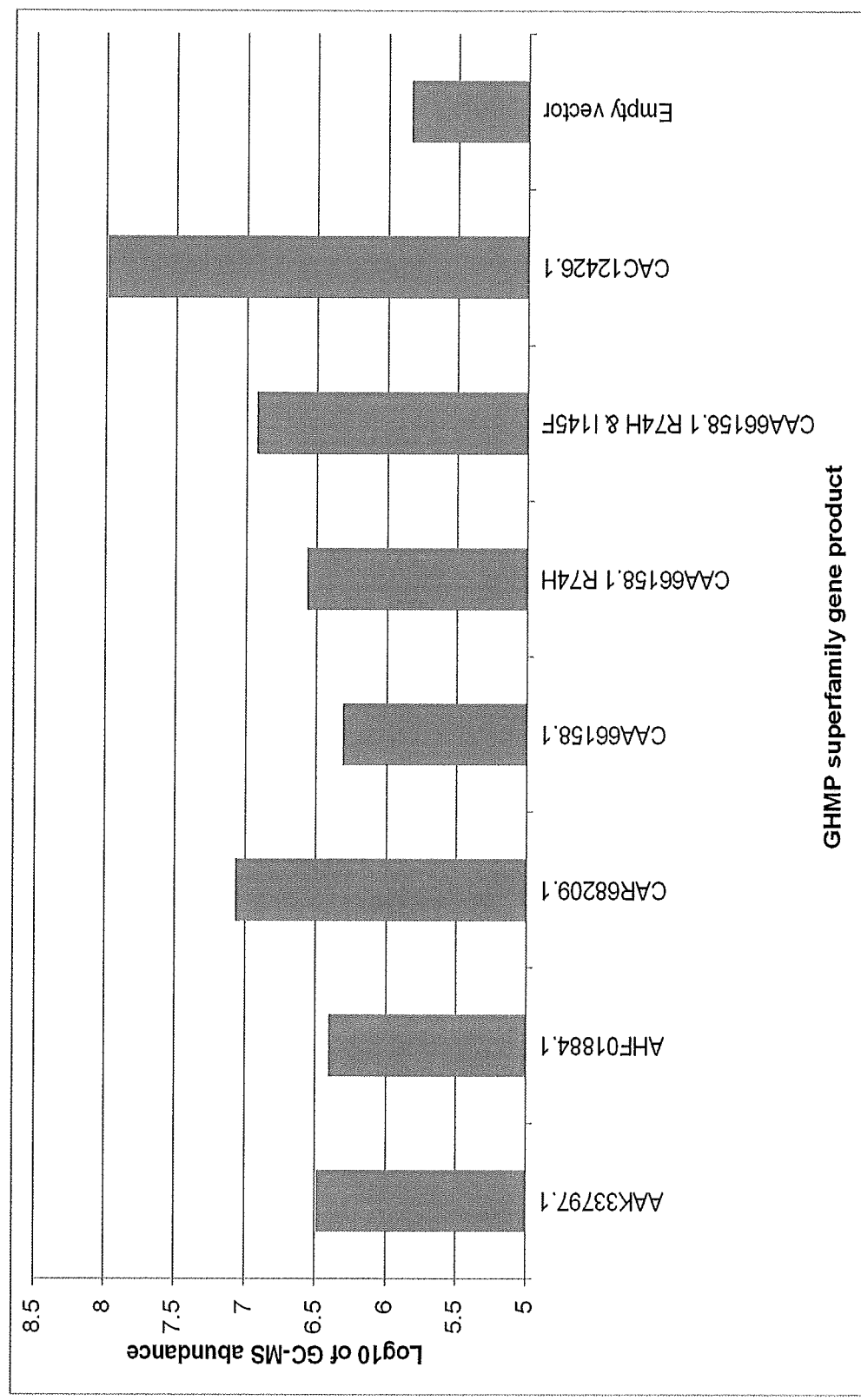
FIG. 14 is a bar graph of the logarithmic GC-MS species abundance for GHMP superfamily enzymes (AAK33797.1, SEQ ID NO: 8; AHF01884.1, SEQ ID NO: 9; CAR68209.1, SEQ ID NO: 10; CAA66158.1, SEQ ID NO: 11; CAA66158.1 having a histidine at position 74 instead of arginine; CAA66158.1 having a histidine at position 74 instead of arginine and a phenylalanine at position 145 instead of isoleucine; CAC12426.1, SEQ ID NO: 12) converting 3-methyl-3-hydroxypent-4-enoate to isoprene relative to the empty vector control.

Each enzyme activity assay was performed in an assay buffer composed of 100 mM HEPES (pH=7.0), 100 mM KCl, 30 mM $MgCl_2$, 30 mM ATP, 2 mM DTT and 10 mM of 3-methyl-3-hydroxypent-4-enoate as substrate. Each enzyme activity assay reaction was initiated by adding 0.5 mL of the enzyme stock of SEQ ID NOs: 8, 9, 10, 11 or 12 to 0.5 mL of assay buffer in a 10 mL crimped glass vial and incubating at 30° C. for 24 h. The headspace of each glass vial was analysed by GC-MS for isoprene and compared to the empty vector control. The gene product of SEQ ID NOs: 8, 9, 10, 11 and 12 accepted 3-methyl-3-hydroxypent-4-enoate as substrate as confirmed via GC-MS (see FIG. 14) and synthesized isoprene as reaction product.

Example 3

Enzyme Activity of Linalool Dehydratase Accepting 3-Methyl-3-Buten-2-Ol as Substrate, Forming Isoprene A sequence encoding a C-terminal His-tag encoding the linalool dehydratase of SEQ ID NO: 13 (see FIGS. 9A-9F) was cloned into a pET15 expression vector under control of the T7 promoter such that a C-terminal HIS tagged enzyme could be produced. The expression vector was transformed into a BL21[DE3] *E. coli* host. The resulting recombinant *E. coli* strain was cultivated at 30° C. in a 1L shake flask culture containing 100 mL Auto-Induction media and antibiotic selection pressure, shaking at 220 rpm overnight. The pellet from the induced shake flask culture was harvested via centrifugation and used immediately in a whole cell assay.

Figure 15:
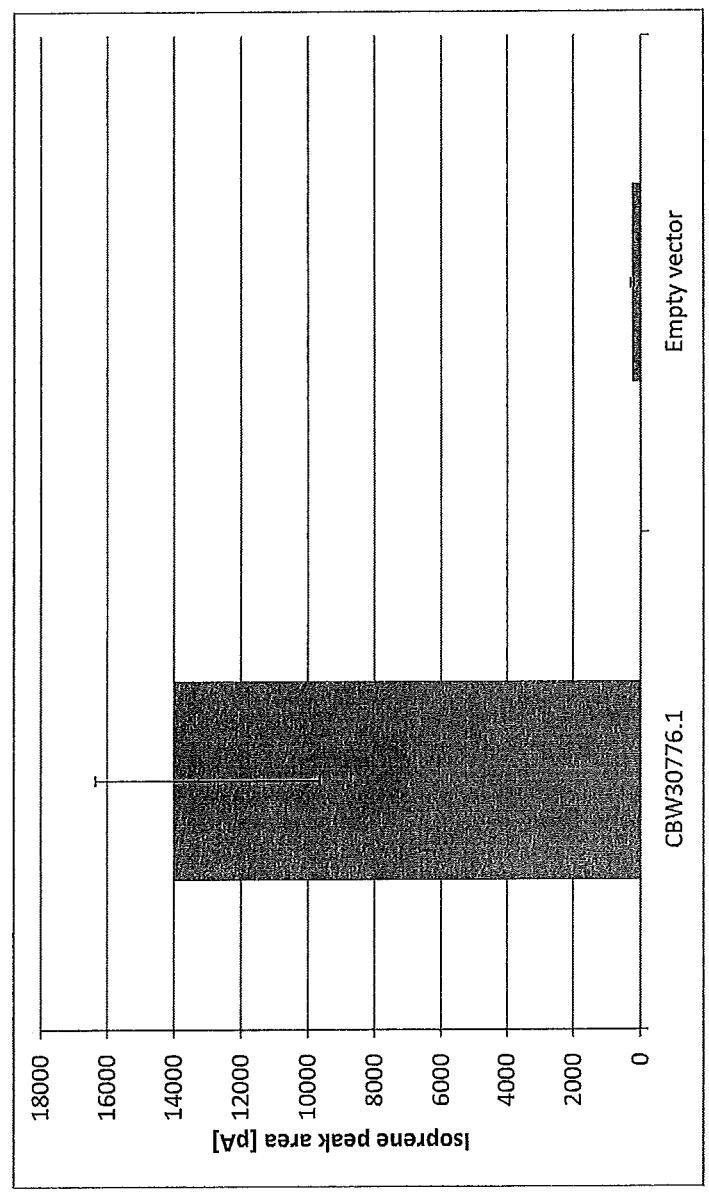
FIG. 15 is a bar graph of the GC-MS peak area for linalool dehydratase (CBW30776.1, SEQ ID NO: 13) converting 3-methyl-3-buten-2-ol to isoprene relative to the empty vector control.

The pellet was washed and resuspended in M9 minimal media to 160 mg/mL (wet weight) and dispensed into 10 mL crimped glass vials in triplicate. The substrate 3-methyl-3-buten-2-ol was added to a final concentration of 20 mM and incubated at 30° C. at 220 rpm for 48 h. The headspace of each glass vial was analysed by GC-MS for isoprene and compared to the empty vector control (undertaken in triplicate). The gene product of SEQ ID NO: 13 accepted 3-methyl-3-buten-2-ol as substrate as confirmed via GC-MS (see FIG. 15) and synthesized isoprene as reaction product.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant host producing isoprene, said host comprising at least one exogenous nucleic acid encoding (i) a 2-hydroxyacyl-CoA dehydratase or a β-ketoacyl-ACP-synthase; (ii) an acyl-ACP dehydrogenase, a monooxygenase, a cytochrome P450, or a dehydratase classified under EC 4.2.1- and (iii) a mevalonate diphosphate decarboxylase, a mevalonate 3-kinase, an acyl ACP decarboxylating thioesterase, or a linalool dehydratase, said host producing isoprene.

2. The host of claim 1, wherein said host comprises:
   (a) at least one exogenous nucleic acid encoding (i) said 2-hydroxyacyl-CoA dehydratase, (ii) said acyl-ACP dehydrogenase, and (iii) said mevalonate diphosphate decarboxylase, said mevalonate 3-kinase, said acyl-ACP decarboxylating thioesterase, or said linalool dehydratase;
   (b) at least one exogenous nucleic acid encoding (i) said 2-hydroxyacyl-CoA dehydratase, (ii) said monooxygenase or said cytochrome P450, and (iii) said mevalonate diphosphate decarboxylase, said mevalonate 3-kinase, said acyl-ACP decarboxylating thioesterase, or said linalool dehydrates;
   (c) at least one exogenous nucleic acid encoding (i) said β-ketoacyl-ACP-synthase, (ii) said acyl-ACP dehydrogenase, and (iii) said mevalonate diphosphate decarboxylase, said mevalonate 3-kinase, said acyl ACP decarboxylating thioesterase, or said linalool dehydratese; or
   (d) at least one exogenous nucleic acid encoding (i) a dehydratase classified under EC 4.2.1- and (ii) a mevalonate diphosphate decarboxylase or a mevalonate 3-kinase, said host producing isoprene.

* * * * *